US010829779B2

(12) United States Patent
Mou et al.

(10) Patent No.: US 10,829,779 B2
(45) Date of Patent: Nov. 10, 2020

(54) USE OF ELONGATOR GENES TO IMPROVE PLANT DISEASE RESISTANCE

(71) Applicant: University of Florida Research Foundation, Inc., Gainesville, FL (US)

(72) Inventors: Zhonglin Mou, Gainesville, FL (US); Yezhang Ding, La Jolla, CA (US); Xudong Zhang, Gainesville, FL (US); Kevin M. Folta, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 15/743,230

(22) PCT Filed: Jul. 12, 2016

(86) PCT No.: PCT/US2016/041907
§ 371 (c)(1),
(2) Date: Jan. 9, 2018

(87) PCT Pub. No.: WO2017/011462
PCT Pub. Date: Jan. 19, 2017

(65) Prior Publication Data
US 2018/0371490 A1    Dec. 27, 2018

Related U.S. Application Data

(60) Provisional application No. 62/193,001, filed on Jul. 15, 2015.

(51) Int. Cl.
*C12N 15/82* (2006.01)
*A01H 6/74* (2018.01)
*A01H 6/82* (2018.01)
*C07K 14/415* (2006.01)

(52) U.S. Cl.
CPC ........ *C12N 15/8281* (2013.01); *C07K 14/415* (2013.01); *C12N 15/8222* (2013.01); *C12N 15/8282* (2013.01)

(58) Field of Classification Search
None
See application file for complete search history.

(56) References Cited

U.S. PATENT DOCUMENTS

| 2005/0044592 A1* | 2/2005 | Nelissen | ............ | C12N 15/8283 800/287 |
| 2007/0214517 A1* | 9/2007 | Alexandrov | ......... | C07K 14/415 800/278 |
| 2014/0304849 A1 | 10/2014 | Behr et al. | | |

FOREIGN PATENT DOCUMENTS

| WO | WO 2006/114434 A1 | 11/2006 | | |
| WO | WO-2006114434 A1 | * 11/2006 | .......... | C07K 14/415 |

OTHER PUBLICATIONS

Zhou et al, 2009, The Plant Journal, 60:79-90.*
Nelissen et al, 2005, PNAS, 102:7754-7759.*
DeFraia et al, 2013, BMC Plant Biology, 13:1-13 Wang et al (2013, The Plant Cell, 25:762-776.*
Wang et al, 2013, The Plant Cell, 25:762-776.*
Zhang et al, 2010, Eur J Plant Pathol, 128:91-100.*
https://en.wikipedia.org/wiki/Poaceae.*
Silva et al, 2017, BMC Plant Biology, 17:1-12.*
Ding et al, 2015, Frontiers in Plant Science, 6:1-8.*
An et al, 2017, New Phytologist, 214:1245-1259.*
Pereira et al, 2018, Frontiers in Plant Science, 9:1-14.*
Aoki et al, 2010, BMC Genomics, 11:1-16.*
Garcia-Mas et al, 2012, PNAS, 109:11872-11877.*
Defraia, C.T., et al., "Elongator Subunit 3 Positively Regulates Plant Immunity Through Its Histone Acetyltransferase and Radical S-adenosylmethionine Domaines," BMC Plant Biology, 13:1-13 (2013).
Ding, Y., et al., "Elongator and its Epigenetic Role in Plant Development and Responses to Abiotic and Biotic Stresses," Frontiers in Plant Science, 6:1-8 (2015).
Husaini, A.M., et al., "Development of Transgenic Strawberry (Fragaria x ananassa Dusch.) Plants Tolerant to Salt Stress," Plant Science, 174: 446-455 (2008).
Lee, Y., et al., "ELP3 is Involved in Sexual and Asexual Development, Virulences, and the Oxidative Stress Response in *Fusarium garminearum*," Molecular Plant-Microbe Interactions, 27: 1344-1355 (2014).
Mou, Z., "Application of a Natural Inducer of Systemic Acquired Resistance and Engineering Non-host Resistance in Citrus for Controlling Citrus Diseases," Citrus Advanced Technology Program Quarterly and Final Reports: Control of Citrus Greening, Canker and Emerging Diseases of Citrus, p. 2 (2015).
Mou, Z., "Generation of Transgenic Citrus Plants for Resistance Test," Citrus Advanced Technology Program Quarterly and Final Reports: Control of Citrus Greening, Canker and Emerging Diseases of Citrus, p. 1 (2012).
Nelissen, H., et al., "The Elongata Mutants Identify a Functional Elongator Complex in Plants with a Role in Cell Proliferation During Organ Growth," PNAS, 102: 7754-7759 (2005).
PCT International Search Report and Written Opinion of the International Searching Authority for application PCT/US2016/041907 dated Dec. 12, 2016.
Yusuf, M.A., et al., "Overexpression of γ-tocopherol Methyl Transferase Gene in Transgenic Brassica Juncea Plants Alleviates Abiotic Stress: Physiological and Chlorophyll A Fluorescence Measurements," Biochimica et Biophysica Acta, 1428-1438 (2010).

(Continued)

*Primary Examiner* — Jason Deveau Rosen
(74) *Attorney, Agent, or Firm* — Alston & Bird LLP

(57) ABSTRACT

The invention provides methods and compositions for producing plants displaying enhanced disease resistance by transgenic over-expression of Elongator Complex subunit ELP3 or ELP4 genes. Methods and compositions for production of plants with altered growth habit (e.g. runner development) are also provided.

27 Claims, 12 Drawing Sheets
Specification includes a Sequence Listing.

(56) References Cited

OTHER PUBLICATIONS

Pereira, J.A., et al., "The *Arabidopsis* Elongator Subunit ELP3 and ELP4 Confer Resistance to Bacterial Speck in Tomato," Frontiers in Plant Science, 9:1-14 (Jul. 2018).

Silva, KJP, et al., "The *Arabidopsis* ELP3/ELO3 and ELP4/ELO1 genes enhance disease resistance in *Fragaria vesca* L.", *BMC Plant Biology*, 17:230, Dec. 1, 2017, 12 pages.

\* cited by examiner (a)

(c)

(d)

(b)

(a)

(b)

(c)

USE OF ELONGATOR GENES TO IMPROVE PLANT DISEASE RESISTANCE

CROSS REFERENCE TO RELATED APPLICATIONS

This application is a 371 National Stage application of International Application No. PCT/US2016/041907, filed Jul. 12, 2016, which claims benefit of U.S. provisional application No. 62/193,001, filed Jul. 15, 2015, the entire contents of each which are herein incorporated by reference in their entirety.

STATEMENT REGARDING FEDERALLY SPONSORED RESEARCH OR DEVELOPMENT

This invention was made with U.S. Government support under NSF Grant Number IOS-0842716 awarded by the National Science Foundation. The Government has certain rights in the invention.

INCORPORATION OF SEQUENCE LISTING

The Sequence Listing, which is a part of the present disclosure, includes a computer readable form 144,561 bytes file (as measured in MS Word) entitled "UFFL070WO_ST25.txt" created on Jul. 5, 2016 comprising nucleotide and/or amino acid sequences of the present invention submitted via EFS-Web. The subject matter of the Sequence Listing is incorporated herein by reference in its entirety.

BACKGROUND OF THE INVENTION

1. Field of the Invention

The present invention relates generally to the field of agriculture and plant genetics. More particularly, it concerns genetically modified plants comprising enhanced agronomic properties including improved disease resistance.

2. Description of the Related Art

Plants are capable of activating an array of defense mechanisms in response to pathogen attack, some of which are preexisting and others are inducible. However, given the potential susceptibility of plants, new methods and compositions are needed for enhancing the resistance of plants to disease and other biotic and abiotic stresses. Genetic modification of plants has, in combination with conventional breeding programs, led to significant improvements in plant growth, yield, and disease resistance. This may occur for instance by enhancing the ability of plants to recognize the presence of a pathogen and to improve expression of defense mechanisms.

SUMMARY OF THE INVENTION

In one aspect, the invention provides a transgenic plant comprising a heterologous nucleic acid sequence that encodes ELP3 or ELP4 (also called ELO1), wherein ELP3 or ELP4 is over-expressed in the transgenic plant, and exhibits resistance to a disease-causing plant pathogen as a result of the heterologous nucleic acid sequence, relative to an otherwise isogenic plant which does not comprise the heterologous nucleic acid sequence. In some embodiments the heterologous nucleic acid sequence comprises at least 70%, 80%, 85%, 90%, 95%, 98%, 99% or more sequence identity to a sequence selected from the group consisting of SEQ ID NOs: 1-24

In some embodiments the plant pathogen is a bacterial plant pathogen or a fungal plant pathogen. In certain embodiments the nucleic acid sequence encoding ELP3 or ELP4 is operably linked to a heterologous promoter which is a developmentally-regulated, organelle-specific, inducible, tissue-specific, constitutive, cell-specific, or seed specific promoter. In particular embodiments the promoter is a constitutive or inducible promoter.

In certain embodiments the plant is a member of the Brassicaceae, Cucurbitaceae, Fabaceae, Poaceae, Rosaceae, Rutaceae, Malvaceae, or Solanaceae. In some embodiments the plant is a *Brassica*. In particular embodiments the plant is a *Fragaria* sp., a tomato plant, or a *citrus* plant. The plant may further be defined as an $R_0$ transgenic plant. In other embodiments the plant is further defined as a progeny plant of any generation of an $R_0$ transgenic plant, wherein the transgenic plant has inherited the selected DNA from the $R_0$ transgenic plant.

In some embodiments the plant displays an additional altered agronomic property relative to an otherwise isogenic plant which does not comprise the heterologous nucleic acid sequence, wherein the additional altered agronomic property is selected from the group consisting of: enhanced yield; altered leaf area; altered leaf shape, and altered production of runners.

Another aspect of the invention provides a seed that produces the plant comprising a heterologous nucleic acid sequence that encodes ELP3 or ELP4, wherein ELP3 or ELP4 is over-expressed in the transgenic plant, and exhibits resistance to a disease-causing plant pathogen as a result of the heterologous nucleic acid sequence, relative to an otherwise isogenic plant which does not comprise the heterologous nucleic acid sequence. A part of the plant is also provided. The plant part may further be defined, in some embodiments of the invention, as a protoplast, cell, meristem, root, leaf, pistil, anther, flower, seed, fruit, embryo, stalk, or petiole.

Another aspect of the invention provides a recombinant nucleic acid molecule comprising a nucleic acid sequence selected from the group consisting of: (a) a nucleic acid sequence that hybridizes to a nucleic acid sequence complementary to the sequence of any of SEQ ID NOs: 1-24, under wash conditions of 1×SSC and 65° C.; (b) a nucleic acid comprising the sequence complementary to SEQ ID NOs: 1-24 or a fragment thereof; and c) a nucleic acid sequence exhibiting at least 80% sequence identity to any of SEQ ID NOs: 1-24; wherein the nucleic acid sequence is operably linked to a heterologous promoter sequence and wherein expression of the nucleic acid molecule in a plant cell results in over-expression of ELP3 or ELP4 relative to an otherwise isogenic plant which does not comprise the heterologous nucleic acid sequence. In some embodiments the DNA molecule comprises a nucleic acid sequence exhibiting at least 70%, 80%, 85%, 90%, 95%, 96%, 97%, 98% or 99% sequence identity to a complement of any of SEQ ID NOs: 1-24. Further, the heterologous promoter sequence may be developmentally-regulated, organelle-specific, inducible, tissue-specific, constitutive, cell-specific, or seed specific promoter.

Another aspect of the invention relates to a transgenic plant cell comprising the nucleic acid molecule comprising a nucleic acid sequence selected from the group consisting of: (a) a nucleic acid sequence that hybridizes to a nucleic acid sequence complementary to the sequence of any of SEQ ID NOs: 1-24, under wash conditions of 1×SSC and 65° C.; (b) a nucleic acid comprising the sequence complementary to SEQ ID NOs: 1-24 or a fragment thereof; and c) a nucleic acid sequence exhibiting at least 80% sequence identity to any of SEQ ID NOs: 1-24; wherein the nucleic acid sequence is operably linked to a heterologous promoter sequence and wherein expression of the nucleic acid molecule in a plant cell results in over-expression of ELP3 or ELP4 relative to an otherwise isogenic plant which does not comprise the heterologous nucleic acid sequence. A transgenic plant or plant part, such as a leaf, seed, flower, ovary, pollen, or fruit comprising such a nucleic acid molecule is also contemplated.

Another aspect of the invention provides a method of conferring disease resistance to a plant comprising: over-expressing a heterologous nucleic acid sequence that encodes ELP3 or ELP4 in a transgenic plant; wherein the transgenic plant exhibits disease resistance, as a result of the over-expression of the heterologous nucleic acid sequence, relative to an otherwise isogenic plant which does not comprise the heterologous nucleic acid sequence. In certain embodiments the disease is a bacterial plant disease or a fungal plant disease. In some embodiments of the method the disease is caused by a fungus. In particular embodiments the disease is Strawberry Anthracnose or Strawberry Powdery Mildew. In other embodiments the disease is caused by a bacterium. In particular embodiments the disease is caused by a Pseudomonad, a Xanthomonad, or an *Erwinia* sp. In certain embodiments the disease is Strawberry Angular Leaf Spot, or Bacterial Speck of Tomato.

The invention further relates to a method of plant breeding comprising: (a) crossing a first plant, which is over-expressing a heterologous nucleic acid sequence that encodes ELP3 or ELP4, wherein ELP3 or ELP4 is over-expressed in the first plant, and wherein the first plant exhibits disease resistance as a result of the heterologous nucleic acid sequence relative to an otherwise isogenic plant which does not comprise the heterologous nucleic acid sequence, with a second plant; (b) obtaining one or more progeny plants, and (c) selecting a progeny plant which is over-expressing the heterologous nucleic acid sequence that encodes ELP3 or ELP4, wherein ELP3 or ELP4 is over-expressed in the progeny plant, and wherein the progeny plant exhibits disease resistance as a result of the heterologous nucleic acid sequence, relative to an otherwise isogenic plant which does not comprise the heterologous nucleic acid sequence.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 1(c): Leaf morphology of Col-0 and the T-DNA insertion mutant line SALK_079193. "CFU": colony-forming unit.

BRIEF DESCRIPTION OF THE SEQUENCES

Figure 1:
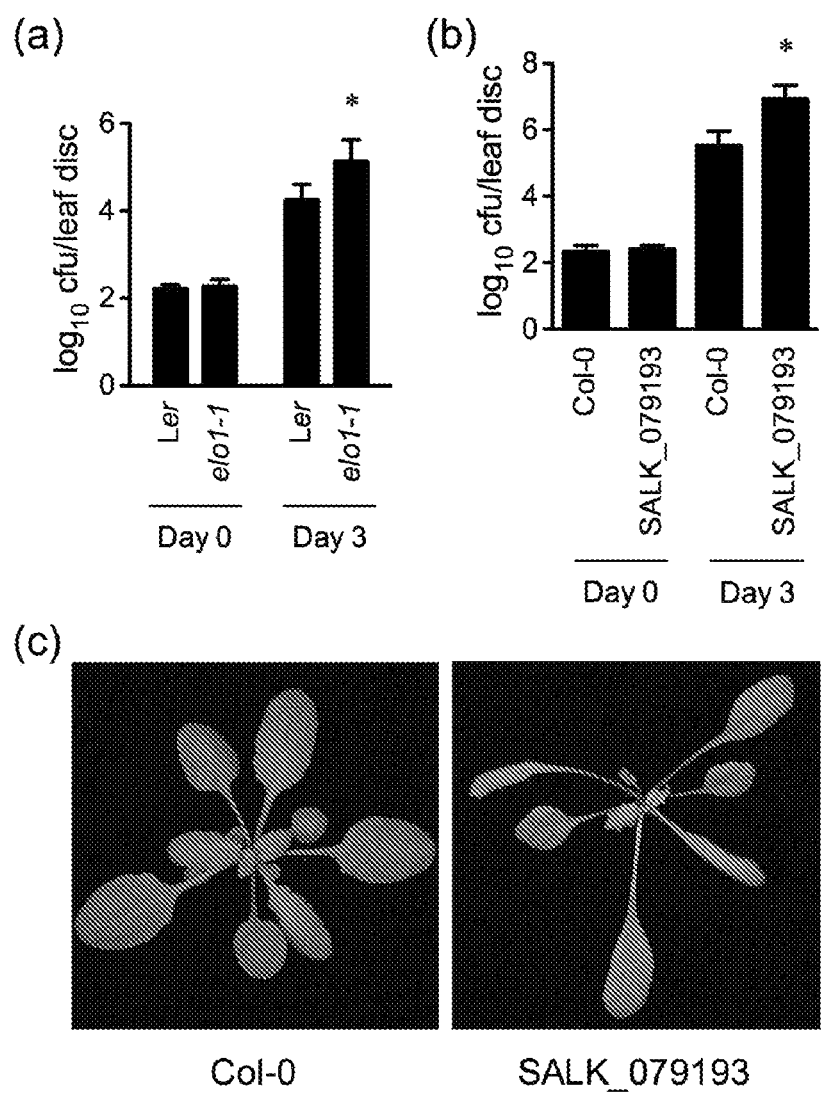
FIG. 1. (a): Bacterial multiplication ($\log_{10}$ CFU/leaf disc) of *A. thaliana* ecotype Landsberg *erecta* ("Ler") and elo1-1 lines challenged with the bacterial pathogen strain *Pseudomonas syringae* pv. *maculicola* ("Psm") ES4326. The asterisk indicates that elo1-1 is significantly more susceptible than Ler to Psm ES4326 ($p<0.05$, Student's t test). (b): Bacterial multiplication ($\log_{10}$ CFU/leaf disc) of *A. thaliana*, ecotype Columbia ("Col-0") and the T-DNA insertion mutant SALK_079193, challenged with Psm ES4326. The asterisk indicates that SALK_079193 is significantly more susceptible than Col-0 to Psm ES4326 ($p<0.05$, Student's t test).

SEQ ID NOs:1-12 ELP3 nucleotide sequences from *Arabidopsis thaliana, Brassica napus, Gossypium arboreum, Glycine max, Citrus sinensis, Solanum lycopersicum, Medicago truncatula, Fragaria vesca, Cucumis melo, Zea mays, Oryza sativa,* and *Eucalyptis grandis*, respectively.

SEQ ID NOs:13-24 ELP4 nucleotide sequences from *Arabidopsis thaliana, Brassica napus, Gossypium arboreum, Glycine max, Citrus sinensis, Solanum lycopersicum, Medicago truncatula, Fragaria vesca, Cucumis melo, Zea mays, Oryza sativa,* and *Eucalyptis grandis* respectively.

SEQ ID NOs:25-36 predicted ELP3 polypeptide sequences from *Arabidopsis thaliana, Brassica napus, Gossypium arboreum, Glycine max, Citrus sinensis, Solanum lycopersicum, Medicago truncatula, Fragaria vesca, Cucumis melo, Zea mays, Oryza sativa,* and *Eucalyptis grandis* respectively.

SEQ ID NOs:37-48 predicted ELP4 polypeptide sequences from *Arabidopsis thaliana, Brassica napus, Gossypium arboreum, Glycine max, Citrus sinensis, Solanum lycopersicum, Medicago truncatula, Fragaria vesca, Cucumis melo, Zea mays, Oryza sativa,* and *Eucalyptis grandis* respectively.

DETAILED DESCRIPTION OF THE INVENTION

The invention relates, in one aspect, to the surprising discovery that plants such as *Brassicas, Citrus*, tomatoes, and strawberries, among others, may be engineered to over express certain subunits of the Elongator Complex, including ELP3 and ELP4, in order to exhibit enhanced resistance to bacterial and fungal plant pathogens. This discovery is unexpected because the effect of such over expression was not known or predictable with respect to the level of plant disease resistance as well as effects on morphology, growth, flowering, and yield. Thus, the invention overcomes limitations in the art by providing plants engineered to be resistant to multiple plant pathogens, and also provides methods for producing plants with enhanced resistance to bacterial and fungal plant pathogens. Plants that are provided include transgenic dicotyledonous and monocotyledonous plants comprising heterologous DNA sequences that lead to over-expression of Elongator Complex Subunit 3 ("ELP3") or Elongator Complex Subunit 4 ("ELP4").

Elongator is a multifunctional protein complex involved in many cellular processes, such as transcriptional regulation, histone acetylation and gene silencing (DeFraia and Mou, *Plant Signal. Behavior* 6:19-22, 2011), operating in association with RNA polymerase II (RNAPII) during transcription (Otero et al., *Mol. Cell* 3:109-118, 1999). Composed of six protein subunits (ELP1, ELP2, ELP3, ELP4, ELP5 and ELP6), this complex controls many cellular processes such as histone modification/acetylation, exocytosis, α-tubulin acetylation, response to DNA damage, transcriptional silencing, zygotic paternal genomic demethylation, and tRNA nucleoside modification (Creppe and Buschbeck *J. Biomed. Biotechnol.* 2011:924898, 2011; Esberg et al., *Mol. Cell* 24:139-148, 2006; Huang et al., *RNA* 11:424-436, 2005; Li et al., PLoS Genetics 5:e1000684, 2009; Okada et al., *Nature* 463:554-558, 2010; Rahl et al., *Mol. Cell* 17:841-853, 2005; Wittschieben et al., *Mol. Cell* 4:123-128, 1999). ELP1-ELP3 encode the core complex, whereas ELP4-ELP6 encode components of a subcomplex that forms a hetero-hexameric ring-like structure which is essential for the binding of anticodon stem-loop of substrate tRNAs (Glatt et al., *Nature Struct. Mol. Biol.* 19:314-320, 2012). The Elongator Complex is highly conserved in eukaryotes; however, the effects of its over-expression in higher plant are not well understood. The present disclosure demonstrates that over-expression of ELP3 and ELP4 confers enhanced resistance to multiple diseases and provides an alternative for producing plants resistant to fungal and bacterial pathogens.

Plants have developed various defense mechanisms in response to infection. Plants defend themselves against pathogens by recognizing them, and then rapidly and efficiently reprogramming their transcriptional profiles to mount a very complex and accurate precise defense strategy. However, unlike animals, they lack mobile defense cells and a somatic adaptive immune system, and so rely on their innate immunity. This defense leads to the recognition of pathogen-associated molecular patterns (PAMPs), resulting in PAMP-triggered immunity (PTI) that prevents pathogen colonization, along with induction of effector-triggered immunity ("ETI"), that triggers the activation of resistance ("R") proteins. These signals lead to the generation of a systemic acquired resistance ("SAR") response, which confers long-lasting protection against a broad spectrum of microbial pathogens. Salicylic acid ("SA") is a signal molecule essential for activation of SAR and also associated with accumulation of the pathogenesis-related ("PR") proteins that contribute to resistance. Effective SA-mediated resistance requires the transcriptional co-activator NPR1, which regulates the activity of several transcription factors that modulate defense gene expression (Cao et al., *Cell* 88:57-67, 1997; Durrant and Dong, *Ann. Rev. Phytopathol.* 42:185-209, 2004). Mutations in the NPR1 gene significantly suppress SA-mediated transcriptional reprogramming, and lead to compromised basal immunity, ETI, and SAR (Durrant and Dong, 2004, ibid). In addition, these mutations also result in SA hyperaccumulation during pathogen infection (Shah et al., *Mol. Plant Microbe Interact* 10:69-78, 1997; Wildermuth et al., *Nature* 414:562-565, 2001) and failure of seedling development on Murashige and Skoog (MS) medium containing high concentrations of SA (Cao et al., 1997, ibid).

Independently of SAR, components of the Elongator Complex (EC) may also play a role in immunity (Chen et al. *Mol. Cell Biol.* 26:6902-6912, 2006; DeFraia et al. *Plant J.* 64:511-523, 2010; DeFraia and Mou, *Plant Signal. Behavior* 6:19-22, 2011; Wang et al., *Plant Cell* 25:762-776, 2013; Zhou et al., *Plant J.* 60:79-90, 2009). Plants lacking certain Elongator subunits are more susceptible to plant pathogens. ELP3 contains both histone acetyltransferase (HAT), which connects chromatin structure deformation with elevated transcription activity mediated by RNAPII, and a radical S-AdoMet (SAM) domain, linked to the protein by an iron-sulphur cluster (Paraskevopoulou et al., *Mol. Microbiol.* 59:795-806, 2006). In *Arabidopsis*, AtELP3 plays a role in regulating transcriptional changes induced during pathogen infection and are accompanied by changes in DNA methylation, a hallmark of transcriptional suppression and histone acetylation, which is generally associated with transcriptional activation (DeFraia et al. 2010, ibid; Kass et al., *Trends Genet.* 13:444-449, 1997; Workman and Kingston, *Ann. Rev. Biochem.* 67:545-579, 1998). In *Arabidopsis*, AtELP4 is required for rapid defense gene induction and establishment of full basal and effector-triggered plant immunity.

In general, mutations of Elongator subunits in *Arabidopsis* result in pleiotropic effect including: abscisic acid (ABA) hypersensitivity; tolerance to drought or oxidative stress; severely aberrant auxin phenotypes like narrow leaves and reduced root growth; accumulation of anthocyanin; and reduced apical dominance (Chen et al. 2006, ibid; DeFraia et al. 2013, *BMC Plant Biol.* 13:102; DeFraia et al. 2010, ibid; Huang et al., *RNA* 11:424-436, 2005; Nelissen et al., *Plant Cell* 15:639-654, 2003; Nelissen et al., *PNAS* 107: 1678-1683, 2010; Wang et al. 2013, ibid; Yan et al., *Plant Physiol. And tRNA Modification* 13:1640-1650, 2014; Zhou et al., *Plant J.* 60:79-90, 2009). However, the effect of ELP3 or ELP4 over-expression was unclear.

In one embodiment, a plant provided by the invention is more resistant to bacterial or fungal diseases than an otherwise similar plant not comprising a recombinant DNA construct that allows for an increase in the level of expression of ELP3 or ELP4. A first plant can be considered more resistant to plant disease than a second plant when the first plant exhibits less disease, such as symptomatology and pathogen multiplication, or the disease progresses more slowly in the first plant than in the second plant. The amount of disease infecting a plant can be measured by any means known in the art. For instance, "area under the disease progress curve ("AUDPC"; Shaner & Finney, *Phytopathol.* 67:1051-1056, 1977) may be measured. Loss of foliage, necrosis, wilting, or other symptoms can also be measured, as well as levels of pathogen population or multiplication.

Plant pathogens contemplated herein for control via enhanced plant resistance include bacterial and fungal plant pathogens, for instance biotrophic or hemibiotrophic pathogens. In certain embodiments the contemplated plant pathogen is a gram-negative plant pathogenic bacterium such as a Xanthomonad or a Pseudomonad, or an Ascomycete such as a member of the Erysiphaceae or the Glomerellaceae. Levels of resistance may be positively correlated with the levels of transgene expression in transgenic lines.

As an example, ectopic expression of AtELP3 and AtELP4 in strawberry increased resistance to *C. gloeosporioides*, causal agent of anthracnose crown rot. This pathogen aggressively invaded the plant tissue and control plants collapsed within 20 days. However, plants over-expressing ELP3 or ELP4 demonstrated a reduction in disease symptoms of at least 25% to 50%, and higher levels of transgene expression promoted increased resistance to, for instance, *Podosphaeria aphanis*, with a tested transgenic line E4/01 not presenting any symptoms of disease. Spores counted in leaves of these plants may actually have remained from inoculation, as this fungus can survive on leaves and remain on the plants for a long period of time.

AtELP3 and AtELP4 plants were also more resistant to a bacterial pathogen. In this instance, inoculation sites did not develop coalescing and necrotic lesions 20 days after infection ("dai") with *Xanthomonas fragariae*; and progression of symptoms and bacterial growth were decreased in most lines, with transgenic lines E4/01 and E4/06 displaying the most resistance. These results showed that AtELP3 and AtELP4 expression promoted increased disease resistance in strawberry plants. When compared to strawberry plants overexpressing AtNPR1 and challenged with the same pathogens (Silva et al., *Transgenic Res.* 1-12, doi:10.1007/ s11248-015-9869-5, 2015), ELP3- and ELP4-over-expressing plants showed higher levels of resistance, allowing for improvement in development of strawberry cultivars resistant to diseases.

Contemplated plants displaying enhanced disease resistance and/or altered growth include any plant that is a host of a bacterial or fungal plant pathogen, and which could thus be made more disease resistant using the constructs and methods as described herein. Exemplary plants include *Arabidopsis thaliana, Brassica napus, Gossypium* sp., *Glycine max, Citrus sinensis, Solanum lycopersicum, Medicago truncatula, Fragaria vesca, Cucumis melo, Zea mays, Oryza sativa,* and *Eucalyptis grandis* among others. Included are plants grown for food, feed, fuel, timber, forage, or fiber, as well as ornamental plants. In some embodiments, the plant is a member of the Brassicaceae, the Rosaceae, the Fabaceae, the Poaceae, the Solanaceae, or the Rutaceae. In specific embodiments, the plant is a strawberry plant, a soybean plant, a corn plant, a *Citrus* plant, a tomato plant, a cotton plant, or a canola plant. Methods to produce transgenic plants comprising a heterologous sequence encoding a functional ELP3 or ELP4 gene, to over-express such gene products, are also provided.

I. APPLICATION OF THE INVENTION

As indicated above, one application of the invention is to provide methods to increase the resistance of a plant to bacterial and fungal plant pathogens. Modulation of the phenotype of a plant or plant tissue may be obtained in accordance with the invention by introduction of recombinant nucleic acid sequences that result in increased, e.g. constitutive, synthesis of ELP3 or ELP4. Such sequences may be identical to or display, for example, at least 75%, 80%, 85%, 90%, 95%, 98%, or 99% sequence identity with, for instance, SEQ ID NOs:1-24. Transgenic plants comprising a heterologous nucleic acid sequence encoding a functional polypeptide of SEQ ID NOs:25-48, or functional polypeptides displaying at least 75%, 80%, 85%, 90%, 95%, 98%, or 99% sequence identity to any of SEQ ID NOs:25-48 are also contemplated. As used herein, "hybridization" or "hybridizes" is understood to mean the forming of a double or triple stranded molecule or a molecule with partial double or triple stranded nature. As used herein "stringent condition(s)" or "high stringency" are those conditions that allow hybridization between or within one or more nucleic acid strand(s) containing complementary sequence(s), but precludes hybridization of random sequences.

Stringent conditions tolerate little mismatch between a nucleic acid and a target strand. Such conditions are well known to those of ordinary skill in the art, and are preferred for applications requiring high selectivity. Medium stringent conditions may comprise relatively low salt and/or relatively high temperature conditions, such as provided by about 1×SSC, and 65° C. High stringency may be defined as 0.02M to 0.10M NaCl and 50° C. to 70° C. Specific examples of such conditions include 0.02M NaCl and 50° C.; 0.02M NaCl and 60° C.; and 0.02M NaCl and 70° C.

Alterations of the native amino acid sequence to produce variant polypeptides can be prepared by a variety of means known to those ordinarily skilled in the art. For instance, amino acid substitutions can be conveniently introduced into the polypeptides by changing the sequence of the nucleic acid molecule at the time of synthesis. Site-specific mutations can also be introduced by ligating into an expression vector a synthesized oligonucleotide comprising the modified sequence. Alternately, oligonucleotide-directed, site-specific mutagenesis procedures can be used, such as disclosed in Walder et al, (*Gene* 42:133, 1986); and U.S. Pat. Nos. 4,518,584 and 4,737,462.

In making such changes, the hydropathic index of amino acids may be considered. The importance of the hydropathic amino acid index in conferring interactive biological function on a protein is generally understood in the art (e.g. Kyte and Doolittle, *J. Mol. Biol.* 157:105-132, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid may be assigned a hydropathic index on the basis of their hydrophobicity and charge characteristics. These are, for instance: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

It is also understood in the art that the substitution of like amino acids may be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid may be substituted by another amino acid having a similar hydrophilicity score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those skilled in the art and include: arginine and lysine; glutamate and aspartate; serine and threonine; glutamine and asparagine; and valine, leucine, and isoleucine.

It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture. It is also understood that compositions and conditions for hybridization are mentioned by way of non-limiting examples only, and that the desired stringency for a particular hybridization reaction in a plant cell is often determined empirically by comparison to one or more positive or negative controls. Depending on the application envisioned it is preferred to employ varying conditions of hybridization to achieve varying degrees of selectivity of a nucleic acid towards a target sequence. Thus, recombinant DNA constructs comprising nucleotide sequences identical to, or displaying 75%, 80%, 85%, 90%, 95%, 98%, 99%, or greater identity, over the complete length of their coding regions to any of SEQ ID NOs: 1-24 and that encode a functional ELP3 or ELP4 polypeptide may be utilized in the present invention. The coding sequences of such genes may be operably linked to and under transcriptional control of a constitutive, root-preferred, and/or inducible promoter as outlined below.

II. PLANT TRANSFORMATION CONSTRUCTS

Certain embodiments of the current invention concern plant transformation constructs. For example, one aspect of the current invention is a plant transformation vector comprising a nucleotide sequence that encodes a polypeptide which functions as an Elongator Complex subunit ELP3 or ELP4. Such coding sequences may be present in one or more plant expression cassettes and/or transformation vectors for introduction to a plant cell.

In certain embodiments of the invention, coding sequences are provided operably linked to a heterologous promoter, which exhibits a constitutive or inducible pattern of gene expression. Expression constructs are also provided comprising these sequences, as are plants and plant cells transformed with the sequences.

The construction of vectors which may be employed in conjunction with plant transformation techniques using these or other sequences according to the invention will be known to those of skill in the art in light of the present disclosure (see, for example, Sambrook et al., In: *Molecular Cloning—A Laboratory Manual* (second edition), Cold Spring Harbour Laboratory Press, 1989; Gelvin et al., *Pl. Mol. Biol.* Manual 1990). The techniques of the current invention are thus not limited to any particular nucleic acid sequences.

One important use of the sequences provided by the invention will be in the alteration of a plant disease resistance phenotype by genetic transformation with an ELP3- or ELP4-coding gene. Alternatively, plant growth habit (e.g. runner formation) may be altered. The ELP3 or ELP4-coding gene that allows for an altered phenotype, such as enhanced plant disease resistance, may be provided along with other sequences, for instance, sequences that function as selectable or screenable markers. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize co-transformation.

DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a nucleic acid sequence include plant promoter such as the CaMV 35S promoter (Odell et al., *Nature* 313:810-812, 1985), or others such as CaMV 19S (Lawton et al., *Plant Mol. Biol.* 9:315-324, 1987), nos (Ebert et al., *PNAS* 84:5745-5749, 1987), ocs (Herrera-Estrella et al, *Nature* 303:209-213, 1983), Adh (Walker et al., *PNAS* 84:6624-6628, 1987), sucrose synthase (Yang and Russell, *PNAS* 87:4144-4148, 1990), a-tubulin, actin (Wang et al., *Mol. Cell Biol.* 12:3399-3406, 1992), cab (Sullivan et al., *Mol. Gen. Genet.* 215:431-440, 1989), PEPCase (Hudspeth and Grula, *Plant Mol. Biol.* 12:579-589, 1989). Tissue specific promoters such as root cell promoters (Conkling et al., *Pl. Physiol.* 93:1203-1211, 1990) and tissue specific enhancers (Fromm et al., *Nature* 319: 791-793, 1986) are also contemplated to be useful, as are inducible promoters such as ABA- and turgor-inducible promoters. The choice of such promoter sequences will be known to those of skill in the art in light of the present disclosure.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is specifically envisioned that ELP3 or ELP4 coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots and elsewhere, and an α-tubulin gene that also directs expression in roots.

B. Terminators

Transformation constructs prepared in accordance with the invention will typically include a 3' end DNA sequence that acts as a signal to terminate transcription and allow for the poly-adenylation of the mRNA produced by coding sequences operably linked to, for instance, a ELP3 or ELP4 encoding gene. In one embodiment of the invention, the native terminator of a FS or IFS gene is used. Alternatively, a heterologous 3' end may enhance the expression of the ELP3 or ELP4 gene(s). Terminators which are deemed to be particularly useful in this context include those from the nopaline synthase gene of *Agrobacterium tumefaciens* (nos 3' end) (Bevan et al., NAR 11:369-385, 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., *Genes Devel.* 1:1183-1200, 1987), sucrose synthase intron (Vasil et al., *Pl. Physiol.* 91:1575-1579, 1989) or TMV omega element (Gallie et al., *Plant Cell* 1:301-311, 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms "selectable" or "screenable markers" also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

Many selectable marker coding regions are known and could be used with the present invention including, but not limited to, neo (Potrykus et al., *Mol. Gen. Genet.* 199:183-188, 1985), which provides kanamycin resistance and can be selected for using kanamycin, G418, paromomycin, etc.; bar, which confers bialaphos or phosphinothricin resistance; a mutant EPSP synthase protein (Hinchee et al., *Bio/Technol* 6:915-922, 1988) conferring glyphosate resistance; a nitrilase such as bxn from *Klebsiella ozaenae* which confers resistance to bromoxynil (Stalker et al., *Science* 242:419-422, 1988); a mutant acetolactate synthase (ALS) which confers resistance to imidazolinone, sulfonylurea or other ALS inhibiting chemicals (European Patent Application 154,204, 1985); a methotrexate resistant DHFR (Thillet et al., *J. Biol. Chem.* 263:12500-12508, 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.* 205:42-50, 1986; Twell et al., *Pl. Physiol.* 91:1270-1274, 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., In: *Chromosome Structure and Function: Impact of New Concepts, 18th Stadler Genetics Symposium,* 11:263-282, 1988); a β-lactamase gene (Sutcliffe, *PNAS* 75:3737-3741, 1978), which encodes an enzyme for which various chromogenic substrates are known (e.g., PADAC, a chromogenic cephalosporin); a xylE gene (Zukowsky et al., *PNAS* 80:1101-1105, 1983) which encodes a catechol dioxygenase that can convert chromogenic catechols; an α-amylase gene (Ikuta et al., *Bio/technol* 8:241-242, 1990); a tyrosinase gene (Katz et al., *J. Gen. Microbiol.* 129:2703-2714, 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., *Science* 234:856-859, 1986), which allows for bioluminescence detection; an aequorin gene (Prasher et al., *BBRC* 126:1259-1268, 1985) which may be employed in calcium-sensitive bioluminescence detection; or a gene encoding for green fluorescent protein (Sheen et al., *Plant J.* 8:777-784, 1995; Haseloff et al., *PNAS* 94:2122-2127, 1997; Reichel et al., *PNAS* 93:5888-5893, 1996; Tian et al., *Pl. Cell Rep.* 16:267-271, 1997; WO 97/41228).

Another screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening.

III. TISSUE CULTURES

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bacto™ agar (Difco-BD, Franklin Lakes, N.J.), Hazleton agar (Hazleton, Lenexa, Kans., USA), Gelrite® (Sigma, St. Louis, Mo.), PHYTAGEL (Sigma-Aldrich, St. Louis, Mo.), and GELGRO (ICN-MP Biochemicals, Irvine, Calif., USA) are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, callus, immature embryos, hairy root cultures, and gametic cells such as microspores, pollen, sperm and egg cells. Callus may be initiated from tissue sources including, but not limited to, immature embryos, seedling apical meristems, root, leaf, microspores and the like. Those cells which are capable of proliferating as callus also are candidate recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population, for example by manual selection and culture of friable, embryogenic tissue. Manual selection techniques which can be employed to select target cells may include, e.g., assessing cell morphology and differentiation, or may use various physical or biological means. Cryopreservation also is a possible method of selecting for recipient cells.

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al., *Scientia Sinica* 18:659-668, 1975) and MS media (Murashige and Skoog, *Physiol. Plant.* 15:473-497, 1962).

IV. METHODS FOR GENETIC TRANSFORMATION

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., *Plant Mol. Biol.* 21:415-428, 1993), by desiccation/inhibition-mediated DNA uptake (Potrykus et al., ibid, 1985), by electroporation (U.S. Pat. No. 5,384,253, specifically incorporated herein by reference in its entirety), by agitation with silicon carbide fibers (Kaeppler et al., *TAG* 84:560-566, 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, the cells of virtually any plant species may be stably transformed, and these cells developed into transgenic plants.

A. *Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., *Bio/Technol.* 3:629-635, 1985), Rogers et al., (*Methods Enzymol.* 153:253-277, 1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., *Plant Mol. Biol.* 35:205-218, 1997; U.S.

Pat. No. 5,591,616), wheat (McCormac et al., *Euphytica* 99:17-25, 1998), barley (Tingay et al., *Plant J.* 11:1369-1376, 1997), alfalfa (e.g. Thomas et al., *Pl. Sci.* 69:189-198, 1990; McKersie et al., *Pl. Physiol.* 103:1155-1163, 1993; Chabaud et al., *Pl. Cell Rep.* 22:46-51, 1993) and maize (Ishida et al., *Naute Biotechnol.* 14:745-750, 1996).

Modern *Agrobacterium* transformation vectors are capable of replication in *E. coli* as well as *Agrobacterium*, allowing for convenient manipulations as described (Klee et al., *Bio/Technol.* 3:637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., ibid. 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., *Methods Mol. Biol.* 55:121-131, 1995; D'Halluin et al., *Plant Cell* 4:1495-1505, 1992), wheat (Zhou et al., *Pl. Cell Rep.* 12:612-616, 1993), tomato (Hou and Lin, *Pl. Physiol.* 111:166, 1996), soybean (Christou et al., *PNAS* 84:3962-3966, 1987) and tobacco (Lee et al., *Korean J. Genet.* 11:65-72, 1989).

One also may employ protoplasts for electroporation transformation of plants (Bates, *Mol. Biotechnol.* 2:135-145, 1994; Lazzeri, *Methods Mol. Biol.* 49:95-106, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, ibid., 1995), sorghum (Battraw et al., *TAG* 82:161-168, 1991), maize (Bhattacharjee et al., *J. Plant Biochem. Biotechnol.* 6:69-73, 1997), wheat (He et al., *Pl. Cell Rep.* 14:192-196, 1994) and tomato (Tsukada, *Pl. Cell Physiol.* 30:599-604, 1989).

C. Microprojectile Bombardment

Another method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics® Particle Delivery System (Dupont), which can be used to propel particles coated with DNA or cells through a screen, such as a stainless steel or nylon screen (e.g. NYTEX screen; Sefar America, Depew, N.Y. USA), onto a filter surface covered with plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., *Pl. Mol. Biol.* 24:317-325, 1994), wheat (U.S. Pat. No. 5,563,055), and sorghum (Casa et al., *PNAS* 90:11212-11216, 1993); as well as a number of dicots including tobacco (Tomes et al., *Plant Mol. Biol.* 14:261-268, 1990; Buising and Benbow, *Mol. Gen. Genet.* 243:71-81, 1994), soybean (U.S. Pat. No. 5,322,783), sunflower (Knittel et al., *Pl. Cell Rep.* 14:81-86, 1994), peanut (Singsit et al., *Transgenic Res.* 6:169-176, 1997), cotton (McCabe and Martinell, *Bio/Technol.* 11:596-598, 1993), tomato (VanEck et al., *Pl. Cell Rep.* 14:299-304, 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985, ibid.; Lorz et al., *Mol. Gen. Genet.* 199:178-182, 1985; Omirulleh et al., 1993, ibid.; Fromm et al., 1986, ibid.; Uchimiya et al., *Mol. Gen. Genet.* 204:204, 1986; Callis et al., 1987, ibid.; Marcotte et al., *Nature* 335:454, 1988).

Application of these systems to different plant strains depends upon the ability to regenerate that particular plant strain from protoplasts. Illustrative methods for the regeneration of plants from protoplasts have been described (Toriyama et al., *TAG* 73:16, 1986; Yamada et al., *Pl. Cell Rep.* 4:85, 1986; Abdullah et al., *Bio/Technol.* 4:1087, 1986; Omirulleh et al., 1993, ibid. and U.S. Pat. No. 5,508,184). Examples of the use of direct uptake transformation of protoplasts include transformation of rice (Ghosh-Biswas et al., *J. Biotechnol.* 32:1-10, 1994), sorghum (Battraw and Hall, 1991, ibid.), barley (Lazerri, 1995, ibid.), oat (Zheng and Edwards, *J. Gen. Virol.* 71:1865-1868, 1990) and maize (Omirulleh et al., 1993, ibid).

To transform plant strains that cannot be successfully regenerated from protoplasts, other ways to introduce DNA into intact cells or tissues can be utilized. For example, regeneration of cereals from immature embryos or explants can be effected as described (Vasil, 1989, ibid). Also, silicon carbide fiber-mediated transformation may be used with or without protoplasting (Kaeppler, *Pl. Cell Rep.* 9:415-418, 1990; Kaeppler et al., *TAG* 84:560-566, 1992; U.S. Pat. No. 5,563,055). Transformation with this technique is accomplished by agitating silicon carbide fibers together with cells in a DNA solution. DNA passively enters as the cells are

V. PRODUCTION AND CHARACTERIZATION OF STABLY TRANSFORMED PLANTS

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., *Sc. Rep.* 13:42-48, 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., *EMBO J.* 6:2519-2523, 1987). The bar gene has been cloned (Murakami et al., 1986, ibid.; Thompson et al., 1987, ibid) and expressed in transgenic tobacco, tomato, potato (De Block et al., *EMBO J.* 6:2513-2518, 1987) *Brassica* (De Block et al., *Pl. Physiol.* 91:694-701, 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

It further is contemplated that the herbicide DALAPON, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (Buchanan-Wollaston et al., *Pl. Cell Rep.* 11:627-631, 1992; U.S. Pat. No. 5,508,468).

Alternatively, a gene encoding anthranilate synthase, which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. No. 5,508,468.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cells or tissue types, a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soil-less plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants are preferably matured either in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plantcon™ containers (MP-ICN Biomedicals, Solon, Ohio, USA). Regenerating plants are preferably grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$ M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note that intact sequences will not always be present, presumably due to rearrangement or deletion of sequences in the cell. The presence of DNA elements introduced through the methods of this invention may be determined, for example, by polymerase chain reaction (PCR). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR analysis. In addition, it is not typically possible using PCR™ techniques to determine whether transformants have exogenous genes introduced into different sites in the genome, i.e., whether transformants are of independent origin. It is contemplated that using PCR techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR, e.g., the presence of a gene, but also demonstrates integration into the genome and characterizes each individual transformant.

Whereas DNA analysis techniques may be conducted using DNA isolated from any part of a plant, RNA will only be expressed in particular cells or tissue types and hence it will be necessary to prepare RNA for analysis from these tissues. PCR techniques also may be used for detection and quantitation of RNA produced from introduced genes. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by northern blotting. This technique will demonstrate the presence of an RNA species and give information about the integrity of that RNA. The presence or absence of an RNA species also can be determined using dot or slot blot northern hybridizations. These techniques are modifications of northern blotting and will only demonstrate the presence or absence of an RNA species.

E. Gene Expression

While Southern blotting and PCR may be used to detect the gene(s) in question, they do not provide information as to whether the corresponding protein is being expressed. Expression may be evaluated by determining expression via transcript-profiling techniques such as by use of a microarray, and by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}C$-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

VI. BREEDING PLANTS OF THE INVENTION

In addition to direct transformation of a particular plant genotype with a construct prepared according to the current invention, transgenic plants may be made by crossing a plant having a selected DNA of the invention to a second plant lacking the construct. For example, a selected CT biosynthesis gene can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VII. DEFINITIONS

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found. In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Over-expression: As defined herein, "over-expression" is defined as an increased level of mRNA encoding a gene of interest, or an increased level of the translational product thereof within the plant. For instance in a transgenic plant this may be measured relative to an otherwise isogenic plant which does not comprise a transgene encoding the gene of interest.

Promoter: A recognition site on a DNA sequence or group of DNA sequences that provides an expression control element for a structural gene and to which RNA polymerase specifically binds and initiates RNA synthesis (transcription) of that gene. A "constitutive promoter" allows for continual transcription of its associated gene. The term "constitutive" as used herein does not necessarily indicate that a gene is expressed at the same level in all cell types, but that the gene is expressed in a wide range of cell types, although some variation in abundance is often observed. An "inducible promoter" is a promoter that is capable activating transcription of one or more DNA sequences or genes in response to an inducer. The inducer can be, for instance, a chemical agent, a physiological stress or condition, or a pathogen.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule capable of replication in a host cell and/or to which another DNA segment can be operatively linked so as to bring about replication of the attached segment. A plasmid is an exemplary vector.

VIII. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Mutation of AtELP4 Compromises Basal Resistance to a Bacterial Plant Pathogen

A pathogen growth assay was performed on an elo1-1/Atelp4 mutant *Arabidopsis* line which contains a mutation (G to A) at the acceptor splice site of the third intron of the AtELP4/ELO1 gene in Landsberg *erecta* (Ler) background (Nelissen et al., *PNAS* 102:7754-7759, 2005). As shown in FIG. 1(*a*), elo1-1/Atelp4 mutant plants supported significantly more pathogen growth than wild-type plants 3 days after infection with the bacterial strain *Pseudomonas syringae* pv. *maculicola* ("Psm") ES4326 (Davis et al., *Mol. Plant Microbe Interact* 4:477-488, 1991). To further confirm this result, a loss-of-function T-DNA insertion Atelp4 mutant in Columbia background (SALK_079193; Alonso et al., *Science* 301:653-657, 2003; *Arabidopsis* Biological Resource Center, Ohio State University, Columbus, Ohio, USA), which exhibits a similar morphological phenotype as other Elongator mutants (FIG. 1(*c*)), was also tested for its resistance to Psm ES4326 (FIG. 1(*b*)). This knockout mutant was also more susceptible to Psm ES4326 than the wild type, as measured by pathogen multiplication. These results demonstrate that ELP4 is a positive regulator of plant immunity and that the accessory subcomplex of Elongator contains functions in plant defense.

Example 2

Figure 2:
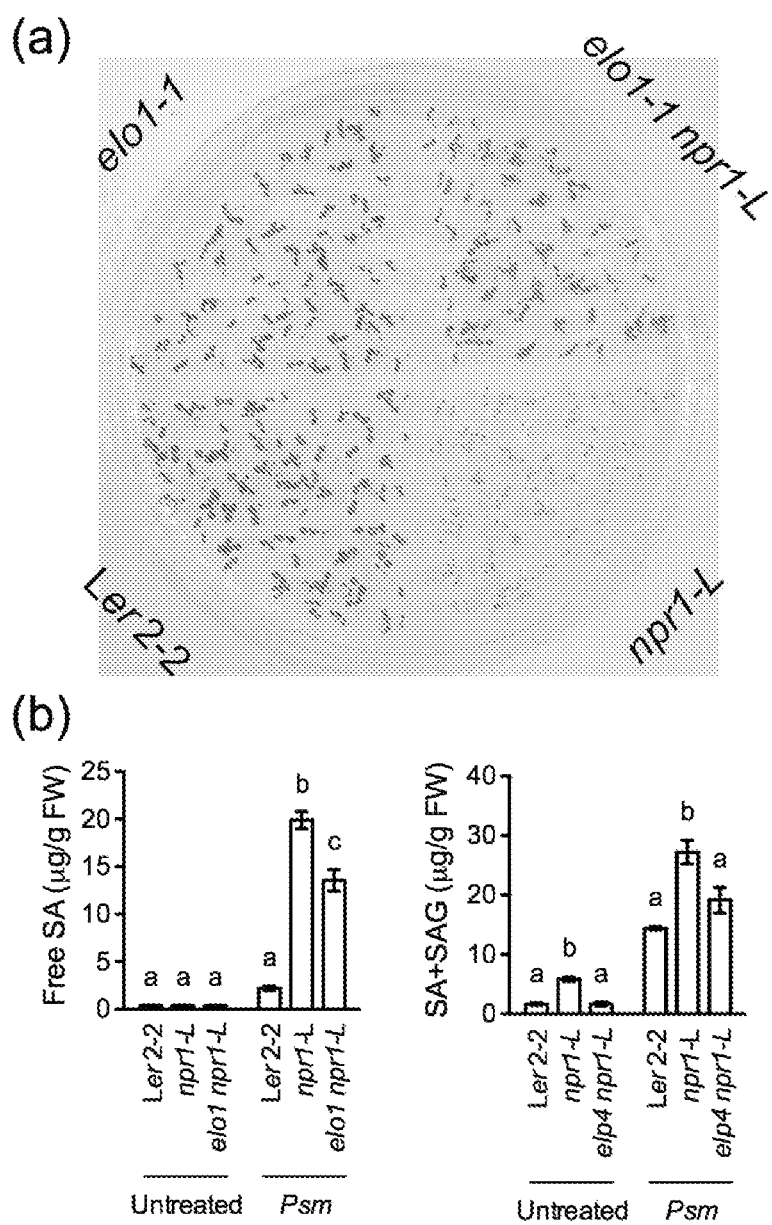
FIG. 2. (a): Germination and development of *Arabidopsis* seedlings on agar plates containing 0.5 mM added salicylic acid ("SA"). (b): Levels of free and total SA measured in control and mutant *Arabidopsis* lines, untreated or challenged with Psm ES4326. Different letter above the bars indicate significant difference ($p<0.05$, one-way ANOVA). The statistical comparisons were performed separately among Ler2-2, npr1-L, and elo1 npr1-L for each treatment.

The elo1-1 Mutation Restores SA Tolerance to npr1-L and Suppresses Hyperaccumulation of SA in npr1-L To examine the role of ELP4 in plant defense responses, including tolerance of seedlings to SA, an *Arabidopsis* double mutant was created via genetic cross between an elo1-1/Atelp4 line and npr1-L, which is a loss-of-function T-DNA insertion npr1 mutant in Ler background. As shown in FIG. 2(*a*), npr1-L seedling failed to develop beyond the cotyledon stage on media containing high concentrations (0.5 mM) of SA, which is consistent with previous studies (Cao et al. *Cell* 88:57-63, 1997; DeFraia et al., *Plant J.*

64:511-523, 2010, DeFraia et al., *BMC Plant Biol.* 13, 102, 2013; Kinkema et al., *Plant Cell* 12:2339-2350, 2000). In contrast, the elo1-1 npr1-L double mutant showed partial tolerance to the SA toxicity, suggesting that AtELP4 functions similarly as AtELP2 and AtELP3 in suppressing SA tolerance. SA levels in the elo1-1 npr1-L double mutant were measured and it was found that the presence of the elo1-1 mutation along with the npr1-L mutation reduced SA accumulation in npr1-L after Psm ES4326 infection, relative to the presence of npr1-L alone (FIG. 2(b)). Moreover, simultaneous removal of AtELP4 and NPR1 resulted in plants more susceptible to Psm ES4326 and also lacking resistance to two different ETI-inducing pathogens, *Pseudomonas syringae* pv. tomato (Pst) DC3000/avrRpt2 and Pst DC3000/avrRps4. Thus, AtELP4 has a role in plant defense phenotypes, demonstrating that the accessory subcomplex (ELP4-ELP6) of Elongator is essential for the function of the complete Elongator complex in plant immunity.

Example 3

The elo1-1 Mutation Genetically Interacts with eds1-2

Figure 3:
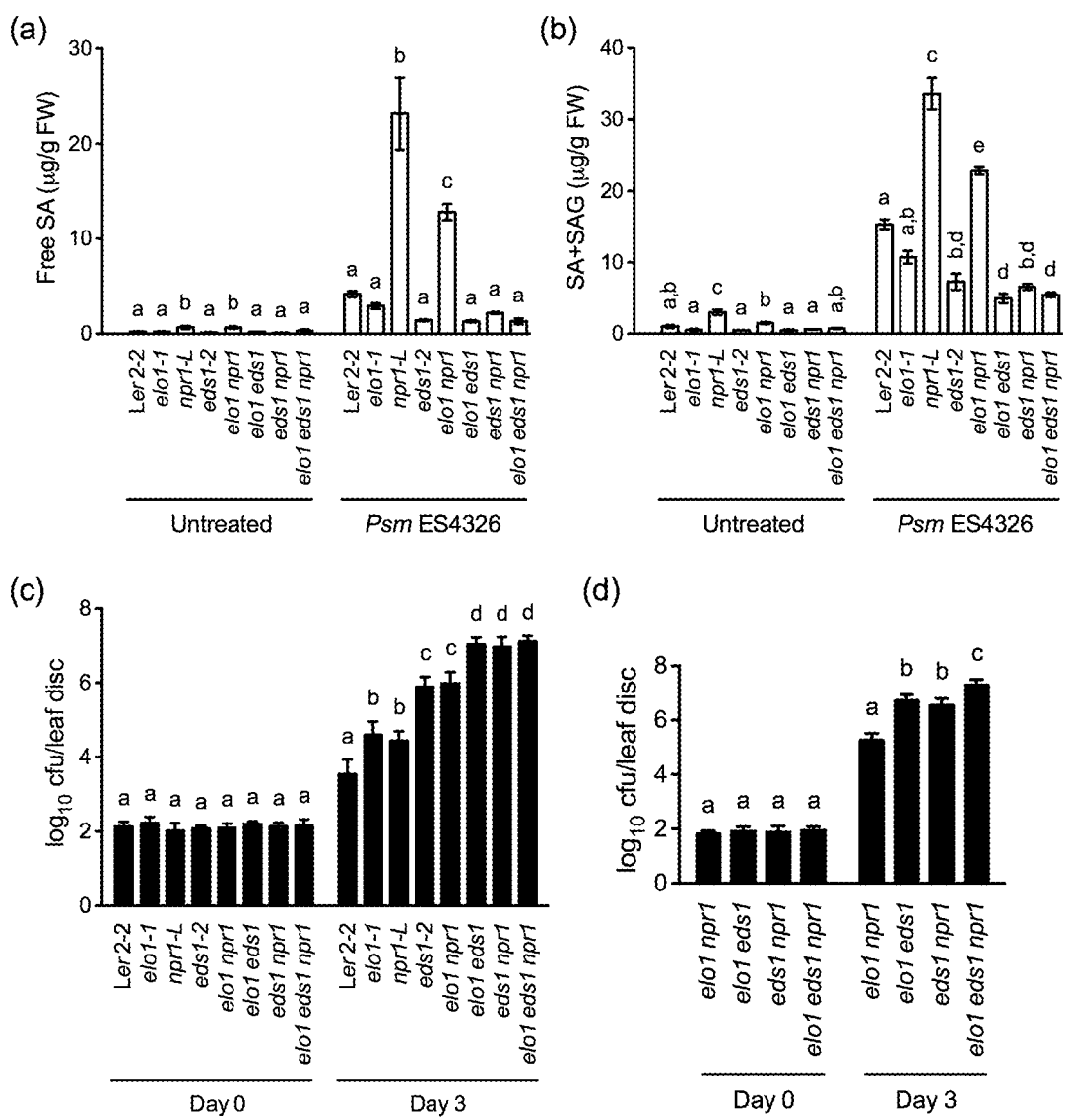
FIG. 3. (a-b): free SA and total SA (SA+SAG) levels in control and selected *Arabidopsis* mutant lines treated with or without Psm ES4326. (c-d): Bacterial multiplication ($\log_{10}$ CFU/leaf disc) in control and selected mutant *Arabidopsis* lines, 0 and 3 days after challenge with Psm ES4326. Different letter above the bars indicate significant difference ($p<0.05$, one-way ANOVA). The comparisons were performed separately for each treatment or time point.

EDS1 (ENHANCED DISEASE SUSCEPTIBILITY 1) is an essential regulator of basal resistance to (hemi)biotrophic pathogens by controlling defense amplification and the accumulation of the defense signaling molecule SA. Since Elongator also controls defense responses and regulates accumulation of SA, the genetic relationship between Elongator and EDS1 in plant immunity was studied. A double mutant *Arabidopsis* line, elo1-1 eds1-2, was created by a genetic cross in Ler background and pathogen-induced SA accumulation in elo1-1/Atelp4, eds1-2 and the double mutant elo1-1 eds1-2 was followed. As shown in FIG. 3(a), (b), the elo1-1 single mutant exhibited a small decrease in SA levels after pathogen infection. However, eds1 appears to be epistatic to npr1 since the npr1 eds1-2 double mutant did not differ from eds1-2 in pathogen-induced SA accumulation.

To investigate the relationship between Elongator and EDS1 in disease resistance, pathogen growth in elo1-1/Atelp4, eds1-2 and the double mutant elo1-1 eds1-2 was also examined. As shown in FIG. 3(c), (d), the elo1-1 mutation allowed for more pathogen growth in both the wild-type and eds1-2 backgrounds, indicating that elo1-1 and eds1-2 are largely independent and additive in contributing to disease susceptibility.

Example 4

Overexpression of AtELP4 Confers Disease Resistance

Figure 4:
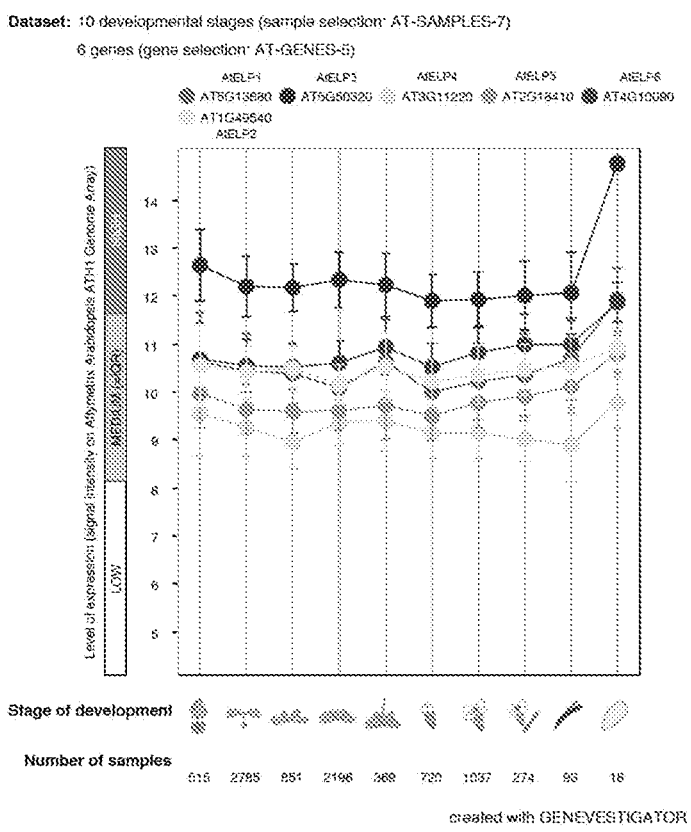
FIG. 4. (a): Expression levels of the six genes (AtELP1-AtELP6) encoding Elongator subunits at different developmental stages of *Arabidopsis*. (b): Leaf morphology of *Arabidopsis* control line Ler, an elo1-1 mutant, and complemented transgenic 35S::AtELP4-GFP elo1 and 35S::AtELP4 elo1 lines. (c): Bacterial multiplication ($\log_{10}$ CFU/leaf disc) of Psm ES4326 in control, indicated mutant *Arabidopsis* lines, and complemented transgenic 35S::AtELP4-GFP elo1 and 35S::AtELP4 elo1 lines, 0 and 3 days after challenge with ES4326. Different letter above the bars indicate significant difference ($p<0.05$, one-way ANOVA). The comparisons were performed separately for each time point. (d): Bacterial multiplication ($\log_{10}$ CFU/leaf disc) of Psm ES4326 in control (Ler2-2) and AtELP4-overexpressing lines. Different letter above the bars indicate significant difference ($p<0.05$, one-way ANOVA).
Figure 4:
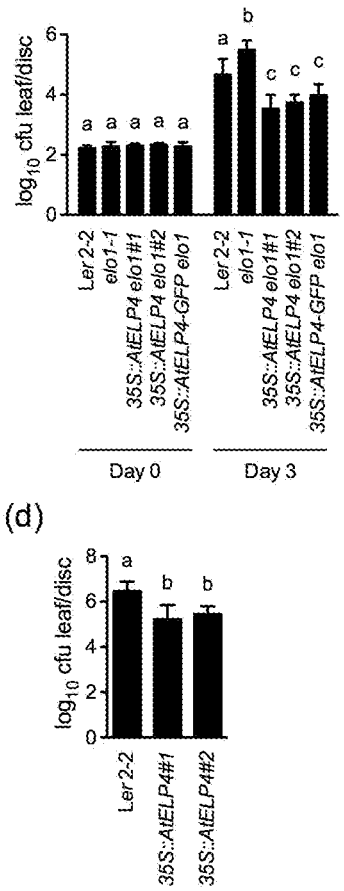
Figure 4:
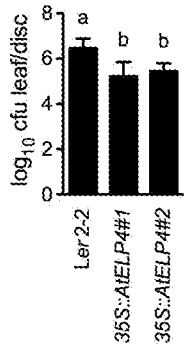
Figure 4:
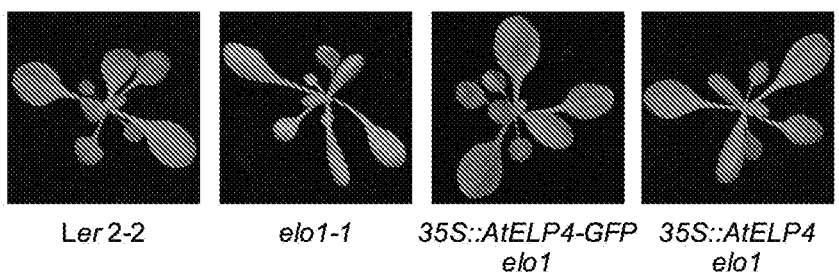

Transcriptome (mRNA abundance) analysis of the six ELP subunits based on signal intensity on the Affymetrix GeneChip® *Arabidopsis* ATH1 Genome Array (Affymetrix, Santa Clara, Calif., USA) using GENEVESTIGATOR (Zimmermann et al., *Plant Physiol.* 136:2621-2632, 2004) indicated that AtELP4 is the lowest expressed gene throughout plant life of the genes encoding the plant Elongator complex (FIG. 4(a)). This suggested that overexpression of ELP4 may result in a detectable phenotype. Therefore the effect of overexpression of AtELP4 on plant disease resistance was tested. The T-DNA vector pBI1.4T (Mindrinos et al., *Cell* 78:1089-1099) was utilized, which contains the neomycin phosphotransferase II (nptII) gene, conferring resistance to kanamycin for plant selection. The coding region of AtELP4 (SEQ ID NO:13) was amplified from cDNA using PCR, cloned into pBI1.4T and then transformed into the elo1-1/Atelp4 mutant plants using the *Agrobacterium* strain GV3101 following the floral-dip method (Clough and Bent, *Plant J.* 16:735-743). An AtELP4-GFP fusion gene was also transformed into the elo1-1/Atelp4 mutant plants. The AtELP4 coding sequence was cloned into the plasmid pRTL2-mGFP (von Arnim et al., *Gene* 221:35-43, 1998), which contains the cauliflower mosaic virus (CaMV) 35S promoter, a green fluorescent protein (GFP) gene and a CaMV 35S terminator. The 35S promoter-AtELP4-GFP-35S terminator cassette was cloned into the T-DNA vector pCB302 (Xiang et al., *Plant Mol. Biol.* 40:711-717, 1999), which confers resistance to Basta for plant selection, and then transformed into the elo1-1/Atelp4 mutant plants using the *Agrobacterium* strain GV3101 following the floral-dip method (Clough and Bent, *Plant J.* 16:735-743). Both transgenes AtELP4/ELO1 and AtELP4/ELO1-GFP complemented the mutant morphology of the elo1-1/Atelp4 mutant (FIG. 4(b)). Two independent 35::AtELP4 lines with high AtELP4 expression and one 35S::AtELP4-GFP were selected and their homozygous progenies containing a single insert were used for further experiments (FIG. 4). No spontaneous lesion formation was observed in these lines. Resistance of *Arabidopsis* to bacterial pathogen Psm ES4326 was tested. Three days after infection, transgenic lines exhibited significantly enhanced resistance to Psm ES4326 as compared to wild-type plants (FIG. 4(c), (d)) as determined by multiplication of bacteria in infected leaves.

Example 5

Overexpression of AtELP4 leads to constitutive activation of SA signaling

Elongator associates with elongating RNAP II and positively regulates transcription. In order to understand the mechanism underlying enhanced disease resistance in AtELP4 overexpressing plants, microarray analysis was performed to investigate global transcriptional profiling changes in AtELP4 overexpressing plants. Triplicate experiments were performed independently, and the data were analyzed to identify genes that were differentially expressed between 35S::AtELP4 line #1 and the wild type. q-values were used to identify differentially expressed candidate genes. It was found that overexpressing AtELP4 had a significant impact on the expression levels of genes involved in the SA signaling pathway (Table 1).

TABLE 1

Defense genes that are differentially expressed between 35S:AtELP4 and wild-type Ler plants.

| AGI Locus | Gene Name | 35S::AtELP4/Ler Log$_2$ (FC) | q Value | AGI Description |
|---|---|---|---|---|
| At3g11220 | ELO1 | 5.54 | 0 | ELONGATA 1/Elongator subunit 4 |
| At1g02450 | NIMIN1 | 1.089 | 0 | NIM-INTERACTING 1 |
| At3g25882 | NIMIN2 | 1.593 | 0.0001 | NIM-INTERACTING 2 |
| At4g39030 | EDS5 | 1.301 | 0 | ENHANCED DISEASE SUSCEPTIBILITY 5 |
| At5g13320 | PBS3 | 2.345 | 0.0001 | AVRPPHB SUSCEPTIBLE 3 |
| At3g52430 | PAD4 | 1.145 | 0 | PHYTOALEXIN DEFICIENT 4 |
| At4g14400 | ACD6 | 1.122 | 0 | ACCELERATED CELL DEATH 6 |
| At2g13810 | ALD1 | 1.265 | 0.0005 | AGD2-LIKE DEFENSE RESPONSE PROTEIN 1 |
| At1g19250 | FMO1 | 4.168 | 0 | FLAVIN_DEPENDENT MOMOOXYGENASE 1 |
| At2g14610 | PR1 | 2.251 | 0 | PATHOGENESIS-RELATED GENE 1 |
| At3g57260 | PR2 | 2.122 | 0.0007 | PATHOGENESIS-RELATED GENE 2 |
| At1g75040 | PR5 | 2.652 | 0.0010 | PATHOGENESIS-RELATED GENE 5 |
| At4g31800 | WRKY18 | 1.252 | 0 | WRKY DNA-binding protein 18 |
| At5g22570 | WRKY38 | 1.374 | 0.0002 | WRKY DNA-binding protein 38 |
| At2g04450 | NUDT6 | 2.348 | 0 | NUDIX HYDROLASE HOMOLOG 6 |
| At4g12720 | NUDT7 | 1.103 | 0 | NUDIX HYDROLASE HOMOLOG 7 |
| At2g19190 | FRK1 | 1.613 | 0 | FLG22-INDUCED RECEPTOR-LIKE KINASE 1 |
| At1g45145 | TRX5 | 1.361 | 0 | THIOREDOXIN H-TYPE 5 |

To ensure validity of the microarray data, the expression levels of pathogenesis-related genes (PR1, PR2, and PR5) in the AtELP4 overexpressing plants were investigated further by RT-qPCR. It was found that PR1, PR2, and PR5 mRNAs were constitutively activated in 35S::AtELP4 plants, further confirming the microarray data.

Figure 5:
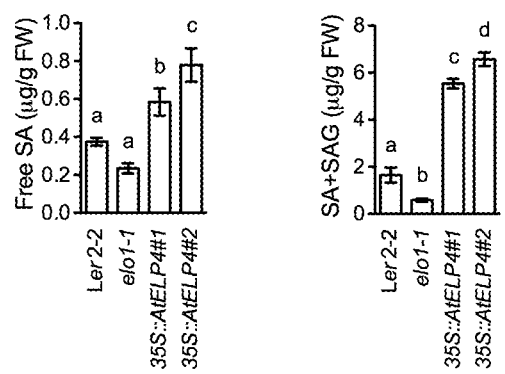
FIG. 5. Free SA and total SA (SA+SAG) levels (μg/g FW) in *Arabidopsis* control, elo1-1 mutant, and 35S::AtELP4 transgenic lines. Different letter above the bars indicate significant difference ($p<0.05$, one-way ANOVA).

To determine the possible link in SA levels to the activated defense phenotype observed in 35S::AtELP4 plants, we measured the SA levels using HPLC. As shown in FIG. 5, the endogenous SA levels in 35S::AtELP4 plants were elevated in comparison with those in the wild type. Taken together, our observations suggest that overexpressing AtELP4 contributes to disease resistance by constitutively activating SA-related defense signaling.

Example 6

Figure 6:
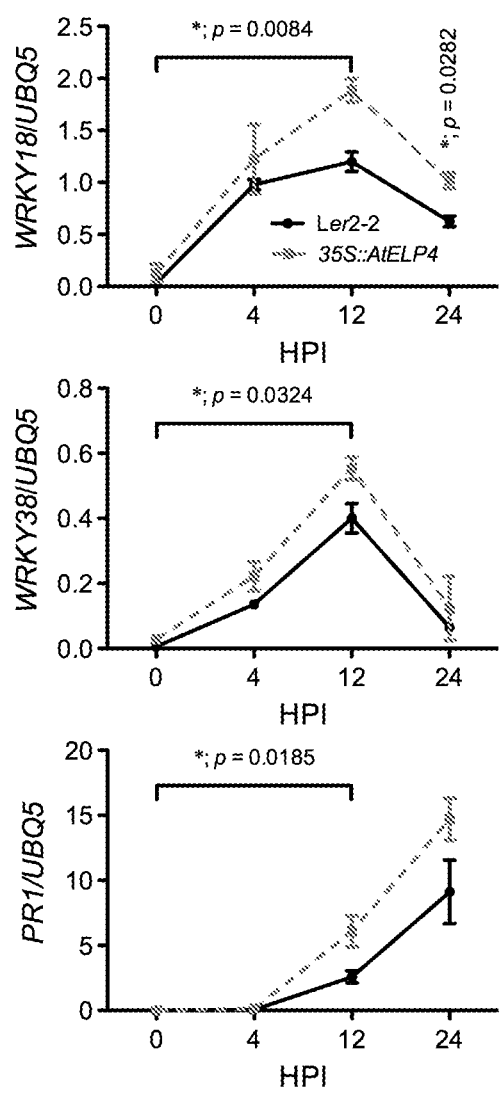
FIG. 6. Time course of induction of selected defense genes in *Arabidopsis* Ler and a 35S::AtELP4 transgenic line following challenge with Psm ES4326. Asterisks indicate significant difference between the induction of defense genes in Ler2-2 and 35S::AtELP4 plants at the indicated time points compared to time 0 ($p<0.05$, two-way ANOVA). HPI: hour post-inoculation.

Induction of Defense Genes after Psm ES4326 Infection is Stronger and Faster in AtELP4-Overexpressing Plants The speed of pathogen-induced transcriptional reprogramming in plants is a determining factor of plant defense. Previous studies showed that disruption of Elongator results in delayed and/or decreased induction of a group of defense genes compared to wild type during pathogen infection, suggesting that the plant Elongator complex may serve as an accelerator in plant immunity (DeFraia et al., Plant J. 64:511-523, 2010, DeFraia et al., BMC Plant Biol. 13, 102, 2013; Wang et al., Plant Cell 25:762-776, 2013). To investigate whether overexpression of the Elongator complex can accelerate the induction of defense genes, a time course experiment was performed to monitor the induction kinetics of PR genes during the infection of the virulent pathogen Psm ES4326 in 35S::AtELP4 transgenic plants. Similarly to Atelp2 and Atelp3, elo1/Atelp4 plants exhibited a delayed induction of PR1, PR2, and PR5 compared to the wild type during Psm ES4326 infection. In contrast, induction of the defense genes WRKY18, WRKY38, and PR1 is stronger and faster in AtELP4 overexpressing plants (FIG. 6). These results show that Elongator affects the speed and amplitude of defense gene induction during Psm ES4326 infection, explaining the enhanced defense phenotype in AtELP4 overexpressing plants.

Example 7

Materials and Methods for Construction and Testing of Transgenic Strawberry Plants A. Plasmid Construction and Plant Transformation The Gateway® T-DNA vector pK7WG2D.1 (Life Technologies, Grand Island, N.Y., USA) was utilized, which contains the neomycin phosphotransferase II (nptII) gene, conferring resistance to kanamycin for plant selection, and the enhanced green fluorescent protein (GFP) for visual selection (Karimi et al. Trends Plant Sci. 7:193-195, 2002). The coding regions of AtELP3 and AtELP4 were amplified from cDNA using PCR, cloned into pK7WG2D,1 and then transformed into the diploid strawberry Fragaria vesca L. using the Agrobacterium strain GV3101. Leaf explants of F. vesca accession 'Hawaii-4' were transformed using a regeneration protocol (Oosumi et al. Planta 223:1219-1230, 2006) optimized by Silva et al. Transgenic Res. 1-12, doi: 10.1007/s11248-015-9869-5, 2015). Transgenic calli and shoots were visually screened for GFP six weeks after co-culture, and well-developed and rooted shoots were transplanted into soil and placed in a growth chamber with a 12 hour photoperiod. The plants were considered to be independent transgenic lines when regenerated from independent calli. 'Hawaii-4' seedlings, also derived through leaf regeneration, were used as a control in all experiments of the study. Plants were propagated by runners, and watered and fertilized as needed. Pesticides were applied as necessary to control insects and mites. After two months of growth in soil, well-developed plants were used in the experiments.

B. Salicylic Acid Measurement

Basal levels of total and free SA were quantified. For free SA accumulation after pathogen challenge, transgenic strawberry lines and the control were inoculated with *C. gloeosporioides* (see below), and leaf samples were collected 24 hours after infection. SA content in strawberry leaf tissues was measured by HPLC as described by Verberne et al. *Phytochemical Anal.*, 13:45-50, 2002).

C. Assessment of Disease Resistance

To evaluate the effect of AtELP3 and AtELP4 on disease resistance, the pathogens *Colletotrichum gloeosporioides*, *Podosphaera aphanis* and *Xanthomonas fragariae*, causal agents of strawberry crown rot, powdery mildew and angular leaf spot, respectively, were utilized.

Three isolates of the hemibiotrophic pathogen *C. gloeosporioides* (CG #13-01, GG #98-285 and CG #97-15A) were obtained from diseased strawberry crowns. Colonies were maintained on Potato-dextrose-agar (PDA) for 6 to 8 d at 24° C. Conidial suspension and plant inoculation was performed according to Silva et al., 2015, ibid. Incidence of Anthracnose crown rot was scored as the number of individual plants collapsed at 20 dpi. Disease incidence (DI) was also assessed every 2 d, allowing the calculation of the area under the disease progress curve (AUDPC) (Shaner and Finney, *Phytopathol.* 67:1051-1066, 1977):

$$AUDPC = \sum_{i=1}^{Ni-1} \frac{(y_i + y_{i+1})}{2}(t_{i+1} - t_i),$$

where $N_i$ is number of assessments; $(y_i + y_{i+1})$ is the sum of initial and consecutive disease incidence; and $(t_{i+1} - t_i)$ is time interval between two consecutive assessments. The experiment was conducted three times with five plants per strawberry line each time.

Powdery mildew inoculum was originally obtained from strawberry cv. 'Festival' (*Fragaria×ananasa* Duch.) and identified as *Podosphaera aphanis* based on the examination of conidiophores and/or chasmothecia detected on leaves surface. Selected inoculum (PM #15-31) was used to infect non-transformed *F. vesca* accession Hawaii-4. Inoculated plants were kept in growth chamber for 8 days at 80% RH and 22° C. After incubation, plants were assigned disease reaction (DR) scores according to the method described (Göllner et al., *New Phytol.* 177:725-742, 2008), where a DR score of 2 describes fully susceptible plants, indicating that extensive pathogen growth was observed; a DR score of 0 refers to fully resistant plants, on which no fungal structure and disease symptoms could be observed; and a DR score of 1 denotes plants with intermediate susceptibility, which show fungal structure on less than 10% of the leaf surface. At the end of the experiment, three samples of approximately 500 mg of leaves were harvested per genotype for spore count according to the methodology described by Silva et al., 2015, ibid. Spore counts were normalized to the initial sample weight. The experiment was done with five plants per line each time, and repeated three times with similar results.

The bacterial pathogen *X. fragariae* (XF #11-15) was initially isolated from leaves of strawberry 'Festival' and kept on solid sucrose peptone agar (SPA) (5% peptone, 0.5% $K_2HPO_4$, 0.25% $MgSO_4.7H_2O$, 10% sucrose and 18% agar) at ±29° C. for 4 d. Suspension preparation and inoculation were performed according to Silva et al., 2015, ibid., adapted from Maas et al., *HortSci.* 35:4, 2000).

Inoculation sites were evaluated and rated at the end of the fourth week using the following scale: 0=no reaction, transient water-soaking from inoculation no longer evident; 1=transient water-soaking evident in the inoculation site; 2=slight chlorosis or necrosis in the center of the inoculation site; 3=water-soaking expanding beyond inoculation site and often bacterial exudate evident; 4=necrosis spreading beyond the inoculation site and/or secondary infections evident; and 5=total necrosis of the inoculation area and leaflet changing color from chlorosis to reddish-brown. Plants were considered susceptible on a whole-plant basis if bacterial exudate was produced at any inoculation site, if inoculation sites remained translucent, or if secondary infection sites were apparent on inoculated leaves. Plants were considered resistant if inoculation sites lost translucency and/or developed necrotic centers that did not progress beyond inoculation sites. At the end of the test, inoculation sites were cut from the leaves, surface sterilized, ground in 1 mL of sterile water, vortexed, and serially diluted. The dilutions were transferred onto SPA in culture plates. Plates were incubated at room temperature for development of colonies of *X. fragariae* (Roberts et al., *Plant Dis.* 80:1283-1288, 1996). The number of CFU/mL was calculated following the incubation of the plates for 6 d at RT.

All isolates used in these experiments were obtained from plants growing in greenhouses or strawberry fields located in west-central Florida. *X. fragariae* and *C. gloeosporioides* isolates were stored at -80° C. in 20% glycerol, and *P. aphanis* accession was stored at the Herbarium and Culture Collection of Gulf Coast Research and Education Center (GCREC)—University of Florida.

D. Gene Expression

Total DNA and RNA were extracted from strawberry leaves (~100 mg) of transgenic lines and the control. In order to verify the presence of the full length of the plasmid, the AtELP3 and AtELP4 genes were amplified by PCR (94° C. for 5 min, 35 cycles: 94° C. for 3 min, 65° C. for 1 min, 72° C. for 2 min, and hold at 72° C. for 10 min) using AtELP3F and AtELP3R, and AtELP4F and AtELP4R primers. Strawberry genomic DNA was extracted from leaves using a CTAB method optimized for strawberry (Brunings et al., *Euphytica* 173:63-75, 2010; Chang et al., *Plant Mol. Biol. Rep.* 11:113-116, 1993). RNA was extracted using an RNeasy® Plant Mini-Kit (Qiagen, Valencia, Calif., USA) following the manufacture's instruction. Leaves samples were taken at 0, 24, 48 and 72 h after inoculated with *C. gloeosporioides*. One µg RNA was reverse transcribed using the Improm-II Reverse Transcriptase (Promega Inc., Madison, Wis.). Reverse transcription and real-time quantitative PCR (qPCR) was performed using the StepOne Plus system (Applied Biosystems, USA) based on SYBR Green chemistry. All qPCR primers were designed with the Primer Express 2.0 software (Applied Biosystems, USA). The relative mRNA levels of AtELP3, AtELP4, FvPR1, FvPR2 and FvNPR5 were expressed in relation to the strawberry elongation factor-1-alpha (EF1α) gene, and calculated using the $2^{-\Delta CT}$ method (Livak and Schmittgen, *Methods* 25:402-408, 2001; Sehringer et al., *Anal. Bioanal. Chem.* 383:768-775, 2005).

E. Statistical Analysis.

Statistical analysis was performed using GraphPad Prism® software (GraphPad, San Diego, Calif., USA) by one-way or two-way analysis of variance (ANOVA), or by Student's t test analysis. All experiments were performed three times with similar results.

Example 8

AtELP3 and AtELP4 Expression and Plant Development

A total of 30 AtELP3 and 20 AtELP4 transgenic strawberry plants ("E3" and "E4" plants) were generated and analyzed by PCR. Ten and nine strawberry plants containing the full-length AtELP3 and AtELP4 transgene were selected, respectively. Total RNA was extracted from leaves of six-month-old plants and subjected to RT-qPCR analysis to examine the expression of AtELP3 and AtELP4. Results showed that the transgene was expressed at different levels in the transgenic plants (FIG. 7(a), (b)).

Figure 7:
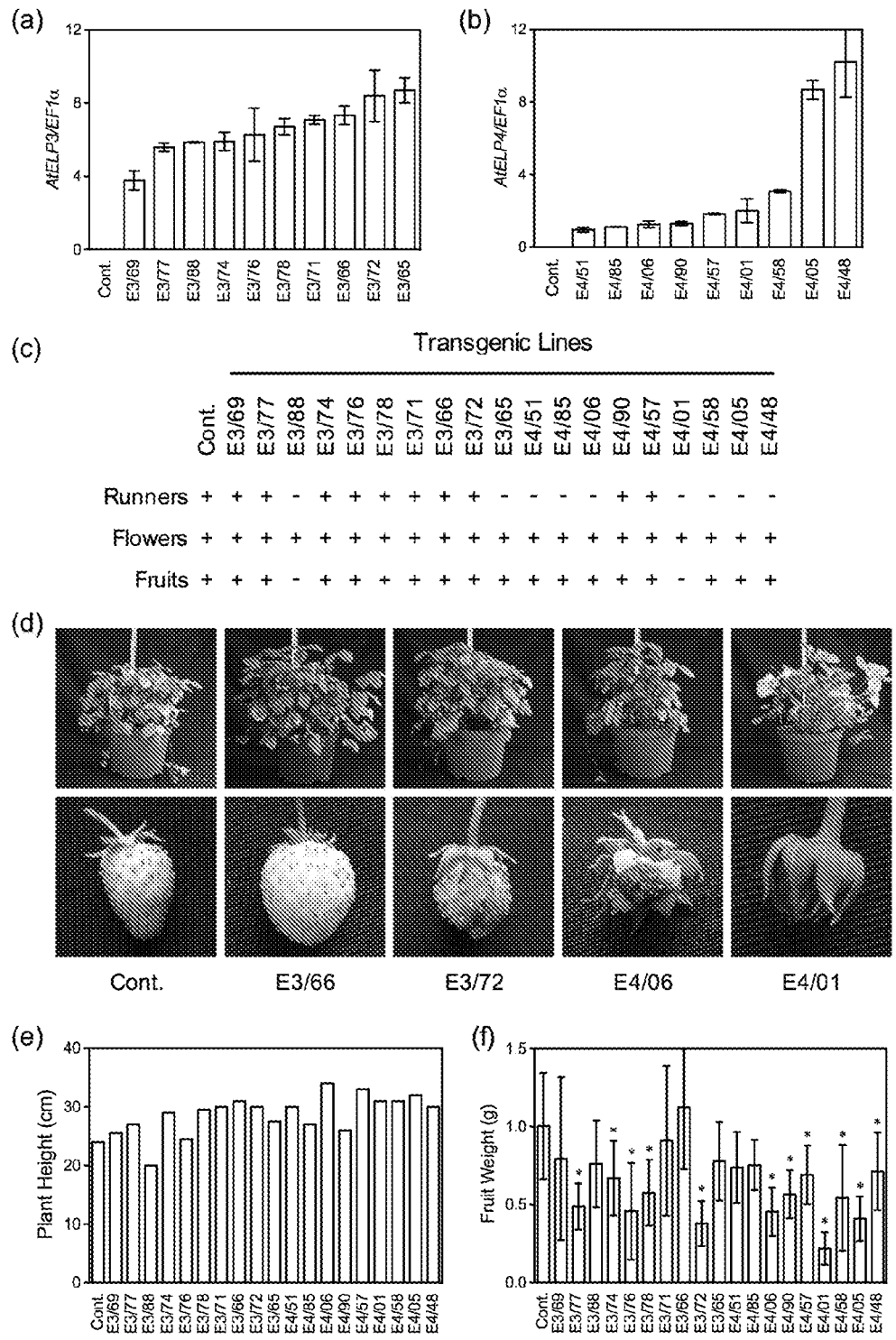
FIG. 7. Developmental phenotypes of transgenic strawberry plants expressing AtELP3 or AtELP4. (a to b): qPCR analyses of the expression levels of AtELP3 and AtELP4 in independent AtELP3- and AtELP4-transgenic lines, respectively. Almost no expression was observed in the wild type strawberry Hawaii-4 (cont.). The order of the transgenic lines is presented in order of increasing expression levels of the transgenes. The EF1α gene was used as an internal control. Gene expression data represent the average of three biological replicates with standard deviation ("SD"). (c): Presence (+) or absence (−) of runners, flowers, and fruits on the transgenic plants. The order of the transgenic lines is the same as in FIG. 7(a), (b). (d): Plant (top) and fruit (bottom) morphology of two AtELP3-expressing (E3/66 and E3/72) and two AtELP4-expressing (E4/06 and E4/01) independent transgenic lines, and the control Hawaii-4 (Cont.). (e): Plant height (cm) and (f): Fruit weight of one-year-old control and transgenic plants overexpressing AtELP3 or AtELP4. Fruit weight data represent the average of 20 replicates with SD. Asterisks indicate significant difference between the transgenic lines and the control ($p<0.05$, Student's t test).

In general, E3-plants presented regular canopy, and E4-plants showed elongated and less dense canopy (FIG. 7(d)). Excepting lines E3/69 and E3/76, which did not differ from control, and E3/88, the shortest plant in the set, all transgenic plants were higher (FIG. 7(e)), and most plants produced fruits significantly smaller compared to the control (FIG. 7(f)). Whereas all transgenic lines formed flowers, one E3-plant (line E3/88) and two E4-plants (line E4/01 and E4/06) had aborted or irregular fruits (FIG. 7(c), (d)). Altered runner development was sometimes observed. Most of E4-plants did not grow runners, except for lines E4/57 and E4/90 that presented low transgene expression (FIG. 7(b)), whereas only two E3-plants did not grow runners (lines E3/65 and E3/88). Although not correlated to transcript levels, the presence of the AtELP3 and AtELP4 transgenes may affect growth and development in strawberry plants.

Example 9

Disease Resistance of Transgenic Strawberry Plants

A. Anthracnose Crown Rot Resistance

Figure 8:
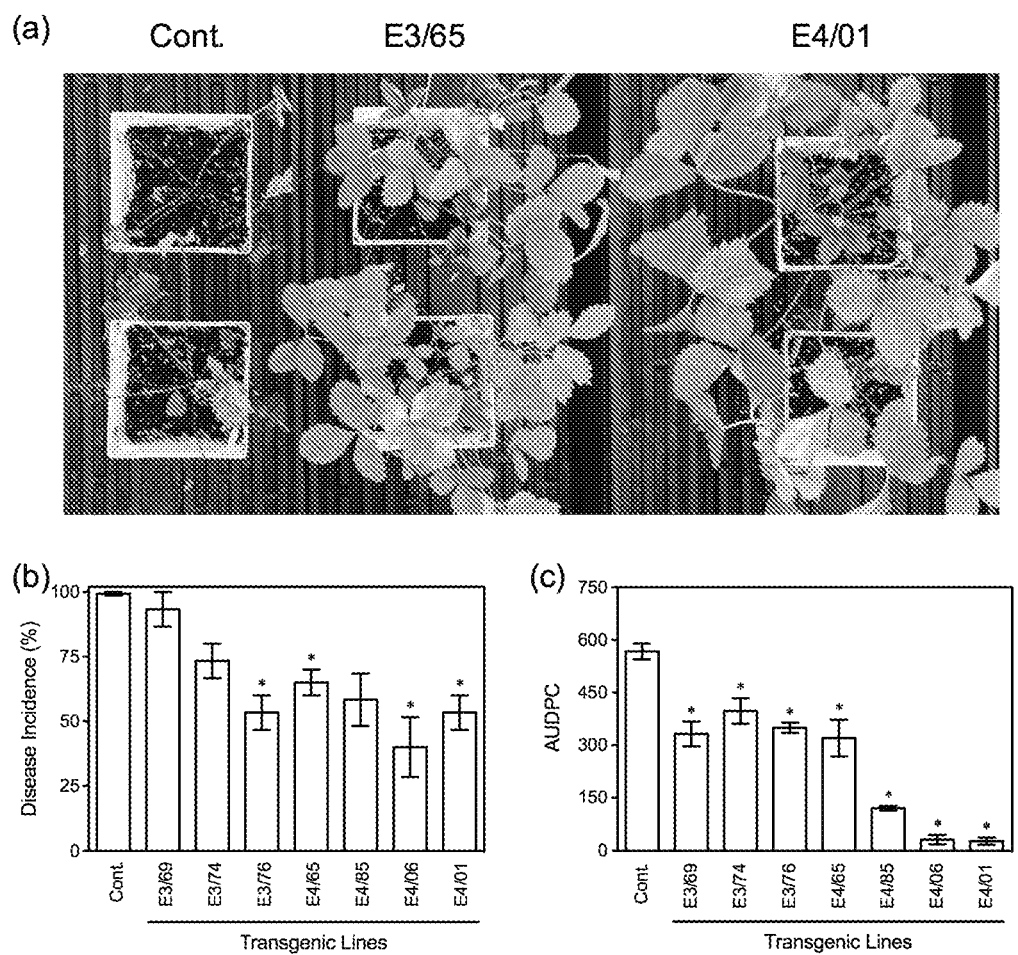
FIG. 8. Resistance of AtELP- and AtELP4-transgenic strawberry plants to anthracnose crown rot. (a): Disease symptoms caused by *Colletotrichum gloeosporioides* on the control (Cont.) and the transgenic lines E3/65 and E4/01. Photos were taken 20 days after infection ("dai"). (b): Disease Incidence ("DI") and (c): Area under the disease progress curve ("AUDPC") for the control (Cont.) and AtELP3- and AtELP4-transgenic lines infected with *C. gloeosporioides*. Data represent the average of collapsed plants in three independent experiments containing 5 plants each, with SD. DI allowed the calculation of AUDPC. Asterisks indicate significant difference between the transgenic lines and the control ($p<0.05$, Student's t test).

Crown rot symptoms, characterized by initial signs of water stress and subsequently collapse, were observed 5 days after infection on control plants. These plants had their tissue aggressively invaded and collapsed before 20 dpi, whereas transgenic plants displayed reduced symptoms (FIG. 8(a)). Disease Incidence (DI) was lower in E3- and E4-transgenic lines presenting higher transgene levels (FIG. 8(b)). E4/06 presented the lowest percentage of collapsed plants (40%) compared to the control. Resistance to *C. gloeosporioides* was also reflected by AUDPC results (FIG. 8(c)). AUDPC of all tested lines were significantly reduced compared to the non-transgenic plants, with E4-lines displaying the best results (lower AUDPC ranging from 75% to 98% compared to the control).

B. Powdery Mildew Resistance

Figure 9:
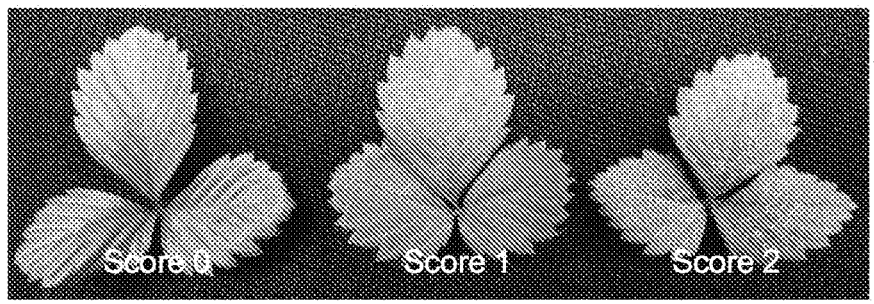
FIG. 9. Resistance of AtELP3 and AtELP4 transgenic strawberry plants to powdery mildew. (a): Phenotype of disease reaction scores ("DS") for leaves inoculated with *P. aphanis*. Scores 0=resistant, Score 1=intermediate susceptibility, and Score 2=susceptible. (b): Disease scores (DS). Data represent the average of five biological replicates with SD. (c): *P. aphanis* spores count score for the control (Cont.) and AtELP3- and AtELP4-transgenic lines. Spores were counted 10 days after inoculation. FW: fresh weight. Data represent the average of 15 biological replicates with SD. Asterisks indicate significant difference between the transgenic lines and the control ($p<0.05$, Student's t test).
Figure 9:
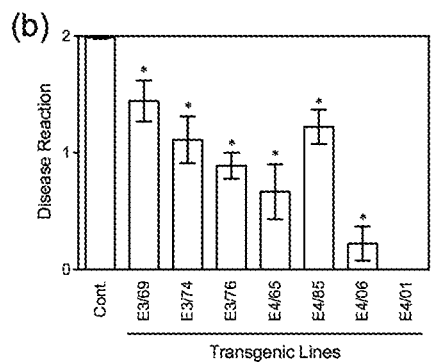
Figure 9:
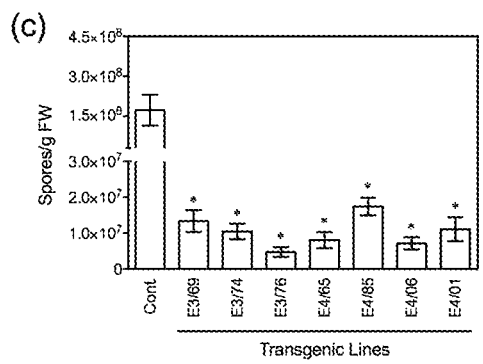

Eight days following fungal inoculation, leaves from transgenic plants were slightly affected while those from control showed vigorous patches of white powdery fungus, showing a DS score=2 (FIG. 9(a)). Little mycelium was produced on lines E3/76, E3/65 and E4/06 (Mean DR score=1; FIG. 9(a), (b)), and no visible symptoms were observed in the transgenic line E4/01 (Mean DR score=0; FIG. 9(a), (b)), demonstrating enhanced resistance to *P. aphanis* in these lines. The number of spores was also drastically reduced on strawberry transgenic lines, being significantly different from the control (FIG. 9(c)). Reductions from 89.9% (E4/85) up to 95.5% (E3/76) were observed and the high expression lines were clearly more resistant. These results suggest that the signs and symptoms, and the susceptibility to the pathogen decrease with the increase of transgene expression for both studied genes, and E4-lines were more resistant to powdery mildew.

C. Angular Leaf Spot Resistance

Figure 10:
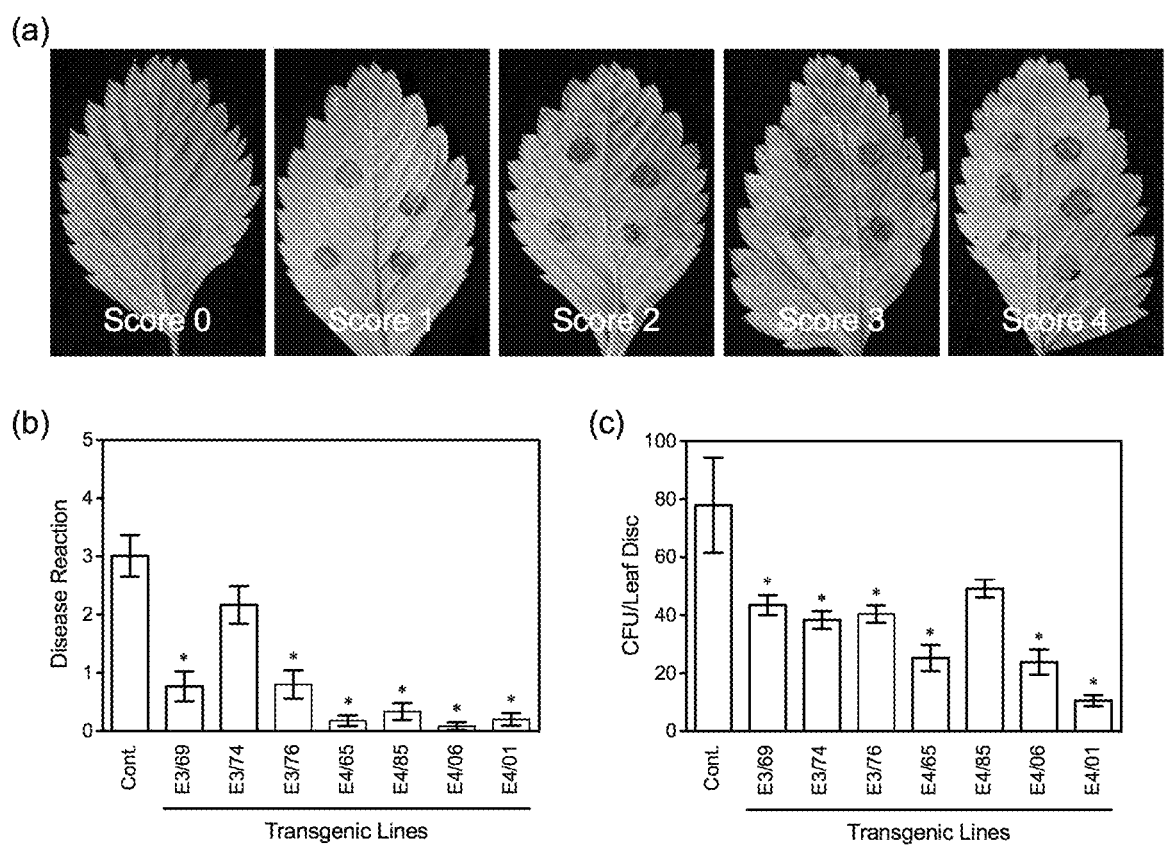
FIG. 10. Resistance of AtELP3 and AtELP4 transgenic strawberry plants to angular leaf spot. (a): Phenotype of disease reaction scores (DS) on leaves of transgenic and wild type strawberry Hawaii-4 (Cont.) plants inoculated with *Xanthomonas fragariae*. Score 0: transient water-soaking from inoculation no longer evident; Score 1: transient water-soaking evident; Score 2: slight chlorosis or necrosis in the center of the inoculation site; Score 3: water-soaking expanding beyond inoculation site with bacterial exudate often evident; and score 4: necrosis spreading beyond the inoculation site and/or secondary infection evident. (b): Disease Reaction scores (DS) of angular leaf spot, and (c): Colony-forming unit (CFU) of *X. fragariae* in the control (Cont.) and AtELP3 and AtELP4 transgenic lines. Data represent the mean of 15 independent samples (inoculation sites) with SD. Asterisks indicate significant difference between the transgenic lines and the control ($p<0.05$, Student's t test).

AtELP3- and AtELP4-expressing lines were tested for their resistance to angular leaf spot. At 7 dpi control plants showed water-soaking lesions still evident (Score 1) that eventually expanded beyond inoculation site and exposed bacterial exudate (Score 3) (FIG. 10(a)). At the end of the experiment, no plants showed symptoms of total necrosis, chlorosis, and/or secondary infections. However, control plants exhibited the highest DR scores, and E3/74 developed slight necrosis in the center of the inoculation site, being also described as susceptible (FIG. 10(a)). E3/65 and E4-lines were considered resistant to *X. fragariae* (FIG. 10(b)) as their inoculation sites lost translucency and did not develop any other symptoms (Score 0). Bacterial populations were also determined by colony counts of each inoculated area. As shown in FIG. 10(c), with exception of E4/85, the bacterial populations were significantly decreased in all tested lines. Highest disease resistance was observed in lines E3/65, E4/06 and E4/01. These results demonstrate that overexpression of AtELP3 and AtELP4 in strawberry enhances resistance to the bacterial pathogen *X. fragariae*.

D. Salicylic Acid Accumulation in Transgenic Strawberry

Figure 11:
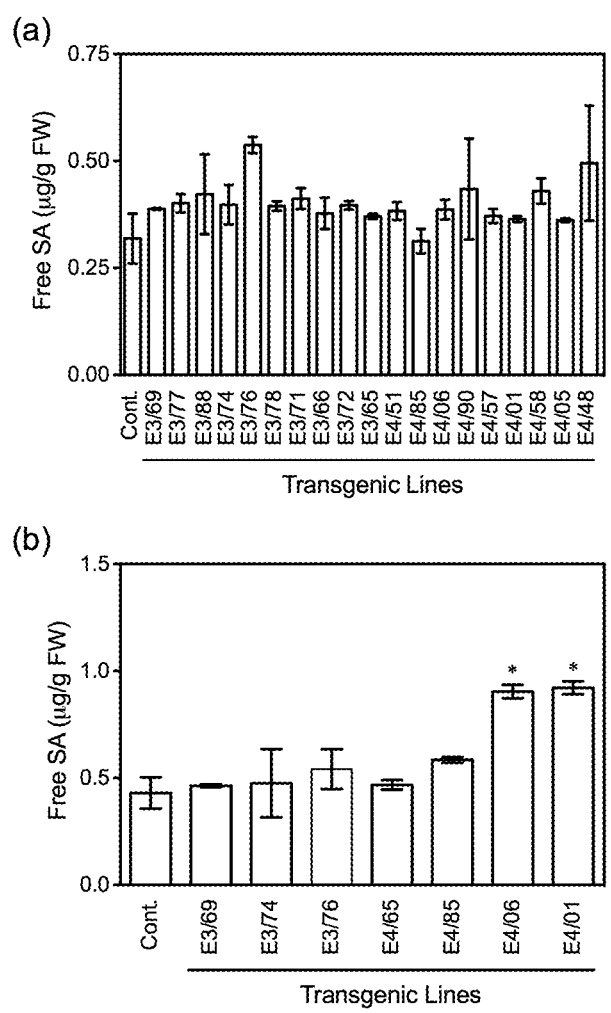
FIG. 11. Free SA levels in AtELP3 and AtELP4 transgenic strawberry plants before and after pathogen inoculation. (a): Free SA in the AtELP3 and AtELP4 transgenic plants and the control (Cont.). AtELP3 and AtELP4 expression did not alter the basal level of free SA in transgenic plants. (b): Free SA levels 24 h after *C. gloeosporioides* inoculation. SA levels were measured by HPLC. Data represent the average of three biological replicates with SD. Asterisks indicate significant difference between the transgenic line and the control ($p<0.05$, Student's t test).

The effect of ectopic expression of AtELP3 and AtELP4 on SA accumulation in strawberry was also tested. Basal levels of free SA in transgenic plants, and the accumulation of free SA 24 hours after pathogen challenge were determined. Ectopic expression of AtELP3 and AtELP4 in strawberry did not change basal levels of free SA (FIG. 10(a)); however, significant accumulation of free SA was observed in transgenic lines E4/06 and E4/01 (FIG. 11(b)).

Example 10

Disease Resistance of Transgenic Tomato Plants

Generation of Transgenic Tomato Plants

The T-DNA plasmid pK7WG2D,1-AtELP4 was also used for production of transgenic tomato plants. The AtELP4 gene was transformed into the tomato cultivar 'Moneymaker' using the *Agrobacterium* strain GV3010. The genetic transformation was conducted by the University of Nebraska's Plant Transformation Core Research Facility. A total of 25 independent transgenic R1 lines were generated and 10 single T-DNA insertion homozygous lines were identified in the R2 and R3 generations. These homozygous lines were used for the disease resistance test.

Disease Resistance Test

One-month-old AtELP4 transgenic plants and the control 'Moneymaker' plants were spray-inoculated with a suspension of the bacterial pathogen *P. syringae* pv. tomato (Pst) DC3000 in 10 mM $MgCl_2$ ($OD_{600}$=0.3). Pst DC3000 causes tomato bacterial speck disease. After inoculation, the plants were covered with plastic bags for 36 hours. Pathogen growth inside the plants was determined by collecting leaf tissues at different time points (day 0, 3, 6, and 9), grinding the tissue in 10 mM $MgCl_2$, plating the suspension on growth medium, and counting the colonies. The experiment was repeated four times.

Bacterial Speck Resistance

Figure 12:
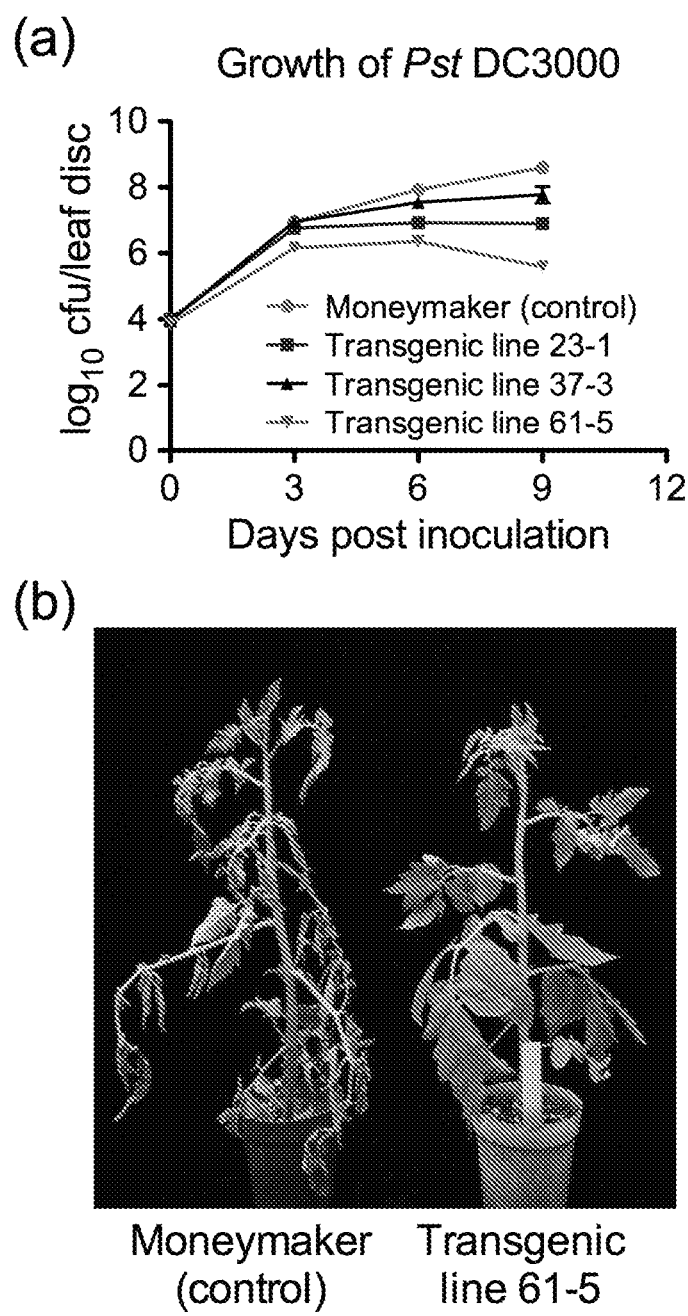
FIG. 12. Growth of bacteria and symptomotology of Bacterial Speck on tomato plants. (a): growth curve days, post-inoculation, of *P. syringae* pv. tomato DC3000 in tomato cv. Moneymaker and representative transgenic lines; (b): symptom expression on inoculated control and transgenic plants, six days post inoculation.

Out of the 10 independent transgenic homozygous lines, three lines (23-1, 37-3, and 61-5) exhibited enhanced resistance to Pst DC3000 (FIG. 12(a)). At nine days post inoculation, the bacterial titer in the most resistant AtELP4 transgenic line 61-5 was 50 fold less than that in the control 'Moneymaker' plants. Consistently, while the control plants were significantly damaged by the bacterial pathogens, as indicated by the burning of leaves on the control plant in FIG. 12(b), plants of the exemplary transgenic line 61-5 stayed mildly affected. The photo in FIG. 12 (b) was taken six days post inoculation. These results demonstrate that overexpression of AtELP4 in tomato increases resistance to the bacterial pathogen Pst DC3000.

What is claimed is:

1. A transgenic strawberry or tomato plant comprising a heterologous nucleic acid sequence that encodes an ELP4 polypeptide having an amino acid sequence selected from the group consisting of SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47 and SEQ ID NO: 48, wherein the ELP4 polypeptide is over-expressed in the transgenic strawberry or tomato plant, and exhibits increased resistance to anthracnose crown rot, powdery mildew, angular leaf spot, or bacterial speck as a result of the heterologous nucleic acid sequence, relative to an otherwise isogenic strawberry or tomato plant that is wild-type for the ELP4 gene and does not comprise the heterologous nucleic acid sequence.

2. The strawberry or tomato plant of claim 1, wherein the nucleic acid sequence encoding ELP4 is operably linked to a heterologous promoter which is a developmentally-regulated, organelle-specific, inducible, tissue-specific, constitutive, cell-specific, or seed specific promoter.

3. The strawberry or tomato plant of claim 2, wherein the promoter is a constitutive or inducible promoter.

4. The strawberry or tomato plant of claim 1, wherein the plant is a strawberry plant.

5. The strawberry or tomato plant of claim 1, wherein the plant is a tomato plant.

6. The strawberry plant of claim 4, wherein the strawberry plant displays altered production of runners.

7. The strawberry or tomato plant of claim 1, wherein the resistance is to a disease caused by a *Colletotrichum gloeosporioides, Podosphaera aphanis, Xanthomonas fragariae,* or *Pseudomonas syringae.*

8. The strawberry or tomato plant of claim 1, further defined as an $R_0$ transgenic strawberry or tomato plant.

9. The strawberry or tomato plant of claim 1, further defined as a progeny strawberry or tomato plant of any generation of an $R_0$ transgenic strawberry or tomato plant, wherein the transgenic strawberry or tomato plant has inherited the heterologous nucleic acid sequence from the $R_0$ transgenic strawberry or tomato plant.

10. The strawberry or tomato plant of claim 1, wherein the heterologous nucleic acid sequence comprises at least 90% sequence identity to a sequence selected from the group consisting of SEQ ID NOs:13-24.

11. A seed that produces the strawberry or tomato plant of claim 1.

12. A strawberry or tomato plant part of the strawberry or tomato plant of claim 1.

13. The strawberry or tomato plant part of claim 12, further defined as a protoplast, cell, meristem, root, leaf, pistil, anther, flower, seed, fruit, embryo, stalk, or petiole.

14. A recombinant nucleic acid molecule comprising a nucleic acid sequence selected from the group consisting of:
   (a) a nucleic acid sequence of any of SEQ ID NOs: 14-15, 17, 19-20, and 24 or a complement thereof; and
   (b) a nucleic acid sequence encoding a polypeptide having the amino acid sequence of any of SEQ ID NOs: 38-39, 41, 43-44, and 48;
   wherein the nucleic acid sequence is operably linked to a heterologous promoter sequence and wherein expression of the nucleic acid molecule in a plant cell results in overexpression of ELP4 relative to an otherwise isogenic plant which does not comprise the heterologous nucleic acid sequence.

15. The nucleic acid molecule of claim 14, wherein the nucleic acid sequence consists of the nucleic acid encoding the polypeptide having the amino acid sequence of any of SEQ ID NOs: 38-39, 41, 43, 44, 43-44, and 48, wherein the nucleic acid sequence exhibits at least 95%, 96%, 97%, 98% or 99% sequence identity to any of SEQ ID NOs: 14-15, 17, 19-20, and 24 or a complement thereof.

16. The nucleic acid molecule of claim 14, wherein the heterologous promoter sequence is a developmentally-regulated, organelle-specific, inducible, tissue-specific, constitutive, cell-specific, or seed specific promoter.

17. A transgenic plant cell comprising the nucleic acid molecule of claim 14.

18. A transgenic plant or plant part comprising the nucleic acid molecule of claim 14.

19. A method of increasing disease resistance to anthracnose crown rot, powdery mildew, angular leaf spot, or bacterial speck in a strawberry or tomato plant comprising: forming one or more transgenic strawberry or tomato plants comprising a heterologous nucleic acid sequence that encodes an ELP4 polypeptide having an amino acid sequence selected from the group consisting of SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47 and SEQ ID NO: 48 and identifying at least one transgenic strawberry or tomato plant or progeny strawberry or tomato transgenic plant over-expressing the ELP4 polypeptide and having increased disease resistance to anthracnose crown rot, powdery mildew, angular leaf spot, or bacterial speck relative to an otherwise isogenic strawberry or tomato plant which does not comprise the heterologous nucleic acid sequence.

20. The method of claim 19, wherein the disease is caused by *Colletotrichum gloeosporioides, Podosphaera aphanis, Xanthomonas fragariae,* or *Pseudomonas syringae.*

21. The method of claim 20, wherein the disease is caused by *Colletotrichum gloeosporioides* or *Podosphaera aphanis.*

22. The method of claim 21, wherein the disease is Strawberry Anthracnose or Strawberry Powdery Mildew.

23. The method of claim 20, wherein the disease is caused by *Pseudomonas syringae.*

24. The method of claim 20, wherein the disease is caused by *Xanthomonas fragariae.*

25. The method of claim 24, wherein the disease is Strawberry Angular Leaf Spot.

26. The method of claim 23, wherein the disease is Bacterial Speck of Tomato.

27. A method of producing a strawberry or tomato plant having increased disease resistance comprising:
   (a) crossing a first strawberry or tomato plant with a second strawberry or tomato plant, wherein the first strawberry or tomato plant comprises a heterologous nucleic acid sequence that encodes an ELP4 polypeptide having an amino acid sequence selected from the group consisting of SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47 and SEQ ID NO: 48, and wherein the first strawberry or tomato plant over-expresses the ELP4 polypeptide and exhibits increased disease resistance to anthracnose crown rot, powdery mildew, angular leaf spot, or bacterial speck as a result of the overexpression relative to an otherwise isogenic strawberry or tomato plant which does not comprise the heterologous nucleic acid sequence;
   (b) obtaining one or more progeny strawberry or tomato plants, and
   (c) selecting a progeny strawberry or tomato plant which is over-expressing the heterologous nucleic acid sequence that encodes the ELP4 polypeptide, wherein the ELP4 polypeptide is over-expressed in the progeny strawberry or tomato plant, and wherein the progeny strawberry or tomato plant exhibits disease resistance to anthracnose crown rot, powdery mildew, angular leaf spot, or bacterial speck as a result of the heterologous nucleic acid sequence, relative to an otherwise isogenic strawberry or tomato plant which does not comprise the heterologous nucleic acid sequence.

* * * * *

SEQUENCE LISTING

```
<160> NUMBER OF SEQ ID NOS: 48

<210> SEQ ID NO 1
<211> LENGTH: 1698
<212> TYPE: DNA
<213> ORGANISM: Arabidopsis thaliana

<400> SEQUENCE: 1
atggcgacgg cggtagtgat gaacggcgag ctgaaaaagc aacctcggcc aggtaaaggc      60
ggctatcagg gccgtggatt aactgaagaa gaagctcgag ttcgcgccat atcggagatt     120
gttagcacca tgattgagcg ttcacaccgc aacgagaatg ttgacctaaa cgcaattaaa     180
accgccgctt gccggaaata cggcctagca cgtgcgccta agctcgtgga gatgattgct     240
gcgcttcctg attcagagag agagactctt ctcccgaagc tccgtgccaa accggttcga     300
acagcttcag ggatcgccgt tgtggcggtt atgtcgaagc ctcataggtg cccgcatata     360
gctacgacgg ggaatatatg cgtttattgt cccggtggac ctgactctga ctttgagtat     420
agtactcagt cttacactgg atatgagcct accagcatgc gagctattcg agccaggtac     480
aatccatatg ttcaggcaag aagcaggata gatcagctga agcggttggg tcacagtgta     540
gataaggttg agttcatttt gatgggaggt actttcatgt cactgcctgc tgagtatcgg     600
gatttcttca tacggaatct tcatgatgct ttatcaggac acacttctgc caacgttgaa     660
gaggcagttg cttactctga acatagtgca actaaatgca ttgggatgac aattgaaacg     720
aggccagatt actgccttgg acctcattta cgacaaatgc tgatttacgg ttgcacccgg     780
ctagagatag gtgtccagag cacatatgaa gatgttgccc gtgacacaaa tagaggtcat     840
actgttgctg ctgtagctga ctgcttctgc ttggctaaag atgctggttt caaggtggtt     900
gcacatatga tgcctgatct tcctaatgtt ggggttgaga gagacatgga aagtttcaag     960 gagttttcg agagcccatc ttttagagca gatgggttaa aaatatatcc cacccttgtg    1020
atccgtggaa ctggactta tgaactatgg aaaactggga ggtaccgaaa ttatccacct    1080
gagcagcttg tggatatagt tgcaaggatt ctctccatgg tacctccatg gacacgtgta    1140
tatagagttc agcgtgatat tcctatgcct ctggttacgt cagggggtaga aaaaggaaat    1200 cttcgtgaac tggctctagc cagaatggat gacttgggcc ttaaatgccg tgatgtccgt    1260
actcgtgaag ctggaattca ggacattcat cataaaatta agccagaaca agtagagctt    1320
gtgcgtcgtg attacactgc caatgaaggt tgggagacgt tcctttctta tgaagataca    1380
cgccaggaca ttcttgttgg attgctacgt ttgcgaaaat gcgggaagaa tgtaacgtgt    1440
ccagaactca tgggaaagtg ttctgttgtc cgtgagcttc atgtatacgg aacagctgta    1500
ccagttcatg gtcgagatgc tgataagttg caacatcagg gctatggtac acttctgatg    1560
gaagaagcag agaggattgc tagaagagaa catcgatcta acaaaatcgg tgtgatttct    1620
ggtgtaggaa ccagacatta ctacagaaag ttgggttatg aattggaagg tccttacatg    1680
gtgaagcatc ttctttga                                                  1698
```

<210> SEQ ID NO 2
<211> LENGTH: 1698
<212> TYPE: DNA
<213> ORGANISM: Brassica napus

<400> SEQUENCE: 2

| | | | | | |
|---|---|---|---|---|---|
| atggcgacgg | cgatagtgat | gaacggcgaa | tcgaaaaagc | aaccacggcc | aggtcgcggc | 60 |
| ggcttccaag | gccgtggact | aacggaggaa | gaagctagag | ttcgcgccat | atcggagatc | 120 |
| gtcagcacca | tgatcgagcg | ctcccaccgc | aacgagaacg | tggacctaaa | cgcgattaaa | 180 |
| acccaggctt | gccggaaata | cggcctagcg | cgagcgccga | agctagtgga | gatgatagcg | 240 |
| gcgctgcctg | actcagagag | agagactctc | ctcccgaagc | tccgcgctaa | accggtccga | 300 |
| accgcttcag | gaatcgcggt | ggtggcggtt | atgtcgaaac | cgcacaggtg | ccccacata | 360 |
| gcgacgacgg | ggaatatatg | cgtgtattgt | ccaggtggac | ctgattctga | cttcgagtat | 420 |
| agtactcagt | cttacactgg | ttatgagcct | accagcatgc | gagctattcg | agccaggtat | 480 |
| aatccatatg | ttcaggcaag | gagcaggata | gatcagctga | gcggttggg | tcacagtgta | 540 |
| gataaggttg | agttcatttt | gatgggaggt | acttttatgt | cgcttcctgc | tgagtacagg | 600 |
| gatttcttca | tacggaacct | tcatgatgct | tgtccggat | acacttctgc | caatgttgaa | 660 |
| gaagctgtta | cttactctga | acatagtgca | accaaatgca | ttggcatgac | gattgaaacg | 720 |
| aggccagatt | actgtcttgg | acctcatcta | aggcaaatgc | tgacttatgg | ttgcacccga | 780 |
| ctagagattg | gtgtccagag | cacatatgaa | gatgttgccc | gtgacacaaa | tagaggtcat | 840 |
| actgttgctg | cggtagccga | ctgcttctgc | ttggctaaag | atgctggttt | caaggtggtt | 900 |
| gcacatatga | tgcctgatct | tcctaatgtt | ggggttgaga | gagacatgga | aagtttcaag | 960 |
| gagttttcg | agagtccgtc | attcagagcg | gatgggttaa | aaatatatcc | tacccttgtg | 1020 |
| atacgtggaa | ctggcctta | cgaattatgg | aaaactggga | gataccgaaa | ctatccacct | 1080 |
| gagcaacttg | tggatatagt | tgcaaggatt | ctctccatgg | tgcctccatg | acacgtgtt | 1140 |
| tatagagttc | agcgtgatat | ccctatgcct | ctggttacgt | cgggggttga | aaaggaaat | 1200 |
| ctccgtgagc | tggctctggc | aagaatggat | gatttgggcc | ttaaatgccg | tgatgttcgc | 1260 |
| actcgcgaag | ctggaattca | ggacattcat | cacaaaatca | agccagaaca | agtagagctt | 1320 |
| gttcgtcgtg | attacactgc | aaaccaaggt | tgggagacat | tcctttcata | tgaagataca | 1380 |
| cgccaggaca | ttcttgttgg | gttattacgt | ttgcgtaaat | gtggtaagaa | cgtaacttgt | 1440 |
| ccagaactca | tgggaaagtg | ttctgttgtc | cgtgagcttc | atgtatatgg | aacggctgta | 1500 |
| ccagttcatg | tcgggaggc | tgataagttg | caacatcagg | ggtacggaac | acttctgatg | 1560 |
| gaagaggcag | agaggattgc | tagaagagaa | catcgctcta | acaaaatcgg | tgtgatttca | 1620 |
| ggtgtgggaa | cccgacatta | ctacagaaag | ttgggttatg | aattggaagg | tccttacatg | 1680 |
| gtgaagcatc | ttctttga | | | | | 1698 |

<210> SEQ ID NO 3
<211> LENGTH: 1698
<212> TYPE: DNA
<213> ORGANISM: Gossypium arboreum

<400> SEQUENCE: 3

| | | | | | |
|---|---|---|---|---|---|
| atggcaactg | ccgccataga | tccggagctg | aagaagctcc | cgcgccccgg | tcgggcgga | 60 |
| tttcaagccc | acggtctaac | cgaggaagag | gcccgagtac | gagccattgc | tgaaattgtc | 120 |
| aactccatgg | tagaactctc | aaggaagaac | caaagagtgg | atctaaacgc | aatcaaatct | 180 |

| | |
|---|---|
| gccgcgtgtc ggaaatatgg actcgcacgt gcaccgaagc tggtagagat gatcgctgca | 240 |
| cttcccgagt cggagcgcgt gtctttactc cctaagcttc gcgccaaacc ggttagaacc | 300 |
| gcttccggaa tcgcggtcgt ggcggttatg tcgaagccac atcggtgccc gcatattgcg | 360 |
| actacaggga atatttgtgt ttattgcccc ggcggaccgg attcggattt tgagtatagt | 420 |
| actcagtcgt atacgggata tgagccaact agcatgcgag caattagagc gaggtataat | 480 |
| ccatatgtcc aggcaagaag caggattgat cagctgaagc gactgggtca cagtgtagat | 540 |
| aaggttgaat tcatcttgat gggtggcacc ttcatgtcac tgccggcaga ttaccgagac | 600 |
| tattttatta ggaatcttca tgatgctttg tcaggtcaca cttctgccaa tgttgaagag | 660 |
| gcagttacct actctgagca tagtgctgta aagtgcattg gaatgacaat tgaaactagg | 720 |
| ccagactatt gccttggtcc tcacctgcgt caaatgcttt cttatggttg tacacgattg | 780 |
| gagattggag ttcaaagcac atatgaagat gttgctcgtg acactaatag aggacacacc | 840 |
| gtagctgcag tggctgattg ttttttgcttg gcaaaggatg ctggtttcaa ggttgttgct | 900 |
| catatgatgc ccgatcttcc taatgttggt gtcgagaggg acttggaaag ttcaaggag | 960 |
| tttttcgaga gccctttatt tcgagctgat gggcttaaaa tatatcccac gcttgtgatc | 1020 |
| cgtgaactg gcctttatga gctttggaaa actggcaggg accgaaatta cccgcctgag | 1080 |
| cagcttgtgg acattgtggc aaggatcttg ccatggtac cgccttggac acgtgtttat | 1140 |
| agggtccagc gtgatattcc tatgcctttg gttacctctg gggttgaaaa gggaaatctt | 1200 |
| cgtgaactag ctttagctcg tatggatgac ttgggcttga agtgccgaga tgttcgaacg | 1260 |
| cgtgaagctg gaattcagga tattcaccac aaaattaaac ccgaagaagt tgagcttgtt | 1320 |
| cgacgtgatt atacagcaaa tgaaagctgg gaaacatttc tgtcttatga agatacacgc | 1380 |
| caggatattc ttgttgggtt gttgcgactg cgtaagtgtg gccagaatac tacttgccct | 1440 |
| gaactaatgg ggaaatgttc tattgtccgt gaactccatg tatatggaac tgctgttcca | 1500 |
| gttcatggca gagatgctga caagttacaa caccagggtt atggtacact tctaatggaa | 1560 |
| gaagcagagc gtattgcaag aagggagcat agatcaacaa aaatagcagt gatatctggt | 1620 |
| gtaggaaccc ggcattatta taggaaattg gggtatgagc ttgacggccc ttacatggtt | 1680 |
| aaatatctga cttcatag | 1698 |

<210> SEQ ID NO 4
<211> LENGTH: 1695
<212> TYPE: DNA
<213> ORGANISM: Glycine max

<400> SEQUENCE: 4

| | |
|---|---|
| atggcggcgg cagcggtggc ggaggtgagg aaggccccac ggccgggcaa gggcgggtac | 60 |
| gaagcgcacg gcctgagcga ggaggaggcg cgagtgcgcg ccatcgcgga gatcgtcagc | 120 |
| tccatggtgg acctctctca caaggccag aacgtggacc tcaacgcgct caagtccgcg | 180 |
| gcgtgccgca agtacgggct ctcacgcgcg cccaagctcg tggagatgat cgcggcgctc | 240 |
| cccgacgccg agcgcgagac gctcctcccc aagctccgcg ccaagcccgt ccgcaccgcc | 300 |
| tccggaatcg ccgtcgtcgc ggtcatgtcg aagccgcacc ggtgcccgca catcgccacc | 360 |
| accggcaaca tctgcgtcta ctgccccggg ggacctgact ccgatttcga gtacagtact | 420 |
| cagtcttaca ctggttacga accaaccagc atgcgcgcaa ttcgtgcgag gtataatcca | 480 |
| tatgtccaag cgaggagcag gatagatcag cttaagcgtt gggtcatag tgtagacaag | 540 |
| gttgagttta tcttaatggg aggtaccttc atgtcacttc cggctgatta ccgtgattac | 600 |

```
tttataagaa atcttcatga tgctttgtct ggacacacat ctgctaatgt ggaagaggct    660
gtggcatact ctgagcatgg ggcaaccaag tgtattggta tgacgattga aacgaggcca    720
gattattgtc ttgggcctca cttgcgccaa atgctttctt atggttgtac acgattggag    780
attggagtcc aaagcaccta tgaggacgtt gctcgagaca caaatagagg acacactgtt    840
gctgctgtag cggattgttt tgcctggct aaagatgctg gtttcaaggt tgttgctcac     900
atgatgcctg accttcctaa tgttggtgtt gaaagggaca tggaaagttt ccggagtttt    960
tttgagagcc ccatgtttag agcagatggg cttaaaatat atcctacact tgtaattcgt   1020
ggaactgggc tttatgagct ctggaaaact ggcaggtata gaaactatcc acctgagcaa   1080
cttgtggaca ttatagcaag gatccttgca atggtacccc catggacacg tgtttataga   1140
gttcagcggg atattcccat gcctctggtt acctctgggg ttgagaaagg aaatctgagg   1200
gagctagcat tagctcgaat ggatgacctg ggattgaaat gtcgtgatgt tcggaccaga   1260
gaagctggaa tccaggatat tcaccaccaa attaagccag aagaggtgga gcttgttcgg   1320
cgtgattata tggcaaatga gggttgggaa acatttctat catatgaaga tacacggcag   1380
gatatccttg ttggttttgtt gcgactgcga aaatgtggcc gcaacactac ttgtccagag   1440
cttatgggga agtgttctat tgttcgtgaa ctccacgttt atggaactgc tgtaccagtt   1500
catggacggg atgctgacaa gctacaacac cagggttatg gcacactttt aatggaggag   1560
gcagaacgta ttgcttgcag agaacacaga tcaacaaaaa tagctgtaat ttcagggggtt   1620
ggcacacgcc attattacag gaaactggga tatgagcttg aaggacctta catggtgaaa   1680
tatctagtga aataa                                                    1695

<210> SEQ ID NO 5
<211> LENGTH: 1695
<212> TYPE: DNA
<213> ORGANISM: Citrus sinensis

<400> SEQUENCE: 5
atggccaccg ccgtgctacc acaagacacc aaaaagctcc cccggcccgg gcggggcgga     60
tttcaggccc acgccttac cgaagaagag gctcgagtcc gggccatcgc cgaaatcgtc    120
aactcaatgg ttgaactatc acgcaaaaac gaaacggtcg acctaaacgc aataaaatcc    180
gccgcgtgcc gcaagtacgg tcttgcacgc gccctaaat tagtagagat gatcgccgcg    240
ctacccgaga tgaccgcga agccttgctg cccaagcttc gagccaagcc cgtcagaacg    300
gcttccggta ttgctgtcgt ggccattatg tcaaaaccac acagatgccc ccatatcgcg    360
acgactggaa acatttgcgt gtactgtccg ggtgggccag actctgatt tgagtacagt    420
acgcagagtt acactggata cgagcctact agcatgcgcg ctattagagc cagatacaat    480
ccatatgtcc aggcaagaag caggattgat cagctaaaac gtttgggtca tagcgtagac    540
aaggttgagt tcatcttaat gggtggtacc ttcatgtctc tgccagcaga ttaccgtgat    600
tactttataa ggaatcttca tgatgcttta tctggacata cttctgccaa tgttgaagag    660
gcagtcactt attctgagca tggtgctaca aatgtattg gcatgacaat tgaaacgagg    720
ccagattatt gccttggacc tcatttgcgc caaatgcttt cttatggttg tacacgattg    780
gagataggag ttcaaagcac atatgaggat gttgctcgtg acacaaatag agggcatacg    840
gtagctgctg tggctgattg ttttttgcctg gcaaaggatg ctggtttcaa ggttgttgct    900
catatgatgc ctgatcttcc aaatgttgga gtcgagaggg acttggaaag ttttcgggag    960
```

```
ttctttgaga gcccattatt tagagctgat gggcttaaaa tttatcctac gcttgtgatt    1020
cgtgggactg ggctttatga gctctggaaa actggtaggt atagaaatta cccacctgag    1080
caacttgtgg acattgtcgc caggattcta gccatggtac cccttggac tcgtgtttat     1140 agagttcagc gtgatattcc catgcctttg gttacttccg gggttgagaa agggaacctt    1200
cgggagctag ctttagctcg gatggatgac ttgggcttga aatgccgtga tgttcggaca    1260
cgtgaagctg gaattcagga catccatcat caaataaagc cagaagaagt agagcttgtc    1320
cgtcgtgatt atgtggcaaa tgaaggttgg gaaacatttc tttcgtacga agacacacgc    1380
caggatattc ttgttggctt gttgcgcttg aggaagtgtg gcggaatgt tacttgtcca     1440 gagctcatgg gcaagtgttc tattgttcgt gaactccatg tgtatggaac tgctgttcct    1500
gtgcacggtc gggaagctga caagctgcaa caccagggtt acgtacact cttaatggaa     1560 gaggcagagc ggattgcact tagagagcac agatcaagaa agatggccgt tatttcaggt    1620
gtaggaactc gacattatta tagaaaattg ggatacgaac ttgaaggtcc ttacatggtg    1680
aaatatcttg agtga                                                    1695

<210> SEQ ID NO 6
<211> LENGTH: 1698
<212> TYPE: DNA
<213> ORGANISM: Solanum lycopersicum

<400> SEQUENCE: 6
atggcggcgg cggcggtagc ggtagcggag acccggaagc tcccgcggcc gggaaggggc      60
ggagttgttt ccctcggcct gacagaagaa gaagctagag ttcgtgctat aacggagatc     120
gttaacaaca tggtggaact ctcacggaaa ggcaaggatg ttgacctaaa tgcgctaaag     180
tcagcagcgt gccgaaaata cgggctctct cgggctccta gttggtaga gatgatcgct     240 gctttgcctg actctgaacg tgaaacactg cttcccaaac tccgagccaa gctgtccgt     300 acagcctctg gaatagctgt cgtagctgta atgtccaagc tcatcgttg tcctcatata     360 gctaccaccg gaaacatttg tgtctattgc cctggcggcc ccgattctga ttttgagtac    420
agtacacagt catacacggg atatgaacct actagtatgc gagctattcg agctagatac    480
aatccttatg tacaagctcg aagccggatt gatcaactta agagattggg tcacagtgtt    540
gacaaggttg aatttatctt gatgggaggt acattcatgt cattgcctgc tgaataccgt    600
gattacttca cacggaatct ccatgatgct ttatccggac atacttctgc caatgttgaa    660
gaggctgtcg catactctga acatggggcg acaaagtgca ttgggatgac aattgaaacg    720
aggccagact actgccttgg acctcatctg agacaaatgc tttcttacgg ttgtacgcgg    780
ctagaaattg gagtacagag tacgtatgag gatgttgctc gtgacaccaa tagaggccac    840
actgttgcag ctgtggctga ttgcttttgt ttggcaaaag atgctggctt caaggtggtt    900
gctcatatga tgccggacct tccaaatgtt ggcgttgaaa gagacttgga gagtttcaag    960
gaattctttg aaagtccttc atttaggact gatggactta aaatttatcc tacacttgtt    1020
attcgtggca caggactcta tgaactgtgg aaaactggaa ggtatagaaa ttatccgcca    1080
gagcagcttg tagacattgt agcaaggatt ctttctatgg tgccaccctg acccgagtt    1140 taccgggtcc aacgtgatat ccctatgcct ctagtgactt ctggagttga aaagggaat    1200 ctccgagaac tggctttagc tcgaatggat gatcttggct tgaaatgccg agatgtccga    1260
acacgcgaag ctgggatcca ggacattcac aacaagataa ggcctgaaga ggttgagctt    1320
gttcgccgcg attatactgc aaatgaagga tgggagactt tcctttcata tgaagataca    1380
```

```
cgccaggata ttcttgttgg attgctacgg ctgcggaagt gtggacggaa tgtgacttgc    1440
ccagaactta cgggaaggtg ttcaattgtt cgtgagcttc atgtgtatgg gactgcagtt    1500
cctgttcatg gtcgagacac agataagctg cagcaccagg ttatggcac tctgctgatg     1560 gaggaggctg agcggattgc tcggagggag cataggtcga ccaaaatcgc tgttatatcg    1620
ggtgtaggga cccggcatta ctacagaaag ctaggctatg agcttgaagg tccttacatg    1680
gtaaaaaacc ttgtgtag                                                  1698

<210> SEQ ID NO 7
<211> LENGTH: 1692
<212> TYPE: DNA
<213> ORGANISM: Medicago truncatula

<400> SEQUENCE: 7
atggcagctg caatggtggc ggagggaaaa aaggcaccac gtcctgggaa aggtggcttt      60
gaaggccatg gtcttagtga agaagaagca cgcgttcgag ccattgcaga aattgtgaac     120
tccatggttg acttatctca taaaggccac aaagtcgatc tcaatgctct caagtccgcg     180
gcgtgccgaa agtacggcct ctcacgtgca cccaaacttg ttgagatgat tgctgctcta     240
cctgactccg aacgagaggt tcttcttcct aaactccgag ccaaacccgt ccgaaccgca     300
tctggaatag ccgttgttgc tgtcatgtca aaacctcatc gttgtcctca cattgccacc     360
accggtaaca tttgtgtcta ttgccctggc ggtcctgact ccgattttga atacagtact     420
cagtcttaca ctggttatga acctaccagc atgcgtgcaa ttcgagcaag gtataaccct     480
tatgtgcaga caagaggtag gattgatcag cttaagcgtt taggtcacag tgtagacaag     540
gttgagttta tattaatggg tggaactttc atgtcacttc cggcggatta ccgtgattac     600
tttacaagga atcttcatga tgctttgtct ggacacacct ctgccaatgt agaagaggct     660
gtgatgtact ctgagcatag tgcaaccaag tgtattggca tgacaattga acgaggcca      720 gattattgtc ttgggcctca cctgcgacaa atgctttctt acggttgtac acgattggag    780
attggagtcc aaagcactta tgaggatgtt gctcgtgaca ctaatagagg acatactgtt    840
gctgctgtag ctgattgttt tgcctagct aaagatgctg gtttcaaggt agttgctcac     900
atgatgcctg atcttccaaa tgttggtgtt gaaagggaca tggaaagttt ccgagagttt    960
tttgaaagtc ccttgtttag aactgatggg cttaaaattt accccactct tgtaatacgt   1020
ggaactgggc tttatgagct ctggaaaact ggcaggtata gaaattatcc acctgagcaa   1080 cttgtgggaca tcatagcaag gatccttgca atggtacctc catggacacg tgtttataga   1140
gttcagcggg atattccaat gcctttggtg acctctgggg ttgagaaagg gaatctaagg   1200
gagttagcat tagctcgaat ggaagacttg ggttttaaaat gtcgtgatgt tcgcaccaga   1260
gaagctggaa tccaggatat tcatcaccaa attaaaccag agaggtgga acttgttcgt    1320 cgtgattata tggcaaatga aggttgggaa acatttttgt catacgaaga tacacgcgag   1380
gatatccttg ttggtttgtt acgactgcga aaatgtggcc gtaacactac ctgtccagag   1440
cttatgggta agtgttctat tgttcgtgag ctccatgttt atggaactgc tgtaccggtt   1500
catgggcggg attctgacaa gctacaacac caggggttatg gtacgcttct tatggaggag  1560
gctgagcgga ttgcttcgaa agaacacaga tcaactaaga tagctgtaat ttctggggtt   1620
ggcacacgcc attactacag aaaattggga tatgagcttg aagggcctta catgatgaaa   1680
tacctattgt aa                                                        1692
```

<210> SEQ ID NO 8
<211> LENGTH: 1704
<212> TYPE: DNA
<213> ORGANISM: Fragaria vesca

<400> SEQUENCE: 8

| | | | | | |
|---|---|---|---|---|---|
| atggcgactg | cggtggtggc | ggcggcagcc | gatcccatcc | gtaagcaacc | ccgtccgggc | 60 |
| cggggcgggt | tcgaagccca | cggactctcc | gaagaagagg | cccgcgtccg | cgccatagcc | 120 |
| gaaatcgtcg | gctccatggt | cgacctctcc | cgccgaggcg | aaaccgtcga | cctaaacgcc | 180 |
| ctcaaaaccg | ccgcgtgccg | caagtacggc | ctcgcacgtg | caccgaagct | ggtcgagatg | 240 |
| atcgccgcgc | ttccggaatc | ggaccgcgag | gcgctgcttc | cgaagctgaa | agccaagccg | 300 |
| gtccgaaccg | cctccggaat | cgccgtcgtg | gccgtgatgt | cgaagcctca | ccggtgccct | 360 |
| cacatcgcca | ccaccgggaa | tatttgcgtg | tactgccccg | gtgggcccga | ttcggatttt | 420 |
| gagtatagta | ctcagtctta | tactggatac | gagcctacta | gcatgcgcgc | aattcgagcc | 480 |
| agatacaacc | cgtatgttca | ggctagaggt | aggatagatc | agctgaagcg | attgggtcac | 540 |
| agtgtagaca | aggttgagta | catttttaatg | ggtggtacat | tcatgtcgtt | gccagcagat | 600 |
| taccgtgatt | actttattag | aaatcttcat | gacgcattat | ccggccatac | ttctgccaat | 660 |
| gttgaagagg | cagttgcata | ctctgagcat | ggggctacta | aatgtattgg | aatgaccatt | 720 |
| gaaacgaggc | cagattactg | ccttggacct | cacttgagac | aaatgcttac | ttatggttgt | 780 |
| acacgattgg | agattggagt | tcaaagtaca | tatgaggatg | tggctcgtga | tactaataga | 840 |
| ggtcacacag | tagctgcagt | ggctgattgt | ttctgcttgg | caaggatgc | tggtttcaag | 900 |
| gttgttgcac | acatgatgcc | tgatcttcca | aatgtagggg | ttgagagaga | catggaaagc | 960 |
| tttcgtgaat | tttttgagag | ccccttgttc | agagcagatg | gacttaaaat | ttatccaaca | 1020 |
| cttgtaatcc | gtggaactgg | actttatgag | ctctggaaaa | ctggaaggta | tagaaattac | 1080 |
| ccacctgagc | aacttgtgga | catagtagcc | agaatcctag | ccatggtacc | cccttggaca | 1140 |
| cgtgtttata | gagttcagag | ggacattcca | atgcctctag | ttacttctgg | agtagagaaa | 1200 |
| ggaaaccttc | gggagcttgc | tttagctcgg | atggaagact | tgggcttaaa | gtgtcgtgat | 1260 |
| gttcgaacac | gagaagctgg | aattcaggac | atacatcacc | aaattaagcc | ggatgaagtg | 1320 |
| gaacttgttc | gtcgtgatta | tacagcaaat | gaaggttggg | aaacatttct | ttcatatgaa | 1380 |
| gatacacgcc | aggatattct | agttgggttg | ttgcgattaa | gaaaatgcgg | cagaaatact | 1440 |
| tcctgtcctg | aactcatggg | gaagtgttct | attgttcgtg | aacttcatgt | ttatgggact | 1500 |
| gctgttccag | ttcatgggcg | ggatgctggc | aagctgcagc | accagggcta | cggtacactt | 1560 |
| ttgatggaag | aagcagagcg | aattgctaga | agggagcaca | gatcaaccaa | gatcgctgtt | 1620 |
| atttcaggag | taggaactcg | tcactactac | agaaaattag | gatatgaact | tgaagggcca | 1680 |
| tacatggtta | aatatcttga | ctag | | | | 1704 |

<210> SEQ ID NO 9
<211> LENGTH: 1695
<212> TYPE: DNA
<213> ORGANISM: Cucumis melo

<400> SEQUENCE: 9

| | | | | | |
|---|---|---|---|---|---|
| atggcgactg | cgatggtggc | ggaaccaaat | cggaaactgc | ctcggcctgg | ccgaggcggc | 60 |
| ttcgaaggcc | atggattttc | cgaagaagaa | gctcgagttc | gtgctattgc | tgagattgtc | 120 |
| aactccatgg | tcgacctttc | gcgtaaaggg | caaaacgtcg | atctgaacgc | tctcaaatcc | 180 |

```
gccgcctgcc ggaagtatgg ccttgcacgg gcaccaaagc tcgttgaaat gatcgcagca      240
cttcctgaat cggaccgcga ggccctacta ccgaagcttc gagccaagcc ggttcgaaca      300
gcctccggta tcgcagtcgt ggccgtgatg tctaagccgc atcgttgccc tcatattgct      360
acgacgggga atatttgtgt gtactgcccc ggaggacctg attcagactt tgagtacagt      420
acccaatctt acactggtta tgagcctaca agcatgcgtg caattcgtgc aagatacaac      480
ccatatgtcc aggctagaag caggatagat cagttgaagc gtttgggtca cagtgttgat      540
aaggttgagt tcatcttaat gggtgggact ttcatgtcgc ttcctgctga ttatcgtgat      600
tactttataa ggaatcttca tgatgctttg tcagggcata cttctgccaa tgttgaagag      660
gcagttgcct actcagagca tggtgcagtt aaatgcatag gcatgacgat agaaacgagg      720
cctgattatt gtcttggacc tcacttgaga caaatgcttt cttatggttg tacacgacta      780
gagattggag ttcaaagtac atatgaggat gtggctcggg acactaacag agggcatact      840
gtagctgccg tggctgattg cttttgcttg caaaggatg ctggtttcaa ggttgtagca      900
cacatgatgc ctgaccttcc aaacgttggg gttgagagag acctggagag ttttcgcgag      960 ttcttttgaaa atccttcatt tagagcagat gggctcaaaa tatatccaac acttgtaatc     1020
cgtggaactg ggctctatga actgtggaaa actggcaggt atagaaacta tcccccagag     1080
caacttgttg atattgtggc aagaatcctg gctatggtac cccttggac ccgagtttat     1140 agagtacaac gggatatccc aatgcctttg gttacttctg gcgtagagaa aggaaatctt     1200
cgagagttag ctctagctcg gatggatgat ttgggcttaa aatgccgtga tgttaggact     1260
cgtgaagctg gaattcagga cattcatcat aagattaaac ctgatgaagt tgagcttgtt     1320
cgtcgtgatt acatggcaaa tgaaggctgg gaaacatttc tatcctatga agatgtttgc     1380
caggacattc ttgttggttt gcttcggctg agaagatgtg gtcgtaacac cacttgtccc     1440
gaactcgtag ggaagtgttc cattgttcgt gaactccatg tgtatggaac tgctgttcca     1500
gttcatggac gtgatacaga gaagctgcaa caccagggtt atggtacgct tttgatggag     1560
gaggcagagc ggatagctcg tcatgagcat cgatcaaaga agattgctgt tatatcaggc     1620
gttgggaccc gccattacta tagaaaatta ggctatgaac ttgaaggtcc atacatggtg     1680
aaaagccttg agtga                                                      1695
```

<210> SEQ ID NO 10
<211> LENGTH: 1713
<212> TYPE: DNA
<213> ORGANISM: Zea mays

<400> SEQUENCE: 10

```
atggcaaccg ccgccaccgc catggtggta cccgagcagc cgcgccgccg gaagccggcc       60
ccggggcgcg ggggagtggc cctccctgcg ggtctctcgg aggaggaggc cagggtgcgg      120
gccatcgccg agattgtctc ggcgatgggg gagctctcgc ggcgcgggga ggacgtggac      180
ctcaacgcgc tcaagtccgc cgcgtgccgg agatacggtc tggcgcgagc gcccaagctg      240
gtggagatga tcgctgccgt gcccgaggcc gaccgcgccg cgctgctgcc gcggttgcgc      300
gctaagcccg tgcgcacggc gtcgggtatc gccgtcgtcg ccgtcatgtc gaagccgcac      360
cgttgccccc acatcgctac caccggtaac atctgtgtct actgcccggg cggtcccgac      420
tccgacttcg agtacagcac gcaatcctac actggatacg aacccaccag catgcgtgcc      480
attcgggcaa ggtataatcc atatgtgcaa gccaggagca ggatagatca gctcaagagg      540
```

```
ttagggcata gtgtggataa ggtcgagttc atcttgatgg gtgggacttt catgtcctta      600
ccagctgatt atcgcgatta ttttatcaga aatcttcatg atgctttgtc ggggcacact      660
tcagcaaatg ttgaggaggc tatttgttat tccgaacata gtgctgtcaa atgtattggt      720
atgacgattg aaacgagacc tgattattgc ttggggcctc atctgcgcca gatgctatct      780
tatggttgta ctcgcctgga aattggtgtc cagagtacat atgaagatgt tgcccgtgac      840
acaaacagag gacacacggt ggctgctgtt gctgattgct tctgtttggc aaaagatgct      900
gggtttaagg tggttgccca catgatgcca gatttaccta atgttggagt tgaaagagac      960
ttagaaagtt tcagagagtt ttttgaaagt ccagcattcc gggctgatgg tctgaagatt     1020
tatccaacac ttgttattcg tggaactggt ctttatgagc tctggaaaac tggcagatat     1080
agaaattatc cacctgagct cttggtggat atcgtggcaa gaattctgtc tatggttcca     1140
ccatggacac gagtgtatcg ggtccagaga gatattccta tgcctcttgt cacttctggt     1200
gttgagaaag gtaaccttcg tgagctagct ttggctcgaa tggatgatct gggcctaaaa     1260
tgccgagatg tcagaacccg tgaagcaggg attcaggata ccatcacaa gatcaggcct      1320 gatgaagtag agcttgttag acgtgactat gctgcaaatg agggctggga gacgttcctc     1380
tcttatgagg atacacgaca ggatatcctg atcggcctgt tgcgcttgcg taaatgtggc     1440
cgtaatgtta catgccctga acttgtaggg aggtgttcaa ttgttcgtga gcttcatgtc     1500 tatgaactg cagtccctgt gcatggccgt gatgtagaca agctacagca ccaggggtat     1560
ggaactctgt taatggaaga agcagaaagg attgctcaaa aggagcaccg ttcagagaaa     1620
ttggctgtca tttcgggggt tggtactcgc cactactacc gcaaactggg ttatgagcta     1680
gaaggacctt atatggtcaa atgtttggca taa                                  1713

<210> SEQ ID NO 11
<211> LENGTH: 1722
<212> TYPE: DNA
<213> ORGANISM: Oryza sativa

<400> SEQUENCE: 11
atggccaccg ccgtagccgc cgccggcggt ggcggcggcg gcgagcagcc gcgcaggagg       60
aagccggcgc cggggagagg gggagtggtg ctccccgcgg ggctgtcgga ggaggaggcg      120
cgggtgcggg ccatcgcgga gatcgtgtcg gcgatggggg agctctcgcg gcgaggggag      180
gacgtggacc tgaacgcgct caagtcggcc gcgtgccgga ggtacgggct ggcgcgggcg      240
ccgaagctgg tggagatgat cgcggcggtg ccggaggccg accgcgccgc gctgctccca      300
aggctgcgcg ccaagcccgt gcgcacggcg tcgggcattg ccgtggtcgc cgtgatgtcg      360
aagccgcacc ggtgccccca catcgccacc acggggaaca tctgcgtgta ctgccccgga      420
ggccccgact ccgacttcga gtacagcacc cagtcctaca ccggctacga gcccaccagc      480
atgcgcgcca ttcgagcaag gtacaatcca tatgtgcagg ccagaagcag gatagatcag      540
ctcaaaaggc taggccatag tgtagacaag gtcgaattca tattgatggg tggaactttc      600
atgtcattac cagctgatta tcgggattat ttcattagaa atcttcatga tgccttatcg      660
ggacacactt ctgctaatgt tgaagaggct gtttgttatt cagaacatgg tgcagtcaaa      720
tgtattggca tgacaattga gacgagacct gattattgct tggggcctca tttgcgccag      780
atgctatctt atggttgtac ccgcttagaa attggtgttc agagcacata cgaggatgtt      840
gcacgtgaca caaacagagg tcacactgta gctgctgttg ctgattgctt tgtttggct      900 aaagatgctg gttttaaggt ggtcgcccac atgatgccag atttacctaa tgttggagtt      960
```

```
gaaagagatc tggaaagttt ccgagaattt tttgaaaatc cagcattccg agctgatggt   1020
ctaaagattt atccaactct tgtgattcgt ggaactggcc tttatgagct ctggaaaact   1080
ggcagatacc gaaactatcc acctgaactt ctggtggata ttgttgcaag aattctatcc   1140
atggtaccac cttggacacg agtttaccgt gtacaaagag atatccctat gcctcttgtt   1200
acttctggtg ttgaaaaagg taatcttcgt gagcttgctt tggctcgaat ggaagattta   1260
ggcttgaagt gccgagatgt tagaactcgt gaggcgggaa ttcaggatat ccatcacaaa   1320
attagacctg acgaagtaga gcttgttagg cgtgactatg ctgcaaatga gggctgggag   1380
accttctctc catacgagga tacacagcag gatatcctta ttggtctgct gcgattgcga   1440
aaatgtggcc gcaatgttac atgccctgag ctagtaggga ggtgttcaat tgtccgtgaa   1500
cttcatgtat atggaactgc agtccctgta catggtcgtg atgcagacaa actacaacac   1560
cagggttatg gtactctttt gatggaagaa gcagaaagaa ttgctcgcaa ggagcatcgt   1620
tcaaagaaaa tcgctgttat atcaggagtt gggactcgcc actactaccg taaactgggt   1680
tatgaacttg aggggcctta catggtcaaa tgtctggtct aa                      1722
```

```
<210> SEQ ID NO 12
<211> LENGTH: 1698
<212> TYPE: DNA
<213> ORGANISM: Eucalyptis grandis

<400> SEQUENCE: 12
```

```
atggcggcgg cggcagtggc agtggcggag accggcggc agccgcgccc gggcggcggc      60
ggcttccagg cgcacggcct caccgaggag gaggcccgcg tgcgggccat cggcgagatc    120
gtgagcgcca tggtggacct ctcccggaag ggcgagaccg tcgacctcaa cgccctcaag    180
tccgcggcgt gccgcaagta cggcctcgcg cgggccccga agctcgtgga gatgatcgcg    240
gcgctcccgg agtccgaccg cgacgcgctc ctcccgaagc tcaaggcgaa gcccgtccgc    300
accgcctccg gcatcgcccgt cgtcgccgtc atgtcgaagc ccaccggtg cccgcacatc    360 gccacgaccg ggaacatatg cgtgtactgc cccgggggc ccgactcgga tttcgagtac    420
agcacgcagt cgtacactgg ctatgagccg acgagcatgc gcgccattag ggctaggtat    480
aatccgtatg tccaagcgag gggcaggata gatcagctta gcggctggg tcacagcgtt    540 gataaggtgg agttcatatt gatgggcggc actttcatgt ctctaccagc agattatcgc    600
gattacttca tcaggaatct tcatgatgct ttatcaggac atacttcagc caatgttgaa    660
gaggcagttg cctactcaga gcacagtgcg gtgaagtgca tcggcatgac cattgaaacg    720
agaccagact attgccttgg accccatttg aggcaaatgc tttcatatgg ttgtacacga    780
ctggaaattg gggtccagag cacttatgag gatgttgcac gtgacactaa tagaggtcac    840
accgttgctg ctgtggccga ttgttttgc ttggcaaagg atgctggttt taaggttgtt    900
gctcacatga tgccggatct tcctaatgtg ggggttgaga gggacttgga aagtttccgg    960
gagttcttcg aaagccccct atttagagct gatggactta aaatatatcc tactcttgtg   1020
attcggggaa ctgggttgta tgaactttgg aagactggca ggtatagaaa ttacccaccc   1080
gagcaacttg tggatattgt cgcaagaatc ttggcaatgg tgccaccttg gacgcgtgtc   1140
tatagagttc agcgtgatat tccaatgcct ttagtcactt ctggtgttga aaaggaaac    1200 cttcgcgaat tagctctggc cagaatggat gatttaggtt tgaagtgccg agatgtacga   1260
actcgtgaag ctggaattca ggacatacac cataacatca ggccagaaga agtggagctt   1320
```

| | |
|---|---|
| gttcgacgtg attattcagc aaatgaaggt tgggagacat ttttatcgta tgaagataca | 1380 |
| caccaggata tacttgttgg tttgttgcgc ttgcggaagt gtggacggaa cactacttgc | 1440 |
| cctgagctaa ttgggaagtg ctctatcgtt cgtgagcttc atgtgtatgg aactgctgtt | 1500 |
| ccagttcatg gacgtgatgc tgagaaattg caacaccagg ttatggtac acttctgatg | 1560 |
| gaggaagctg aaagaatcgc tcgtagggag catagatcga caaaaatagc agtcatatcc | 1620 |
| ggtgtgggaa ctcgccatta ctacaggaaa ttgggctatg agctcgaagg gccttacatg | 1680 |
| gtgaagtacc tcgagtga | 1698 |

<210> SEQ ID NO 13
<211> LENGTH: 1068
<212> TYPE: DNA
<213> ORGANISM: Arabidopsis thaliana

<400> SEQUENCE: 13

| | |
|---|---|
| atggctgcac caaacgttcg tagtagtagc agcttctctc gcaacatatc agttgtgtca | 60 |
| tcgcctcaaa ttcctggtct caaaagtggt cctaatggca cagcttttat atcgtcaggg | 120 |
| attcgtgatc ttgacaggat actaggtggt gggtatcctt tgggaagctt agtaatggta | 180 |
| atggaagatc ctgaagcacc gcatcatatg gatctgttaa gaacttacat gtctcagggg | 240 |
| cttgttaaca atcaaccact tctttatgct agtccttcaa agatcccaaa agggtttctt | 300 |
| ggtactttgc cgcatcctgc atcatccaaa gaggataagc ctactgcgcc cgaccctgat | 360 |
| cagggagaga gcttgaggat tgcttggcag tatcggaagt atttggaaaa ccagaagaat | 420 |
| gctattgatg attactccaa tgactttgat atgagaaagc ccttggagag caatttctg | 480 |
| agcggacggc ccatagattg tgtcagtctg ttagactctt cagatctttc cattgctcag | 540 |
| gaccactgtg ctacgttttt atcaaaattt ccaagaaaca gcagtaacat tgcatctatt | 600 |
| ggccgcatcg caatccagtc ttttgctct ccctgtgtg agtattctga aaggaatca | 660 |
| gacatgctct cattcataag attgctgaaa agtatgctta tggtttcaaa tgcggtagcc | 720 |
| attgttactt tcccgccttc cctgctctcc ccatcttcct ctaaaagact gcagcatatg | 780 |
| gcagataccl tgctctctat caaagcaatc cagatggtg acaaggaatt ggagaaactc | 840 |
| ctcactggct acaaggatat aaatggattc ctcaacatac acaaggttgc tcgtatcaac | 900 |
| acacaggtgc ctgtaattct tgaggcaaaa accttctcaa tgagcttgaa gaagagaaga | 960 |
| ttcttggctc tagagtgtct gaatcaagcc cctgtagacg ggtccagtgg aacatcgtat | 1020 |
| ggcacatctg gtagctgctc atccaaatcc ggagcactag atttttga | 1068 |

<210> SEQ ID NO 14
<211> LENGTH: 1128
<212> TYPE: DNA
<213> ORGANISM: Brassica napus

<400> SEQUENCE: 14

| | |
|---|---|
| atggctgcac ccaacgttcg tactagcagc ttctctcgca acatatcagt tgtctcctca | 60 |
| tcccctcaaa tacctggtct caaatgcggt cctaatggca ctactttcat atccactggg | 120 |
| attcgtgatc tcgacaggat actaggtggt gggtatcctt tgggaagctt agtgatggtg | 180 |
| atggaagatc ctgaagcgcc gcatcatatg gatctcctga ggactttat gtctcaaggg | 240 |
| cttgttaaca accagccact tctttacgct agtccttcca agatcctag agggtttctt | 300 |
| ggtactttgc cgaatcccgg atcgtccaaa gaagataagc ctactgcccc agaccttgat | 360 |
| cagggagaga gcttgaggat tgcttggcag tatcggaagt atatggaaaa ccagaagagt | 420 |

-continued

```
tctattgatg attactccaa tgactttgat atgagaaagc cattggagag gcagtttctt      480
gctggacggc cgattgattg tgtcagtctg ctagattctt ccgatctttc tgttgctgag      540
gaccattgcg ctactttttt atcaaaattt ccgaggttgt gtatcatctc tttcttattt      600
gatggtcatt tacttctctt taaacttgta aacagcagta acattgcatc cattggccgc      660
atcgccatcc agtcattctg ctctccccctt tgtgagtatt ctgataagga atcagaaatg     720
ctttcattca taagattgct gaaaagtatg ctgatggttt caaatgcggt agccattgtt      780
actttcccgc cttccatgct ctccccgtct tcctcaacaa gactgcagca catggcggat      840
accttactct ctatcaaagc gatcccagat ggtgacaagg aattggagaa gcttctcact      900
ggctataagg acataaatgg attcctcaac gtacacaagg ttgcgcgtat caacacacag      960
gtgcctgtaa ttctagaggc aaagaccttc tcaatgagct aaagaagag aaggttcttg      1020
gctctagagt gtctgaatca agcccctgta gacggatcca gtggaacatc gtatggcaca    1080
tctgggagct gctctggatc atccaaatcc ggagcactcg atttctga                  1128
```

<210> SEQ ID NO 15
<211> LENGTH: 1086
<212> TYPE: DNA
<213> ORGANISM: Gossypium arboreum

<400> SEQUENCE: 15

```
atggctgcgg ccaagactcg gacaagtacc ttctctcgaa acctttccac tgcagcccca      60
tctcatggcc ccggacttaa gtgtgggcca aatggcacgg tctttctatc ttctgggata     120
cccgatcttg acaagatact gggtggtggg ttcccattgg gaagtctagt tatggtgatg     180
gaagacgcag aagcacctca tcacatgctt ttgttgagga atttcatggc tcagggactt     240
gttctcggcc aacctcttct ctattctagt ccagccagag atccaagggg tttttttgggt    300
actttgccaa gtcctgctgc atccaaagat gacaaatccc aggaacgcga tccagatcag     360
gagaaaggtc tgagaattgc ttggcagtat aagaagtatt ttggtgaaag tcagctcgat     420
ggacaaagag atagtaaaca tgagtactct aatgaatttg atttgaggaa gccccctagag    480
aggcacttca taaatggacc acgcatagat tgtgttagca tccaagattg tcctgatctt     540
tccactcttc gagaccgttg tgcaacattt ttatcccagt ttccacgaaa tgatggcagc     600
atttcatgtg ctggtcgtat agctatccaa tcatttgtg ctccacaatg tgcatattcg      660
aacatggagt gggatatgct ttcatttatt agatatctca aaagcatggt ccggtcttca    720
aattcagtcg ccataataac ctttcctcct tcccttcttt caccatcctt ctgtaaacga     780
tggcagcaca tggcagacac attactttct gtcaaggcca ttcaagatga agacaaggaa     840
ttggcacaac tcctcaccgg ttaccaggat atggttggct ttctgaatgt gcataaggtt    900
gcacgcatca acacacaggt tcctgtgatt cttgaggcaa caaccttttc aatcaagttg    960
caaaagcgac ggtatttggt tttagaatgt ctaaatcagg cccctgtcga tggttcaagt   1020
ggaacatcat atggcacgtc aggtggttgg tctagttcct ccaagacagg gaacctcgac   1080
ttttga                                                              1086
```

<210> SEQ ID NO 16
<211> LENGTH: 1086
<212> TYPE: DNA
<213> ORGANISM: Glycine max

<400> SEQUENCE: 16

-continued

| | |
|---|---|
| atggctgcaa ccagggctcg agttagtagc ttctctcgca atgtatcaac tgtgacttct | 60 |
| cagaatcatg gacttaagca tggccctaat gggacaatgt tcatttcatc tgggattcca | 120 |
| gatctggaca agattttagg tggtggtttt tctctgggta gccttgtcat ggttatggaa | 180 |
| gatcctgaag cacctcatca tatgcttcta ttgagaaatt ttatgtctca aggacttgtg | 240 |
| caaaaacagc cactcttgta tgctagtgca tctagagatc ctaaaagttt tctcggtact | 300 |
| ttgcctagtc cggcgtcacc caaaggggat aataaatctt cagatcttag ccatgaaaag | 360 |
| gatctaagaa tcgcttggca atacaaaaag tattttggtg agcctcagct aaatctgaac | 420 |
| actaataatg gtggtcagca tgattactgt aatgattttg acttgagaaa gcccctggac | 480 |
| cggcactttt ttagtggcaa taatgtagat tgtgttagca tcaaagattc tcctaacctt | 540 |
| actgctcttc aagattgttg tgctggattt ctagctaaat tctcaagaaa tgaaggcagc | 600 |
| atttcctctg ctggtcgtat tgcaattcaa tcattctgtt ctccacaatg caagtattca | 660 |
| aatgaggagt ggcatatgct ttcttttatt aggtccctaa agggcatggc ccggtcttca | 720 |
| aacgctgtta ttgttgtaac cttttccacct tcacttcttc ctccatcttg ttcaaaaaga | 780 |
| ttgcagcata tggcagacac cttgcttttct gtcaaagcca ttccagatga ggataaggaa | 840 |
| cttgcaaaac tcctcactgg ttaccaggat atgattgggc ttctaaatgt acacaaagtt | 900 |
| gcacggttaa atacacaggt tcctgtgatt ctggaggcca aacattctc cataaaattg | 960 |
| caaaaacgaa ggttttttggt tttagaatgt ctaaatcaag ccccagttga tggttcaagt | 1020 |
| ggcagttcgt atggcacatc tggcggttgt tctgggtcaa ctaaagctgg accacttgat | 1080 |
| ttttag | 1086 |

<210> SEQ ID NO 17
<211> LENGTH: 1350
<212> TYPE: DNA
<213> ORGANISM: Citrus sinensis

<400> SEQUENCE: 17

| | |
|---|---|
| atgaaagccg cccaaactcc acataaaaaa gaagtccctt gtgtgtttgg ccgcccgccg | 60 |
| cagctaccca tcaccaaaat aatccggctc tccgccgcac tactcgctcg tcaccggcgt | 120 |
| tgctcgacgc caactgctgc tctatcactc ccgccccgtg tctgctcttt gcggcctgaa | 180 |
| tcattaagct gcagattgtc aaccatttac tcttggcatt ttacaggcaa gacaaagctg | 240 |
| tgttctgttg atgctgccat ggcaacaact aagcctcggc taagcagctt ctctcgcaac | 300 |
| ctatcggctg tatcctcgtc tcaaaccccct ggagtcaaat gtggtcctaa tggaactatg | 360 |
| tttgttttcat ctgggatagc tgatcttgac aagatacttg tggtgggtt ccctttagga | 420 |
| agtcttgtga tggtgatgga agatgcagaa gcacctcatc acatgctttt gttaaggaat | 480 |
| tttatgtcac aagggcttgt tcacggccaa cctcttcttt acgccagtcc atccaaggac | 540 |
| cccagaggtt ttttgggtac tttgcctagt cctgcctctc tgaaacatga taaatctcgt | 600 |
| gatcgggaat cagaacagga aaagggattg aggatagctt ggcagtacaa gaagtatatg | 660 |
| ggtgaaaatc aaccaaactt tgatagccac agagacaata agcaagatta ctgcaatgag | 720 |
| tttgacttca gaaagccact ggagaggcac tattttacca gacaacgtgt aaattgtgtt | 780 |
| ggtatccaac actcaaaaaa tcttgctgct cttcaggagc attgtgcctc attttagct | 840 |
| caacatcaaa gaaatgacgg cagcagtgca ttggctggtc gtatagctat tcagtcatta | 900 |
| tgtgctccac aatgtgaaca ttccaacatg gattgggaaa tgctttcttt tattaaatct | 960 |
| ctgaaaggta tggtgcggtc ttcaaatgca gtggttgtta taaccttttcc gccctcccctt | 1020 |

| | |
|---|---|
| ctctcacttt cgtccactaa acgatggcag cacatggcag acactctgct ttctgttgca | 1080 |
| gctatcccag atgaggacaa ggaattggca aaactccttt ccggttatca ggacatggtt | 1140 |
| ggccttctta atgtacacaa agtagctcgt ttgaatacac aggtgccttt gatactcgag | 1200 |
| gcaacaacat tttcaataaa gttgcagaag cgtaggttct tggttttaga atgtctcaat | 1260 |
| caagctcctg ttgatggctc aagtgggagt tcatatggca catcaggtag ttgctctgga | 1320 |
| tcatccaagg ctgggaccct tgatttttag | 1350 |

<210> SEQ ID NO 18
<211> LENGTH: 1083
<212> TYPE: DNA
<213> ORGANISM: Solanum lycopersicum

<400> SEQUENCE: 18

| | |
|---|---|
| atggcttcaa gtagaccgcg cggcggcagt ttttccagaa acatatctag tgcagctaca | 60 |
| gcgcagattc ctggagttaa gcttggtcca aatggcacat catttctttc atcaggcata | 120 |
| ccagatcttg accagatttt gggtggtggc tttactttgg gaagcctagt catggttatg | 180 |
| gaagaccctg aggctcctca tcatatgctt ttactgagaa atttcatgtc tcagggtctg | 240 |
| attcacaagc aaccccctact ttatgccagc ccagaaagag atccacgagg atttcttgga | 300 |
| actttgccta gtccaatggc ttctaaggag gagaagtcta atgaacgacc ttcagaacag | 360 |
| gacgcgaatt taagaatcgc ttggcaatat aagaagtact ttggggaaca aacagaggtc | 420 |
| caaagaggtg ggaaagctga atattgcaac gactttgact tacgaaagcc cctagaaagg | 480 |
| cacttctata gtggacagcg ggttgattgc attagtcttc gagattctcc taatctagtg | 540 |
| cctctacttg aacgatgctc aaccttttca gctcaaatat caaaatctga tggcaacatc | 600 |
| acatgtgccg gtcgtattgc cattcagtcg ctatgttcac ctcagtgcga cttctctgac | 660 |
| aaggattggg agatgctctc ttttataaga tccttgaaag gcatggttcg atcttcaggt | 720 |
| gcagttgcgg tcatatcctt tccacccctca cttgtctcgc cagccttttt aaagaggtgg | 780 |
| cagcatctgg ctgataccct tgatatctgtc aaagcaattc ctgatgagga caaagaattg | 840 |
| gcgaaactcc taactggtta ccaagacatg ctgggccttc tgagtgtaca caaagtagct | 900 |
| cgcataaaata cacaggtccc tgcaattttg gaagcaacaa cattctcaat gaagctgcga | 960 |
| aagcgaagag cattggtttt agaatgcctt aatcaagccc cagttgatgg ctcaagtggt | 1020 |
| agttcatatg gtacttctgg tgcttgttct ggaagttcta agaccgggaa cctcgacttc | 1080 |
| tag | 1083 |

<210> SEQ ID NO 19
<211> LENGTH: 1050
<212> TYPE: DNA
<213> ORGANISM: Medicago truncatula

<400> SEQUENCE: 19

| | |
|---|---|
| atggctgcaa caaggactcg agttagtagc ttttctcgca atgtatcaac tgtaacgtct | 60 |
| cagaattcag gactcaagca cggccctaat gggacaacat tcctatcgtc tgggattcca | 120 |
| gatctcgaca agattttagg tggtggtttt tctcttggta gccttgtcat gattatggaa | 180 |
| gatgcagaag cacctcatca tatgcttcta ttgagaaatt tgatgtctca aggacttgta | 240 |
| cataaacagc cactgttgta tgctagtgct tcaagagacc ctaaaggatt tcttggtact | 300 |
| ttacctgctc cagccccagc caaagaggat aaaagtcaag atcttaccaa tgaaaaggat | 360 |

| | |
|---|---|
| ttgagaattg cttggcaata caagaagtac tttggtgccc aacatgatta ctgcaatgaa | 420 |
| tttgacttgc ggaagccttt ggatagacat ttttatagtg gcatgaatgt agattgtgtc | 480 |
| agcatccaag attctccaaa ccttgcttct cttcaagatc agtgtgctaa atttctatct | 540 |
| caattctcaa gaagtgaagc caatatttcc tccgctggcc gtattgcaat tcaatcattc | 600 |
| tgttctccac aatgcaaata cgcaaacatg gagtggcata tgctttcctt tattaggtcc | 660 |
| ctaaaaggca tggcacgatc ttcaaatgct gttgttgttg taacatttcc accttcactt | 720 |
| gtttctccat cttgttcaaa aagattgcaa catatggcag acaccttgct ttctgtcaga | 780 |
| gcaattccag atgaggacaa ggaaatggca aaacttctca ctggttacca agacatggtt | 840 |
| ggactgctta atatacataa agttgcacgg ttaaatacac aggttcccgt gattctcgag | 900 |
| gccacaacat tctcaataaa attgcaaaaa cgaaggtatt tggttctaga atgtctaaat | 960 |
| caagccccgg ttgacggttc aagtgggagt tcatataaca catctggtag ttgttctggg | 1020 |
| tcaactaaag ctgggtcact tgattttag | 1050 |

<210> SEQ ID NO 20
<211> LENGTH: 1089
<212> TYPE: DNA
<213> ORGANISM: Fragaria vesca

<400> SEQUENCE: 20

| | |
|---|---|
| atggctgcaa ccaagactcg gacgagtagc ttctctcgca attttctgg tgcaagctca | 60 |
| cctcaaatcc caggactcaa gcatggaccc aatggcacaa tgtttgtttc atccgggatt | 120 |
| ccagaccttg acaaaatttt agggggtggt tttgctctag aagcctagt catggtgatg | 180 |
| gaagatgcag aagcacctca tcatatgctt ttgcttagga atttcatgtc tcaaggactt | 240 |
| gttcacaacc aacatcttct ctatgcaagc ccagccaagg atccaagaca gtttcttggt | 300 |
| actttgccta gtccagccgt acccaaagat gaaaagtcta gtcatcgaga ccctgatcag | 360 |
| gagaaagggt tgaggatagc ttggcaatat aagaagtatt ttggtgaaaa tcagcagggt | 420 |
| tttgatagtc aaaatgggaa acatgagttc tgcaacaact ttgacttgcg gaagcccttg | 480 |
| gagaggcagt ttctaacggg caagctaata gaatgtgcta gcatacttga ttctccgaat | 540 |
| cttgtcacat ttcatgaccg ttgtgctact tttttatcac aatttccaag aaatgacagc | 600 |
| aacatttctt gtgttggtcg aattgccatt caatcattct gtgctccaca gtgtggatat | 660 |
| tccaacctgg aatgggacat gctttcctta cttagatctc tgaaaagcat gctacgatct | 720 |
| tcaaatgcag ttgctgttgt gacatttctg cctagtcttc tttcatcatc ctcctctaca | 780 |
| agatggcagc acattgcgga taccttgctg tcagttaaag cgcttccaga tgaggacaag | 840 |
| gaattggcaa ccctccttac tggttaccag gacatggttg gccttcttaa tgtgcagaaa | 900 |
| gttgcacaaa ttaacacgca ggttcctgtg attcttgatg caacaacctt ctcaataaag | 960 |
| ctgcaaaagc ggaggttttt ggttttagaa tgtctaaatc aggcccctgt cgatggttct | 1020 |
| agtgggagtt catatggcac ttctggtagt tgttctgggt cctctaagac tggatctctt | 1080 |
| gatttttag | 1089 |

<210> SEQ ID NO 21
<211> LENGTH: 1089
<212> TYPE: DNA
<213> ORGANISM: Cucumis melo

<400> SEQUENCE: 21

| | |
|---|---|
| atggcagcga caaagcctcg gacaggcagc ttttcacgca acttctcttc tgctcattca | 60 |

-continued

| | |
|---|---|
| tctaagacgc caggatataa acacggtccc aatggcacga cattcatctc atccggaata | 120 |
| ccagaccttg acaagattct tgtggtggg tttcctttgg gaagcttggt cttggtaatg | 180 |
| gaagatgcag aagctcctca tcacatgctt ttattgcgga atttatgtc tcagggactt | 240 |
| gttcacaacc aacctcttct ttatgctagt ccatccagag acccaagagg attcttgggt | 300 |
| actttgccga gcccagggc atccaaagat gacaaatctc gtgataattc ttctgaacag | 360 |
| gagaagggct tgaggattgc ttggcaatat aagaagtatt tggagatga tcaagagagc | 420 |
| accaatgcca ttgacagtaa atacgagttt tgcaatgact ttgatttgcg aaggccattt | 480 |
| gacagacatt ttttcagtgg aaagcatgtg aatgtgtta gtattctaga ttcttctagt | 540 |
| cttctaatt tcgcgatcg ctgcgccacg ttcctatcac aagttccaag aaatgatggc | 600 |
| aatatatcct ctgctggccg tattgccatt caatcattat gtgctccaca atgtgatcac | 660 |
| tccaacatgg aatgggaaat gctttccttt ttaaggtatc tgaaaagcat ggtaaggtcc | 720 |
| tcaaatgcag tagctgtagt gacgtttcca ccttctcttc tttcgccgtc cttctctaaa | 780 |
| agatggcagc acatggcgga taccttgctt tcagtcagag caatcccaga tgaggataag | 840 |
| gaattagcaa agctcctcac tggctaccaa gacatggttg gtcttctcaa tgtgcataaa | 900 |
| gtagctcaaa tcaatacaca ggttccaaag attcttgagg cgactacgtt ctctataaag | 960 |
| ttgcaaaaga gaaggtactt agttttagaa tgccttaatc aagcgcccat tgatgtttca | 1020 |
| agtggcagct catatggctc aactgggagt tgttctggct cctctaagac agcttctctc | 1080 |
| gagttttag | 1089 |

<210> SEQ ID NO 22
<211> LENGTH: 1128
<212> TYPE: DNA
<213> ORGANISM: Zea mays

<400> SEQUENCE: 22

| | |
|---|---|
| atggccgccg ccggtggccg aacccttggc cggagcagct tctcccgcgc cacatctaac | 60 |
| ctggtggcgt cctcatccgg cgcttctggc gttaagattg ccccgaacgg tgcttctttc | 120 |
| gtctcctcgg gcattcccga cctcgacagg attttgggtg gtggattcct tcttggctca | 180 |
| gttgtaatga tcatggagga cactgatgcg ccacaccacc tcttgcttct tcggtgcttc | 240 |
| atgtctcagg gtgttgtgca caaacaaccc ctgctctttt caggagctat gaaagagcct | 300 |
| gtgttgttcc ttggtacact acctgctcca gtttcatctt caaaggagga tggacgacac | 360 |
| agagcaatgg gtcctgcagc aagtagtgat ggacgagcaa atgatgaggg tttgaggata | 420 |
| gcttggcagt acaagaaata ctttggggat acaagacttc gcgagctga acataaagac | 480 |
| aataaacagg aattcagcaa tgattttgat ttgaggaagc ccttggaaag gcatttactt | 540 |
| aatggacaga atattgaatg tgtaagcact caagatgctg acacactcag cagcctccag | 600 |
| gattgttgtt ctgctttcgt atccaagctt ccaagaaaag atggtgggag ttcaactgct | 660 |
| gggagaattg ctatacaatc actctgtgca ccgcagtgca gatactttga aaaggactgg | 720 |
| gacatggtct catttatcag atcactgaag gccatggtgc gctcatctaa ctctgttgct | 780 |
| gttgtaacat ttccgagtac agttctgtca aattcgttct gtaagagatg cagcacctg | 840 |
| gcggatacac tgctgtccat caaagcaatt ccagatgagg acaaagactt ggcaaaactc | 900 |
| ctcacaggat atcaagatat ggttggtttt ttgcatgtcc acaaggtggc acaacctaac | 960 |
| agtcaggtcc ctgtgatctt agaggcatcc acgctctctc taaagctgcg aaagaggagg | 1020 |

```
tccctggtct tagaacggtt gaatcaggct ccagtcgatg ggtcaagtgg gccttcgtct    1080
gctgcatcaa gcagttgctc atcgcaaggt tcacagcttg atttctaa                 1128

<210> SEQ ID NO 23
<211> LENGTH: 1134
<212> TYPE: DNA
<213> ORGANISM: Oryza sativa

<400> SEQUENCE: 23
atggccgccg ccgccggagg ccagaccgtc ggccggagca gcttctctcg agcagcggca     60
cctcatgtgg cgtcctcatc caccgccgca ggagtcaagc ttggtcctaa tggcgccgcc    120
ttcgtctcct cgggcatccc cgacctcgac aggattctag gtggggtttt cttattgga    180 tcagttgtaa tgatcatgga ggactctgat gcgcctcacc acctcctact gcttcggagc    240
ttcatggcgc agggtgttgt gcacaaacaa ccgctgctct tcgcaggacc tatgaaggaa    300
ccccgcttgt tccttggtac attacctgct gttgcatctt caaaggagga tggacgacaa    360
agagggatgg gggctggaac aagtagcgat ggccgaacaa gtgacgaggc tttgaggata    420
gcttggcagt acaagaaata ctttggagaa gagaagactt ctcatgctga acacagagac    480
aacaagcaag aatttagcaa tgattttgat ttacggaagc ccttggaaag gcatttactt    540
aatgctcaga atattgaatg tgctagcact caagaaggag acactcttgg tgtcctccag    600
gaccgttgtt ccacattctt gtccaaactt ccgagaaaag atggtggaaa tgcgcatgct    660
ggacggattg ctatacaatc actatgtgca ccacaatgcg atactttga aaggactgg     720 gacatggtct catttatcag atcgctgaag gccatggttc gtgcatctaa tgcagttgct    780
gttataacat ttccaaatac agttttatca agctcctttt gtaagagatg cagcacctg    840 gcggacacac ttctgtcaat caaagcaatt ccagatgagg acaaagagtt agcaaaactc    900
ctcactggat atcaggatat ggttggtttt tacatgtgc ataaggtggc acagactaat    960
agccaggtcc ccgtcatatt ggaggcgtcc acgttttctc tgaagttgcg caagaggagg   1020
tcgctggtgt tagaacggtt gaatcaagct ccagtggatg gatcaggtgg tccttcactt   1080
gatgcatctg gcagttgctc ctcatcctca caaggttcac agcttgatt ctag          1134

<210> SEQ ID NO 24
<211> LENGTH: 1092
<212> TYPE: DNA
<213> ORGANISM: Eucalyptis grandis

<400> SEQUENCE: 24
atggctacac ccaagacgag ggccagcagt ttctcaagga acgtaccatc tacagcagcg     60
ccccaggtgc cggggtgaa gagtgggccg aacgggactc tcttttgtc ctctgggata    120 tcagacctcg acaagatatt aggaggcggc tttcctcttg ggagtttggt tgttgtcatg    180
gaagacccgg aggcgccgca tcatatgctc ttgttgagga atttcatgtc tcaaggactc    240
gttctcaatc aaccccttt gtacgcgagc cctgccaaag acccgagagg gtttctgggt    300
actttgccta gtcctgtgtc gtctaaagat gataagccgc tcaaccgtga ttcagaacag    360
gagaaaggct tgcggattgc ttggcagtac aagaagtatt tggagaaaaa tcagcagaat    420
tcaaatagcc aaagagataa taagttcgag ttctgcaatg agtttgatct gcggaagccc    480
ttgcaaaggc agtttctcag tggacagcgc gtagagtgta tgagcactca agattctcca    540
gatctcgctc tcttcatga tcgttgcgca acatttctaa aacagttttt cagaactgat    600
ggcaacattt cgggtgctgg ccgcattgca atccaatctt tttgtgccc acaatgtacc    660
```

```
tattttgaca aggaatggca tgttctttca ttcataagat cgctgagaag catgattagg      720
tcttcgaacg cagttgtaat tctgtccttc ccaccatcac tactttctcc ttctttctct      780
aaaagattgc agcatatggc agacacattg ctctcagtca gagcaattcc agatgaggac      840
aaagacttgg ccaaactcct cacgggctac caagacatga ttggacttct tagtgtacac      900
aaagtagcac gtattaatac acaggttcct atcattcttg aggcagcaac attctccata      960
aagttgcaaa agcgcaagtt tctggtgctt gaatgtttga atcaagctcc tgttgatggt     1020
tcaagtggca cgtcctatgc tacttctggg agctgttctg tttcgtctaa gggcgggtcc     1080
cttgacttct ag                                                         1092
```

<210> SEQ ID NO 25
<211> LENGTH: 565
<212> TYPE: PRT
<213> ORGANISM: Arabidopsis thaliana

<400> SEQUENCE: 25

Met Ala Thr Ala Val Met Asn Gly Glu Leu Lys Lys Gln Pro Arg
1               5                   10                  15

Pro Gly Lys Gly Gly Tyr Gln Gly Arg Gly Leu Thr Glu Glu Ala
            20                  25                  30

Arg Val Arg Ala Ile Ser Glu Ile Val Ser Thr Met Ile Glu Arg Ser
        35                  40                  45

His Arg Asn Glu Asn Val Asp Leu Asn Ala Ile Lys Thr Ala Ala Cys
    50                  55                  60

Arg Lys Tyr Gly Leu Ala Arg Ala Pro Lys Leu Val Glu Met Ile Ala
65                  70                  75                  80

Ala Leu Pro Asp Ser Glu Arg Glu Thr Leu Leu Pro Lys Leu Arg Ala
                85                  90                  95

Lys Pro Val Arg Thr Ala Ser Gly Ile Ala Val Val Ala Val Met Ser
            100                 105                 110

Lys Pro His Arg Cys Pro His Ile Ala Thr Thr Gly Asn Ile Cys Val
        115                 120                 125

Tyr Cys Pro Gly Gly Pro Asp Ser Asp Phe Glu Tyr Ser Thr Gln Ser
        130                 135                 140

Tyr Thr Gly Tyr Glu Pro Thr Ser Met Arg Ala Ile Arg Ala Arg Tyr
145                 150                 155                 160

Asn Pro Tyr Val Gln Ala Arg Ser Arg Ile Asp Gln Leu Lys Arg Leu
                165                 170                 175

Gly His Ser Val Asp Lys Val Glu Phe Ile Leu Met Gly Gly Thr Phe
            180                 185                 190

Met Ser Leu Pro Ala Glu Tyr Arg Asp Phe Phe Ile Arg Asn Leu His
        195                 200                 205

Asp Ala Leu Ser Gly His Thr Ser Ala Asn Val Glu Glu Ala Val Ala
    210                 215                 220

Tyr Ser Glu His Ser Ala Thr Lys Cys Ile Gly Met Thr Ile Glu Thr
225                 230                 235                 240

Arg Pro Asp Tyr Cys Leu Gly Pro His Leu Arg Gln Met Leu Ile Tyr
                245                 250                 255

Gly Cys Thr Arg Leu Glu Ile Gly Val Gln Ser Thr Tyr Glu Asp Val
            260                 265                 270

Ala Arg Asp Thr Asn Arg Gly His Thr Val Ala Val Ala Asp Cys
        275                 280                 285

-continued

Phe Cys Leu Ala Lys Asp Ala Gly Phe Lys Val Val Ala His Met Met
    290                 295                 300

Pro Asp Leu Pro Asn Val Gly Val Glu Arg Asp Met Glu Ser Phe Lys
305                 310                 315                 320

Glu Phe Phe Glu Ser Pro Ser Phe Arg Ala Asp Gly Leu Lys Ile Tyr
                325                 330                 335

Pro Thr Leu Val Ile Arg Gly Thr Gly Leu Tyr Glu Leu Trp Lys Thr
                340                 345                 350

Gly Arg Tyr Arg Asn Tyr Pro Pro Glu Gln Leu Val Asp Ile Val Ala
            355                 360                 365

Arg Ile Leu Ser Met Val Pro Pro Trp Thr Val Tyr Arg Val Gln
370                 375                 380

Arg Asp Ile Pro Met Pro Leu Val Thr Ser Gly Val Glu Lys Gly Asn
385                 390                 395                 400

Leu Arg Glu Leu Ala Leu Ala Arg Met Asp Asp Leu Gly Leu Lys Cys
                405                 410                 415

Arg Asp Val Arg Thr Arg Glu Ala Gly Ile Gln Asp Ile His His Lys
            420                 425                 430

Ile Lys Pro Glu Gln Val Glu Leu Val Arg Arg Asp Tyr Thr Ala Asn
            435                 440                 445

Glu Gly Trp Glu Thr Phe Leu Ser Tyr Glu Asp Thr Arg Gln Asp Ile
    450                 455                 460

Leu Val Gly Leu Leu Arg Leu Arg Lys Cys Gly Lys Asn Val Thr Cys
465                 470                 475                 480

Pro Glu Leu Met Gly Lys Cys Ser Val Val Arg Glu Leu His Val Tyr
                485                 490                 495

Gly Thr Ala Val Pro Val His Gly Arg Asp Ala Asp Lys Leu Gln His
            500                 505                 510

Gln Gly Tyr Gly Thr Leu Leu Met Glu Glu Ala Glu Arg Ile Ala Arg
        515                 520                 525

Arg Glu His Arg Ser Asn Lys Ile Gly Val Ile Ser Gly Val Gly Thr
530                 535                 540

Arg His Tyr Tyr Arg Lys Leu Gly Tyr Glu Leu Glu Gly Pro Tyr Met
545                 550                 555                 560

Val Lys His Leu Leu
                565

<210> SEQ ID NO 26
<211> LENGTH: 565
<212> TYPE: PRT
<213> ORGANISM: Brassica napus

<400> SEQUENCE: 26

Met Ala Thr Ala Ile Val Met Asn Gly Glu Ser Lys Lys Gln Pro Arg
1               5                   10                  15

Pro Gly Arg Gly Gly Phe Gln Gly Arg Gly Leu Thr Glu Glu Glu Ala
                20                  25                  30

Arg Val Arg Ala Ile Ser Glu Ile Val Ser Thr Met Ile Glu Arg Ser
            35                  40                  45

His Arg Asn Glu Asn Val Asp Leu Asn Ala Ile Lys Thr Gln Ala Cys
        50                  55                  60

Arg Lys Tyr Gly Leu Ala Arg Ala Pro Lys Leu Val Glu Met Ile Ala
65                  70                  75                  80

Ala Leu Pro Asp Ser Glu Arg Glu Thr Leu Leu Pro Lys Leu Arg Ala
                85                  90                  95

-continued

```
Lys Pro Val Arg Thr Ala Ser Gly Ile Ala Val Val Ala Val Met Ser
                100                 105                 110
Lys Pro His Arg Cys Pro His Ile Ala Thr Thr Gly Asn Ile Cys Val
            115                 120                 125
Tyr Cys Pro Gly Gly Pro Asp Ser Asp Phe Glu Tyr Ser Thr Gln Ser
130                 135                 140
Tyr Thr Gly Tyr Glu Pro Thr Ser Met Arg Ala Ile Arg Ala Arg Tyr
145                 150                 155                 160
Asn Pro Tyr Val Gln Ala Arg Ser Arg Ile Asp Gln Leu Lys Arg Leu
                165                 170                 175
Gly His Ser Val Asp Lys Val Glu Phe Ile Leu Met Gly Gly Thr Phe
            180                 185                 190
Met Ser Leu Pro Ala Glu Tyr Arg Asp Phe Phe Ile Arg Asn Leu His
        195                 200                 205
Asp Ala Leu Ser Gly Tyr Thr Ser Ala Asn Val Glu Glu Ala Val Thr
210                 215                 220
Tyr Ser Glu His Ser Ala Thr Lys Cys Ile Gly Met Thr Ile Glu Thr
225                 230                 235                 240
Arg Pro Asp Tyr Cys Leu Gly Pro His Leu Arg Gln Met Leu Thr Tyr
                245                 250                 255
Gly Cys Thr Arg Leu Glu Ile Gly Val Gln Ser Thr Tyr Glu Asp Val
            260                 265                 270
Ala Arg Asp Thr Asn Arg Gly His Thr Val Ala Ala Val Ala Asp Cys
        275                 280                 285
Phe Cys Leu Ala Lys Asp Ala Gly Phe Lys Val Val Ala His Met Met
290                 295                 300
Pro Asp Leu Pro Asn Val Gly Val Glu Arg Asp Met Glu Ser Phe Lys
305                 310                 315                 320
Glu Phe Phe Glu Ser Pro Ser Phe Arg Ala Asp Gly Leu Lys Ile Tyr
                325                 330                 335
Pro Thr Leu Val Ile Arg Gly Thr Gly Leu Tyr Glu Leu Trp Lys Thr
            340                 345                 350
Gly Arg Tyr Arg Asn Tyr Pro Pro Glu Gln Leu Val Asp Ile Val Ala
        355                 360                 365
Arg Ile Leu Ser Met Val Pro Pro Trp Thr Arg Val Tyr Arg Val Gln
370                 375                 380
Arg Asp Ile Pro Met Pro Leu Val Thr Ser Gly Val Glu Lys Gly Asn
385                 390                 395                 400
Leu Arg Glu Leu Ala Leu Ala Arg Met Asp Asp Leu Gly Leu Lys Cys
                405                 410                 415
Arg Asp Val Arg Thr Arg Glu Ala Gly Ile Gln Asp Ile His His Lys
            420                 425                 430
Ile Lys Pro Glu Gln Val Glu Leu Val Arg Arg Asp Tyr Thr Ala Asn
        435                 440                 445
Gln Gly Trp Glu Thr Phe Leu Ser Tyr Glu Asp Thr Arg Gln Asp Ile
450                 455                 460
Leu Val Gly Leu Leu Arg Leu Arg Lys Cys Gly Lys Asn Val Thr Cys
465                 470                 475                 480
Pro Glu Leu Met Gly Lys Cys Ser Val Val Arg Glu Leu His Val Tyr
                485                 490                 495
Gly Thr Ala Val Pro Val His Gly Arg Glu Ala Asp Lys Leu Gln His
            500                 505                 510
```

-continued

Gln Gly Tyr Gly Thr Leu Leu Met Glu Glu Ala Glu Arg Ile Ala Arg
            515                 520                 525

Arg Glu His Arg Ser Asn Lys Ile Gly Val Ile Ser Gly Val Gly Thr
530                 535                 540

Arg His Tyr Tyr Arg Lys Leu Gly Tyr Glu Leu Glu Gly Pro Tyr Met
545                 550                 555                 560

Val Lys His Leu Leu
                565

<210> SEQ ID NO 27
<211> LENGTH: 565
<212> TYPE: PRT
<213> ORGANISM: Gossypium arboreum

<400> SEQUENCE: 27

Met Ala Thr Ala Ala Ile Asp Pro Glu Leu Lys Lys Leu Pro Arg Pro
1               5                   10                  15

Gly Arg Gly Gly Phe Gln Ala His Gly Leu Thr Glu Glu Ala Arg
            20                  25                  30

Val Arg Ala Ile Ala Glu Ile Val Asn Ser Met Val Glu Leu Ser Arg
        35                  40                  45

Lys Asn Gln Arg Val Asp Leu Asn Ala Ile Lys Ser Ala Ala Cys Arg
    50                  55                  60

Lys Tyr Gly Leu Ala Arg Ala Pro Lys Leu Val Glu Met Ile Ala Ala
65                  70                  75                  80

Leu Pro Glu Ser Glu Arg Val Ser Leu Leu Pro Lys Leu Arg Ala Lys
                85                  90                  95

Pro Val Arg Thr Ala Ser Gly Ile Ala Val Val Ala Val Met Ser Lys
            100                 105                 110

Pro His Arg Cys Pro His Ile Ala Thr Thr Gly Asn Ile Cys Val Tyr
        115                 120                 125

Cys Pro Gly Gly Pro Asp Ser Asp Phe Glu Tyr Ser Thr Gln Ser Tyr
    130                 135                 140

Thr Gly Tyr Glu Pro Thr Ser Met Arg Ala Ile Arg Ala Arg Tyr Asn
145                 150                 155                 160

Pro Tyr Val Gln Ala Arg Ser Arg Ile Asp Gln Leu Lys Arg Leu Gly
                165                 170                 175

His Ser Val Asp Lys Val Glu Phe Ile Leu Met Gly Gly Thr Phe Met
            180                 185                 190

Ser Leu Pro Ala Asp Tyr Arg Asp Tyr Phe Ile Arg Asn Leu His Asp
        195                 200                 205

Ala Leu Ser Gly His Thr Ser Ala Asn Val Glu Glu Ala Val Thr Tyr
    210                 215                 220

Ser Glu His Ser Ala Val Lys Cys Ile Gly Met Thr Ile Glu Thr Arg
225                 230                 235                 240

Pro Asp Tyr Cys Leu Gly Pro His Leu Arg Gln Met Leu Ser Tyr Gly
                245                 250                 255

Cys Thr Arg Leu Glu Ile Gly Val Gln Ser Thr Tyr Glu Asp Val Ala
            260                 265                 270

Arg Asp Thr Asn Arg Gly His Thr Val Ala Ala Val Ala Asp Cys Phe
        275                 280                 285

Cys Leu Ala Lys Asp Ala Gly Phe Lys Val Val Ala His Met Met Pro
    290                 295                 300

Asp Leu Pro Asn Val Gly Val Glu Arg Asp Leu Glu Ser Phe Lys Glu
305                 310                 315                 320

Phe Phe Glu Ser Pro Leu Phe Arg Ala Asp Gly Leu Lys Ile Tyr Pro
            325                 330                 335

Thr Leu Val Ile Arg Gly Thr Gly Leu Tyr Glu Leu Trp Lys Thr Gly
        340                 345                 350

Arg Tyr Arg Asn Tyr Pro Pro Glu Gln Leu Val Asp Ile Val Ala Arg
            355                 360                 365

Ile Leu Ala Met Val Pro Pro Trp Thr Arg Val Tyr Arg Val Gln Arg
    370                 375                 380

Asp Ile Pro Met Pro Leu Val Thr Ser Gly Val Glu Lys Gly Asn Leu
385                 390                 395                 400

Arg Glu Leu Ala Leu Ala Arg Met Asp Asp Leu Gly Leu Lys Cys Arg
                405                 410                 415

Asp Val Arg Thr Arg Glu Ala Gly Ile Gln Asp Ile His His Lys Ile
            420                 425                 430

Lys Pro Glu Glu Val Glu Leu Val Arg Arg Asp Tyr Thr Ala Asn Glu
        435                 440                 445

Ser Trp Glu Thr Phe Leu Ser Tyr Glu Asp Thr Arg Gln Asp Ile Leu
    450                 455                 460

Val Gly Leu Leu Arg Leu Arg Lys Cys Gly Gln Asn Thr Thr Cys Pro
465                 470                 475                 480

Glu Leu Met Gly Lys Cys Ser Ile Val Arg Glu Leu His Val Tyr Gly
                485                 490                 495

Thr Ala Val Pro Val His Gly Arg Asp Ala Asp Lys Leu Gln His Gln
            500                 505                 510

Gly Tyr Gly Thr Leu Leu Met Glu Glu Ala Glu Arg Ile Ala Arg Arg
        515                 520                 525

Glu His Arg Ser Thr Lys Ile Ala Val Ile Ser Gly Val Gly Thr Arg
    530                 535                 540

His Tyr Tyr Arg Lys Leu Gly Tyr Glu Leu Asp Gly Pro Tyr Met Val
545                 550                 555                 560

Lys Tyr Leu Thr Ser
            565

<210> SEQ ID NO 28
<211> LENGTH: 564
<212> TYPE: PRT
<213> ORGANISM: Glycine max

<400> SEQUENCE: 28

Met Ala Ala Ala Val Ala Glu Val Arg Lys Ala Pro Arg Pro Gly
1               5                   10                  15

Lys Gly Gly Tyr Glu Ala His Gly Leu Ser Glu Glu Ala Arg Val
            20                  25                  30

Arg Ala Ile Ala Glu Ile Val Ser Ser Met Val Asp Leu Ser His Lys
        35                  40                  45

Gly Gln Asn Val Asp Leu Asn Ala Leu Lys Ser Ala Cys Arg Lys
    50                  55                  60

Tyr Gly Leu Ser Arg Ala Pro Lys Leu Val Glu Met Ile Ala Ala Leu
65                  70                  75                  80

Pro Asp Ala Glu Arg Glu Thr Leu Leu Pro Lys Leu Arg Ala Lys Pro
                85                  90                  95

Val Arg Thr Ala Ser Gly Ile Ala Val Val Ala Val Met Ser Lys Pro
            100                 105                 110

His Arg Cys Pro His Ile Ala Thr Thr Gly Asn Ile Cys Val Tyr Cys

```
            115                 120                 125
Pro Gly Gly Pro Asp Ser Asp Phe Glu Tyr Ser Thr Gln Ser Tyr Thr
            130                 135                 140
Gly Tyr Glu Pro Thr Ser Met Arg Ala Ile Arg Ala Arg Tyr Asn Pro
145                 150                 155                 160
Tyr Val Gln Ala Arg Ser Arg Ile Asp Gln Leu Lys Arg Leu Gly His
                    165                 170                 175
Ser Val Asp Lys Val Glu Phe Ile Leu Met Gly Gly Thr Phe Met Ser
                180                 185                 190
Leu Pro Ala Asp Tyr Arg Asp Tyr Phe Ile Arg Asn Leu His Asp Ala
                195                 200                 205
Leu Ser Gly His Thr Ser Ala Asn Val Glu Glu Ala Val Ala Tyr Ser
            210                 215                 220
Glu His Gly Ala Thr Lys Cys Ile Gly Met Thr Ile Glu Thr Arg Pro
225                 230                 235                 240
Asp Tyr Cys Leu Gly Pro His Leu Arg Gln Met Leu Ser Tyr Gly Cys
                    245                 250                 255
Thr Arg Leu Glu Ile Gly Val Gln Ser Thr Tyr Glu Asp Val Ala Arg
                260                 265                 270
Asp Thr Asn Arg Gly His Thr Val Ala Ala Val Ala Asp Cys Phe Cys
                275                 280                 285
Leu Ala Lys Asp Ala Gly Phe Lys Val Val Ala His Met Met Pro Asp
290                 295                 300
Leu Pro Asn Val Gly Val Glu Arg Asp Met Glu Ser Phe Arg Glu Phe
305                 310                 315                 320
Phe Glu Ser Pro Met Phe Arg Ala Asp Gly Leu Lys Ile Tyr Pro Thr
                    325                 330                 335
Leu Val Ile Arg Gly Thr Gly Leu Tyr Glu Leu Trp Lys Thr Gly Arg
                340                 345                 350
Tyr Arg Asn Tyr Pro Pro Glu Gln Leu Val Asp Ile Ile Ala Arg Ile
                355                 360                 365
Leu Ala Met Val Pro Pro Trp Thr Arg Val Tyr Arg Val Gln Arg Asp
            370                 375                 380
Ile Pro Met Pro Leu Val Thr Ser Gly Val Glu Lys Gly Asn Leu Arg
385                 390                 395                 400
Glu Leu Ala Leu Ala Arg Met Asp Asp Leu Gly Leu Lys Cys Arg Asp
                    405                 410                 415
Val Arg Thr Arg Glu Ala Gly Ile Gln Asp Ile His His Gln Ile Lys
                420                 425                 430
Pro Glu Glu Val Glu Leu Val Arg Arg Asp Tyr Met Ala Asn Glu Gly
                435                 440                 445
Trp Glu Thr Phe Leu Ser Tyr Glu Asp Thr Arg Gln Asp Ile Leu Val
            450                 455                 460
Gly Leu Leu Arg Leu Arg Lys Cys Gly Arg Asn Thr Thr Cys Pro Glu
465                 470                 475                 480
Leu Met Gly Lys Cys Ser Ile Val Arg Glu Leu His Val Tyr Gly Thr
                    485                 490                 495
Ala Val Pro Val His Gly Arg Asp Ala Asp Lys Leu Gln His Gln Gly
                500                 505                 510
Tyr Gly Thr Leu Leu Met Glu Glu Ala Glu Arg Ile Ala Cys Arg Glu
                515                 520                 525
His Arg Ser Thr Lys Ile Ala Val Ile Ser Gly Val Gly Thr Arg His
            530                 535                 540
```

Tyr Tyr Arg Lys Leu Gly Tyr Glu Leu Glu Gly Pro Tyr Met Val Lys
545                 550                 555                 560

Tyr Leu Val Lys

<210> SEQ ID NO 29
<211> LENGTH: 564
<212> TYPE: PRT
<213> ORGANISM: Citrus sinensis

<400> SEQUENCE: 29

Met Ala Thr Ala Val Leu Pro Gln Asp Thr Lys Lys Leu Pro Arg Pro
1               5                   10                  15

Gly Arg Gly Gly Phe Gln Ala His Gly Leu Thr Glu Glu Ala Arg
            20                  25                  30

Val Arg Ala Ile Ala Glu Ile Val Asn Ser Met Val Glu Leu Ser Arg
                35                  40                  45

Lys Asn Glu Thr Val Asp Leu Asn Ala Ile Lys Ser Ala Ala Cys Arg
50                  55                  60

Lys Tyr Gly Leu Ala Arg Ala Pro Lys Leu Val Glu Met Ile Ala Ala
65                  70                  75                  80

Leu Pro Glu Asn Asp Arg Glu Ala Leu Leu Pro Lys Leu Arg Ala Lys
                85                  90                  95

Pro Val Arg Thr Ala Ser Gly Ile Ala Val Val Ala Ile Met Ser Lys
            100                 105                 110

Pro His Arg Cys Pro His Ile Ala Thr Thr Gly Asn Ile Cys Val Tyr
        115                 120                 125

Cys Pro Gly Gly Pro Asp Ser Asp Phe Glu Tyr Ser Thr Gln Ser Tyr
130                 135                 140

Thr Gly Tyr Glu Pro Thr Ser Met Arg Ala Ile Arg Ala Arg Tyr Asn
145                 150                 155                 160

Pro Tyr Val Gln Ala Arg Ser Arg Ile Asp Gln Leu Lys Arg Leu Gly
                165                 170                 175

His Ser Val Asp Lys Val Glu Phe Ile Leu Met Gly Gly Thr Phe Met
            180                 185                 190

Ser Leu Pro Ala Asp Tyr Arg Asp Tyr Phe Ile Arg Asn Leu His Asp
        195                 200                 205

Ala Leu Ser Gly His Thr Ser Ala Asn Val Glu Glu Ala Val Thr Tyr
210                 215                 220

Ser Glu His Gly Ala Thr Lys Cys Ile Gly Met Thr Ile Glu Thr Arg
225                 230                 235                 240

Pro Asp Tyr Cys Leu Gly Pro His Leu Arg Gln Met Leu Ser Tyr Gly
                245                 250                 255

Cys Thr Arg Leu Glu Ile Gly Val Gln Ser Thr Tyr Glu Asp Val Ala
            260                 265                 270

Arg Asp Thr Asn Arg Gly His Thr Val Ala Ala Val Ala Asp Cys Phe
        275                 280                 285

Cys Leu Ala Lys Asp Ala Gly Phe Lys Val Val Ala His Met Met Pro
290                 295                 300

Asp Leu Pro Asn Val Gly Val Glu Arg Asp Leu Glu Ser Phe Arg Glu
305                 310                 315                 320

Phe Phe Glu Ser Pro Leu Phe Arg Ala Asp Gly Leu Lys Ile Tyr Pro
                325                 330                 335

Thr Leu Val Ile Arg Gly Thr Gly Leu Tyr Glu Leu Trp Lys Thr Gly
            340                 345                 350

```
Arg Tyr Arg Asn Tyr Pro Pro Glu Gln Leu Val Asp Ile Val Ala Arg
            355                 360                 365

Ile Leu Ala Met Val Pro Pro Trp Thr Arg Val Tyr Arg Val Gln Arg
        370                 375                 380

Asp Ile Pro Met Pro Leu Val Thr Ser Gly Val Glu Lys Gly Asn Leu
385                 390                 395                 400

Arg Glu Leu Ala Leu Ala Arg Met Asp Asp Leu Gly Leu Lys Cys Arg
                405                 410                 415

Asp Val Arg Thr Arg Glu Ala Gly Ile Gln Asp Ile His His Gln Ile
                420                 425                 430

Lys Pro Glu Glu Val Glu Leu Val Arg Arg Asp Tyr Val Ala Asn Glu
                435                 440                 445

Gly Trp Glu Thr Phe Leu Ser Tyr Glu Asp Thr Arg Gln Asp Ile Leu
        450                 455                 460

Val Gly Leu Leu Arg Leu Arg Lys Cys Gly Arg Asn Val Thr Cys Pro
465                 470                 475                 480

Glu Leu Met Gly Lys Cys Ser Ile Val Arg Glu Leu His Val Tyr Gly
                485                 490                 495

Thr Ala Val Pro Val His Gly Arg Glu Ala Asp Lys Leu Gln His Gln
                500                 505                 510

Gly Tyr Gly Thr Leu Leu Met Glu Glu Ala Glu Arg Ile Ala Leu Arg
        515                 520                 525

Glu His Arg Ser Arg Lys Met Ala Val Ile Ser Gly Val Gly Thr Arg
        530                 535                 540

His Tyr Tyr Arg Lys Leu Gly Tyr Glu Leu Glu Gly Pro Tyr Met Val
545                 550                 555                 560

Lys Tyr Leu Glu

<210> SEQ ID NO 30
<211> LENGTH: 565
<212> TYPE: PRT
<213> ORGANISM: Solanum lycopersicum

<400> SEQUENCE: 30

Met Ala Ala Ala Val Ala Val Ala Glu Thr Arg Lys Leu Pro Arg
1               5                   10                  15

Pro Gly Arg Gly Val Val Ser Leu Gly Leu Thr Glu Glu Ala
        20                  25                  30

Arg Val Arg Ala Ile Thr Glu Ile Val Asn Asn Met Val Glu Leu Ser
            35                  40                  45

Arg Lys Gly Lys Asp Val Asp Leu Asn Ala Leu Lys Ser Ala Ala Cys
        50                  55                  60

Arg Lys Tyr Gly Leu Ser Arg Ala Pro Lys Leu Val Glu Met Ile Ala
65                  70                  75                  80

Ala Leu Pro Asp Ser Glu Arg Glu Thr Leu Leu Pro Lys Leu Arg Ala
                85                  90                  95

Lys Pro Val Arg Thr Ala Ser Gly Ile Ala Val Val Ala Val Met Ser
                100                 105                 110

Lys Pro His Arg Cys Pro His Ile Ala Thr Thr Gly Asn Ile Cys Val
            115                 120                 125

Tyr Cys Pro Gly Gly Pro Asp Ser Asp Phe Glu Tyr Ser Thr Gln Ser
        130                 135                 140

Tyr Thr Gly Tyr Glu Pro Thr Ser Met Arg Ala Ile Arg Ala Arg Tyr
145                 150                 155                 160
```

-continued

```
Asn Pro Tyr Val Gln Ala Arg Ser Arg Ile Asp Gln Leu Lys Arg Leu
            165                 170                 175

Gly His Ser Val Asp Lys Val Glu Phe Ile Leu Met Gly Gly Thr Phe
        180                 185                 190

Met Ser Leu Pro Ala Glu Tyr Arg Asp Tyr Phe Thr Arg Asn Leu His
    195                 200                 205

Asp Ala Leu Ser Gly His Thr Ser Ala Asn Val Glu Glu Ala Val Ala
210                 215                 220

Tyr Ser Glu His Gly Ala Thr Lys Cys Ile Gly Met Thr Ile Glu Thr
225                 230                 235                 240

Arg Pro Asp Tyr Cys Leu Gly Pro His Leu Arg Gln Met Leu Ser Tyr
                245                 250                 255

Gly Cys Thr Arg Leu Glu Ile Gly Val Gln Ser Thr Tyr Glu Asp Val
            260                 265                 270

Ala Arg Asp Thr Asn Arg Gly His Thr Val Ala Ala Val Ala Asp Cys
        275                 280                 285

Phe Cys Leu Ala Lys Asp Ala Gly Phe Lys Val Val Ala His Met Met
    290                 295                 300

Pro Asp Leu Pro Asn Val Gly Val Glu Arg Asp Leu Glu Ser Phe Lys
305                 310                 315                 320

Glu Phe Phe Glu Ser Pro Ser Phe Arg Thr Asp Gly Leu Lys Ile Tyr
                325                 330                 335

Pro Thr Leu Val Ile Arg Gly Thr Gly Leu Tyr Glu Leu Trp Lys Thr
            340                 345                 350

Gly Arg Tyr Arg Asn Tyr Pro Pro Glu Gln Leu Val Asp Ile Val Ala
        355                 360                 365

Arg Ile Leu Ser Met Val Pro Pro Trp Thr Arg Val Tyr Arg Val Gln
    370                 375                 380

Arg Asp Ile Pro Met Pro Leu Val Thr Ser Gly Val Glu Lys Gly Asn
385                 390                 395                 400

Leu Arg Glu Leu Ala Leu Ala Arg Met Asp Asp Leu Gly Leu Lys Cys
                405                 410                 415

Arg Asp Val Arg Thr Arg Glu Ala Gly Ile Gln Asp Ile His Asn Lys
            420                 425                 430

Ile Arg Pro Glu Glu Val Glu Leu Val Arg Arg Asp Tyr Thr Ala Asn
        435                 440                 445

Glu Gly Trp Glu Thr Phe Leu Ser Tyr Glu Asp Thr Arg Gln Asp Ile
    450                 455                 460

Leu Val Gly Leu Leu Arg Leu Arg Lys Cys Gly Arg Asn Val Thr Cys
465                 470                 475                 480

Pro Glu Leu Thr Gly Arg Cys Ser Ile Val Arg Glu Leu His Val Tyr
                485                 490                 495

Gly Thr Ala Val Pro Val His Gly Arg Asp Thr Asp Lys Leu Gln His
            500                 505                 510

Gln Gly Tyr Gly Thr Leu Leu Met Glu Glu Ala Glu Arg Ile Ala Arg
        515                 520                 525

Arg Glu His Arg Ser Thr Lys Ile Ala Val Ile Ser Gly Val Gly Thr
    530                 535                 540

Arg His Tyr Tyr Arg Lys Leu Gly Tyr Glu Leu Glu Gly Pro Tyr Met
545                 550                 555                 560

Val Lys Asn Leu Val
            565
```

<210> SEQ ID NO 31
<211> LENGTH: 563
<212> TYPE: PRT
<213> ORGANISM: Medicago truncatula

<400> SEQUENCE: 31

```
Met Ala Ala Ala Met Val Ala Glu Gly Lys Lys Ala Pro Arg Pro Gly
1               5                   10                  15

Lys Gly Gly Phe Glu Gly His Gly Leu Ser Glu Glu Ala Arg Val
            20                  25                  30

Arg Ala Ile Ala Glu Ile Val Asn Ser Met Val Asp Leu Ser His Lys
            35                  40                  45

Gly His Lys Val Asp Leu Asn Ala Leu Lys Ser Ala Ala Cys Arg Lys
        50                  55                  60

Tyr Gly Leu Ser Arg Ala Pro Lys Leu Val Glu Met Ile Ala Ala Leu
65                  70                  75                  80

Pro Asp Ser Glu Arg Glu Val Leu Leu Pro Lys Leu Arg Ala Lys Pro
                85                  90                  95

Val Arg Thr Ala Ser Gly Ile Ala Val Val Ala Val Met Ser Lys Pro
            100                 105                 110

His Arg Cys Pro His Ile Ala Thr Thr Gly Asn Ile Cys Val Tyr Cys
        115                 120                 125

Pro Gly Gly Pro Asp Ser Asp Phe Glu Tyr Ser Thr Gln Ser Tyr Thr
    130                 135                 140

Gly Tyr Glu Pro Thr Ser Met Arg Ala Ile Arg Ala Arg Tyr Asn Pro
145                 150                 155                 160

Tyr Val Gln Thr Arg Gly Arg Ile Asp Gln Leu Lys Arg Leu Gly His
                165                 170                 175

Ser Val Asp Lys Val Glu Phe Ile Leu Met Gly Gly Thr Phe Met Ser
            180                 185                 190

Leu Pro Ala Asp Tyr Arg Asp Tyr Phe Thr Arg Asn Leu His Asp Ala
        195                 200                 205

Leu Ser Gly His Thr Ser Ala Asn Val Glu Glu Ala Val Met Tyr Ser
    210                 215                 220

Glu His Ser Ala Thr Lys Cys Ile Gly Met Thr Ile Glu Thr Arg Pro
225                 230                 235                 240

Asp Tyr Cys Leu Gly Pro His Leu Arg Gln Met Leu Ser Tyr Gly Cys
                245                 250                 255

Thr Arg Leu Glu Ile Gly Val Gln Ser Thr Tyr Glu Asp Val Ala Arg
            260                 265                 270

Asp Thr Asn Arg Gly His Thr Val Ala Ala Val Ala Asp Cys Phe Cys
        275                 280                 285

Leu Ala Lys Asp Ala Gly Phe Lys Val Val Ala His Met Met Pro Asp
    290                 295                 300

Leu Pro Asn Val Gly Val Glu Arg Asp Met Glu Ser Phe Arg Glu Phe
305                 310                 315                 320

Phe Glu Ser Pro Leu Phe Arg Thr Asp Gly Leu Lys Ile Tyr Pro Thr
                325                 330                 335

Leu Val Ile Arg Gly Thr Gly Leu Tyr Glu Leu Trp Lys Thr Gly Arg
            340                 345                 350

Tyr Arg Asn Tyr Pro Pro Glu Gln Leu Val Asp Ile Ile Ala Arg Ile
        355                 360                 365

Leu Ala Met Val Pro Pro Trp Thr Arg Val Tyr Arg Val Gln Arg Asp
    370                 375                 380
```

```
Ile Pro Met Pro Leu Val Thr Ser Gly Val Glu Lys Gly Asn Leu Arg
385                 390                 395                 400

Glu Leu Ala Leu Ala Arg Met Glu Asp Leu Gly Leu Lys Cys Arg Asp
            405                 410                 415

Val Arg Thr Arg Glu Ala Gly Ile Gln Asp Ile His His Gln Ile Lys
        420                 425                 430

Pro Glu Glu Val Glu Leu Val Arg Arg Asp Tyr Met Ala Asn Glu Gly
    435                 440                 445

Trp Glu Thr Phe Leu Ser Tyr Glu Asp Thr Arg Gln Asp Ile Leu Val
450                 455                 460

Gly Leu Leu Arg Leu Arg Lys Cys Gly Arg Asn Thr Thr Cys Pro Glu
465                 470                 475                 480

Leu Met Gly Lys Cys Ser Ile Val Arg Glu Leu His Val Tyr Gly Thr
                485                 490                 495

Ala Val Pro Val His Gly Arg Asp Ser Asp Lys Leu Gln His Gln Gly
            500                 505                 510

Tyr Gly Thr Leu Leu Met Glu Glu Ala Glu Arg Ile Ala Ser Lys Glu
        515                 520                 525

His Arg Ser Thr Lys Ile Ala Val Ile Ser Gly Val Gly Thr Arg His
    530                 535                 540

Tyr Tyr Arg Lys Leu Gly Tyr Glu Leu Glu Gly Pro Tyr Met Met Lys
545                 550                 555                 560

Tyr Leu Leu

<210> SEQ ID NO 32
<211> LENGTH: 567
<212> TYPE: PRT
<213> ORGANISM: Fragaria vesca

<400> SEQUENCE: 32

Met Ala Thr Ala Val Val Ala Ala Ala Asp Pro Ile Arg Lys Gln
1               5                   10                  15

Pro Arg Pro Gly Arg Gly Gly Phe Glu Ala His Gly Leu Ser Glu Glu
            20                  25                  30

Glu Ala Arg Val Arg Ala Ile Ala Glu Ile Val Gly Ser Met Val Asp
        35                  40                  45

Leu Ser Arg Arg Gly Glu Thr Val Asp Leu Asn Ala Leu Lys Thr Ala
    50                  55                  60

Ala Cys Arg Lys Tyr Gly Leu Ala Arg Ala Pro Lys Leu Val Glu Met
65                  70                  75                  80

Ile Ala Ala Leu Pro Glu Ser Asp Arg Glu Ala Leu Leu Pro Lys Leu
                85                  90                  95

Lys Ala Lys Pro Val Arg Thr Ala Ser Gly Ile Ala Val Val Ala Val
            100                 105                 110

Met Ser Lys Pro His Arg Cys Pro His Ile Ala Thr Thr Gly Asn Ile
        115                 120                 125

Cys Val Tyr Cys Pro Gly Gly Pro Asp Ser Asp Phe Glu Tyr Ser Thr
    130                 135                 140

Gln Ser Tyr Thr Gly Tyr Glu Pro Thr Ser Met Arg Ala Ile Arg Ala
145                 150                 155                 160

Arg Tyr Asn Pro Tyr Val Gln Ala Arg Gly Arg Ile Asp Gln Leu Lys
                165                 170                 175

Arg Leu Gly His Ser Val Asp Lys Val Glu Tyr Ile Leu Met Gly Gly
            180                 185                 190
```

Thr Phe Met Ser Leu Pro Ala Asp Tyr Arg Asp Tyr Phe Ile Arg Asn
            195                 200                 205

Leu His Asp Ala Leu Ser Gly His Thr Ser Ala Asn Val Glu Glu Ala
210                 215                 220

Val Ala Tyr Ser Glu His Gly Ala Thr Lys Cys Ile Gly Met Thr Ile
225                 230                 235                 240

Glu Thr Arg Pro Asp Tyr Cys Leu Gly Pro His Leu Arg Gln Met Leu
                245                 250                 255

Thr Tyr Gly Cys Thr Arg Leu Glu Ile Gly Val Gln Ser Thr Tyr Glu
                260                 265                 270

Asp Val Ala Arg Asp Thr Asn Arg Gly His Thr Val Ala Ala Val Ala
                275                 280                 285

Asp Cys Phe Cys Leu Ala Lys Asp Ala Gly Phe Lys Val Val Ala His
                290                 295                 300

Met Met Pro Asp Leu Pro Asn Val Gly Val Glu Arg Asp Met Glu Ser
305                 310                 315                 320

Phe Arg Glu Phe Phe Glu Ser Pro Leu Phe Arg Ala Asp Gly Leu Lys
                    325                 330                 335

Ile Tyr Pro Thr Leu Val Ile Arg Gly Thr Gly Leu Tyr Glu Leu Trp
                340                 345                 350

Lys Thr Gly Arg Tyr Arg Asn Tyr Pro Pro Glu Gln Leu Val Asp Ile
                355                 360                 365

Val Ala Arg Ile Leu Ala Met Val Pro Pro Trp Thr Arg Val Tyr Arg
                370                 375                 380

Val Gln Arg Asp Ile Pro Met Pro Leu Val Thr Ser Gly Val Glu Lys
385                 390                 395                 400

Gly Asn Leu Arg Glu Leu Ala Leu Ala Arg Met Glu Asp Leu Gly Leu
                    405                 410                 415

Lys Cys Arg Asp Val Arg Thr Arg Glu Ala Gly Ile Gln Asp Ile His
                420                 425                 430

His Gln Ile Lys Pro Asp Glu Val Glu Leu Val Arg Arg Asp Tyr Thr
            435                 440                 445

Ala Asn Glu Gly Trp Glu Thr Phe Leu Ser Tyr Glu Asp Thr Arg Gln
            450                 455                 460

Asp Ile Leu Val Gly Leu Leu Arg Leu Arg Lys Cys Gly Arg Asn Thr
465                 470                 475                 480

Ser Cys Pro Glu Leu Met Gly Lys Cys Ser Ile Val Arg Glu Leu His
                    485                 490                 495

Val Tyr Gly Thr Ala Val Pro Val His Gly Arg Asp Ala Gly Lys Leu
                500                 505                 510

Gln His Gln Gly Tyr Gly Thr Leu Leu Met Glu Glu Ala Glu Arg Ile
            515                 520                 525

Ala Arg Arg Glu His Arg Ser Thr Lys Ile Ala Val Ile Ser Gly Val
            530                 535                 540

Gly Thr Arg His Tyr Tyr Arg Lys Leu Gly Tyr Glu Leu Glu Gly Pro
545                 550                 555                 560

Tyr Met Val Lys Tyr Leu Asp
                565

<210> SEQ ID NO 33
<211> LENGTH: 564
<212> TYPE: PRT
<213> ORGANISM: Cucumis melo

<400> SEQUENCE: 33

```
Met Ala Thr Ala Met Val Ala Glu Pro Asn Arg Lys Leu Pro Arg Pro
1               5                   10                  15

Gly Arg Gly Gly Phe Glu Gly His Gly Phe Ser Glu Glu Ala Arg
            20                  25                  30

Val Arg Ala Ile Ala Glu Ile Val Asn Ser Met Val Asp Leu Ser Arg
                35                  40                  45

Lys Gly Gln Asn Val Asp Leu Asn Ala Leu Lys Ser Ala Ala Cys Arg
50                  55                  60

Lys Tyr Gly Leu Ala Arg Ala Pro Lys Leu Val Glu Met Ile Ala Ala
65                  70                  75                  80

Leu Pro Glu Ser Asp Arg Glu Ala Leu Leu Pro Lys Leu Arg Ala Lys
                85                  90                  95

Pro Val Arg Thr Ala Ser Gly Ile Ala Val Val Ala Val Met Ser Lys
                100                 105                 110

Pro His Arg Cys Pro His Ile Ala Thr Thr Gly Asn Ile Cys Val Tyr
            115                 120                 125

Cys Pro Gly Gly Pro Asp Ser Asp Phe Glu Tyr Ser Thr Gln Ser Tyr
            130                 135                 140

Thr Gly Tyr Glu Pro Thr Ser Met Arg Ala Ile Arg Ala Arg Tyr Asn
145                 150                 155                 160

Pro Tyr Val Gln Ala Arg Ser Arg Ile Asp Gln Leu Lys Arg Leu Gly
                165                 170                 175

His Ser Val Asp Lys Val Glu Phe Ile Leu Met Gly Gly Thr Phe Met
            180                 185                 190

Ser Leu Pro Ala Asp Tyr Arg Asp Tyr Phe Ile Arg Asn Leu His Asp
            195                 200                 205

Ala Leu Ser Gly His Thr Ser Ala Asn Val Glu Glu Ala Val Ala Tyr
            210                 215                 220

Ser Glu His Gly Ala Val Lys Cys Ile Gly Met Thr Ile Glu Thr Arg
225                 230                 235                 240

Pro Asp Tyr Cys Leu Gly Pro His Leu Arg Gln Met Leu Ser Tyr Gly
                245                 250                 255

Cys Thr Arg Leu Glu Ile Gly Val Gln Ser Thr Tyr Glu Asp Val Ala
            260                 265                 270

Arg Asp Thr Asn Arg Gly His Thr Val Ala Ala Val Ala Asp Cys Phe
            275                 280                 285

Cys Leu Ala Lys Asp Ala Gly Phe Lys Val Val Ala His Met Met Pro
            290                 295                 300

Asp Leu Pro Asn Val Gly Val Glu Arg Asp Leu Glu Ser Phe Arg Glu
305                 310                 315                 320

Phe Phe Glu Asn Pro Ser Phe Arg Ala Asp Gly Leu Lys Ile Tyr Pro
                325                 330                 335

Thr Leu Val Ile Arg Gly Thr Gly Leu Tyr Glu Leu Trp Lys Thr Gly
            340                 345                 350

Arg Tyr Arg Asn Tyr Pro Pro Glu Gln Leu Val Asp Ile Val Ala Arg
            355                 360                 365

Ile Leu Ala Met Val Pro Pro Trp Thr Arg Val Tyr Arg Val Gln Arg
370                 375                 380

Asp Ile Pro Met Pro Leu Val Thr Ser Gly Val Glu Lys Gly Asn Leu
385                 390                 395                 400

Arg Glu Leu Ala Leu Ala Arg Met Asp Asp Leu Gly Leu Lys Cys Arg
                405                 410                 415
```

```
Asp Val Arg Thr Arg Glu Ala Gly Ile Gln Asp Ile His His Lys Ile
            420                 425                 430

Lys Pro Asp Glu Val Glu Leu Val Arg Arg Asp Tyr Met Ala Asn Glu
            435                 440                 445

Gly Trp Glu Thr Phe Leu Ser Tyr Glu Asp Val Cys Gln Asp Ile Leu
450                 455                 460

Val Gly Leu Leu Arg Leu Arg Arg Cys Gly Arg Asn Thr Thr Cys Pro
465                 470                 475                 480

Glu Leu Val Gly Lys Cys Ser Ile Val Arg Glu Leu His Val Tyr Gly
            485                 490                 495

Thr Ala Val Pro Val His Gly Arg Asp Thr Glu Lys Leu Gln His Gln
            500                 505                 510

Gly Tyr Gly Thr Leu Leu Met Glu Glu Ala Glu Arg Ile Ala Arg His
            515                 520                 525

Glu His Arg Ser Lys Lys Ile Ala Val Ile Ser Gly Val Gly Thr Arg
            530                 535                 540

His Tyr Tyr Arg Lys Leu Gly Tyr Glu Leu Glu Gly Pro Tyr Met Val
545                 550                 555                 560

Lys Ser Leu Glu

<210> SEQ ID NO 34
<211> LENGTH: 570
<212> TYPE: PRT
<213> ORGANISM: Zea mays

<400> SEQUENCE: 34

Met Ala Thr Ala Ala Thr Ala Met Val Val Pro Glu Gln Pro Arg Arg
1               5                   10                  15

Arg Lys Pro Ala Pro Gly Arg Gly Gly Val Ala Leu Pro Ala Gly Leu
            20                  25                  30

Ser Glu Glu Glu Ala Arg Val Arg Ala Ile Ala Glu Ile Val Ser Ala
            35                  40                  45

Met Gly Glu Leu Ser Arg Arg Gly Glu Asp Val Asp Leu Asn Ala Leu
        50                  55                  60

Lys Ser Ala Ala Cys Arg Arg Tyr Gly Leu Ala Arg Ala Pro Lys Leu
65                  70                  75                  80

Val Glu Met Ile Ala Ala Val Pro Glu Ala Asp Arg Ala Ala Leu Leu
                85                  90                  95

Pro Arg Leu Arg Ala Lys Pro Val Arg Thr Ala Ser Gly Ile Ala Val
            100                 105                 110

Val Ala Val Met Ser Lys Pro His Arg Cys Pro His Ile Ala Thr Thr
        115                 120                 125

Gly Asn Ile Cys Val Tyr Cys Pro Gly Gly Pro Asp Ser Asp Phe Glu
    130                 135                 140

Tyr Ser Thr Gln Ser Tyr Thr Gly Tyr Glu Pro Thr Ser Met Arg Ala
145                 150                 155                 160

Ile Arg Ala Arg Tyr Asn Pro Tyr Val Gln Ala Arg Ser Arg Ile Asp
                165                 170                 175

Gln Leu Lys Arg Leu Gly His Ser Val Asp Lys Val Glu Phe Ile Leu
            180                 185                 190

Met Gly Gly Thr Phe Met Ser Leu Pro Ala Asp Tyr Arg Asp Tyr Phe
        195                 200                 205

Ile Arg Asn Leu His Asp Ala Leu Ser Gly His Thr Ser Ala Asn Val
    210                 215                 220
```

```
Glu Ala Ile Cys Tyr Ser Glu His Ser Ala Val Lys Cys Ile Gly
225                 230                 235                 240

Met Thr Ile Glu Thr Arg Pro Asp Tyr Cys Leu Gly Pro His Leu Arg
            245                 250                 255

Gln Met Leu Ser Tyr Gly Cys Thr Arg Leu Glu Ile Gly Val Gln Ser
        260                 265                 270

Thr Tyr Glu Asp Val Ala Arg Asp Thr Asn Arg Gly His Thr Val Ala
    275                 280                 285

Ala Val Ala Asp Cys Phe Cys Leu Ala Lys Asp Ala Gly Phe Lys Val
290                 295                 300

Val Ala His Met Met Pro Asp Leu Pro Asn Val Gly Val Glu Arg Asp
305                 310                 315                 320

Leu Glu Ser Phe Arg Glu Phe Glu Ser Pro Ala Phe Arg Ala Asp
                325                 330                 335

Gly Leu Lys Ile Tyr Pro Thr Leu Val Ile Arg Gly Thr Gly Leu Tyr
            340                 345                 350

Glu Leu Trp Lys Thr Gly Arg Tyr Arg Asn Tyr Pro Pro Glu Leu Leu
        355                 360                 365

Val Asp Ile Val Ala Arg Ile Leu Ser Met Val Pro Pro Trp Thr Arg
    370                 375                 380

Val Tyr Arg Val Gln Arg Asp Ile Pro Met Pro Leu Val Thr Ser Gly
385                 390                 395                 400

Val Glu Lys Gly Asn Leu Arg Glu Leu Ala Leu Ala Arg Met Asp Asp
                405                 410                 415

Leu Gly Leu Lys Cys Arg Asp Val Thr Arg Glu Ala Gly Ile Gln
            420                 425                 430

Asp Ile His His Lys Ile Arg Pro Asp Glu Val Glu Leu Val Arg Arg
        435                 440                 445

Asp Tyr Ala Ala Asn Glu Gly Trp Glu Thr Phe Leu Ser Tyr Glu Asp
    450                 455                 460

Thr Arg Gln Asp Ile Leu Ile Gly Leu Leu Arg Leu Arg Lys Cys Gly
465                 470                 475                 480

Arg Asn Val Thr Cys Pro Glu Leu Val Gly Arg Cys Ser Ile Val Arg
                485                 490                 495

Glu Leu His Val Tyr Gly Thr Ala Val Pro Val His Gly Arg Asp Val
            500                 505                 510

Asp Lys Leu Gln His Gln Gly Tyr Gly Thr Leu Leu Met Glu Glu Ala
        515                 520                 525

Glu Arg Ile Ala Gln Lys Glu His Arg Ser Glu Lys Leu Ala Val Ile
    530                 535                 540

Ser Gly Val Gly Thr Arg His Tyr Tyr Arg Lys Leu Gly Tyr Glu Leu
545                 550                 555                 560

Glu Gly Pro Tyr Met Val Lys Cys Leu Ala
                565                 570

<210> SEQ ID NO 35
<211> LENGTH: 573
<212> TYPE: PRT
<213> ORGANISM: Oryza sativa

<400> SEQUENCE: 35

Met Ala Thr Ala Val Ala Ala Gly Gly Gly Gly Gly Glu Gln
1               5                   10                  15

Pro Arg Arg Arg Lys Pro Ala Pro Gly Arg Gly Gly Val Val Leu Pro
```

```
             20                  25                  30
Ala Gly Leu Ser Glu Glu Ala Arg Val Arg Ala Ile Ala Glu Ile
             35                  40                  45

Val Ser Ala Met Gly Glu Leu Ser Arg Arg Gly Glu Asp Val Asp Leu
    50                  55                  60

Asn Ala Leu Lys Ser Ala Ala Cys Arg Arg Tyr Gly Leu Ala Arg Ala
65                  70                  75                  80

Pro Lys Leu Val Glu Met Ile Ala Ala Val Pro Glu Ala Asp Arg Ala
                85                  90                  95

Ala Leu Leu Pro Arg Leu Arg Ala Lys Pro Val Arg Thr Ala Ser Gly
                100                 105                 110

Ile Ala Val Ala Val Met Ser Lys Pro His Arg Cys Pro His Ile
        115                 120                 125

Ala Thr Thr Gly Asn Ile Cys Val Tyr Cys Pro Gly Gly Pro Asp Ser
        130                 135                 140

Asp Phe Glu Tyr Ser Thr Gln Ser Tyr Thr Gly Tyr Glu Pro Thr Ser
145                 150                 155                 160

Met Arg Ala Ile Arg Ala Arg Tyr Asn Pro Tyr Val Gln Ala Arg Ser
                165                 170                 175

Arg Ile Asp Gln Leu Lys Arg Leu Gly His Ser Val Asp Lys Val Glu
                180                 185                 190

Phe Ile Leu Met Gly Gly Thr Phe Met Ser Leu Pro Ala Asp Tyr Arg
                195                 200                 205

Asp Tyr Phe Ile Arg Asn Leu His Asp Ala Leu Ser Gly His Thr Ser
                210                 215                 220

Ala Asn Val Glu Glu Ala Val Cys Tyr Ser Glu His Gly Ala Val Lys
225                 230                 235                 240

Cys Ile Gly Met Thr Ile Glu Thr Arg Pro Asp Tyr Cys Leu Gly Pro
                245                 250                 255

His Leu Arg Gln Met Leu Ser Tyr Gly Cys Thr Arg Leu Glu Ile Gly
                260                 265                 270

Val Gln Ser Thr Tyr Glu Asp Val Ala Arg Asp Thr Asn Arg Gly His
                275                 280                 285

Thr Val Ala Ala Val Ala Asp Cys Phe Cys Leu Ala Lys Asp Ala Gly
        290                 295                 300

Phe Lys Val Val Ala His Met Met Pro Asp Leu Pro Asn Val Gly Val
305                 310                 315                 320

Glu Arg Asp Leu Glu Ser Phe Arg Glu Phe Phe Glu Asn Pro Ala Phe
                325                 330                 335

Arg Ala Asp Gly Leu Lys Ile Tyr Pro Thr Leu Val Ile Arg Gly Thr
                340                 345                 350

Gly Leu Tyr Glu Leu Trp Lys Thr Gly Arg Tyr Arg Asn Tyr Pro Pro
                355                 360                 365

Glu Leu Leu Val Asp Ile Val Ala Arg Ile Leu Ser Met Val Pro Pro
                370                 375                 380

Trp Thr Arg Val Tyr Arg Val Gln Arg Asp Ile Pro Met Pro Leu Val
385                 390                 395                 400

Thr Ser Gly Val Glu Lys Gly Asn Leu Arg Glu Leu Ala Leu Ala Arg
                405                 410                 415

Met Glu Asp Leu Gly Leu Lys Cys Arg Asp Val Arg Thr Arg Glu Ala
                420                 425                 430

Gly Ile Gln Asp Ile His His Lys Ile Arg Pro Asp Glu Val Glu Leu
                435                 440                 445
```

```
Val Arg Arg Asp Tyr Ala Ala Asn Glu Gly Trp Glu Thr Phe Leu Ser
    450                 455                 460

Tyr Glu Asp Thr Gln Gln Asp Ile Leu Ile Gly Leu Leu Arg Leu Arg
465                 470                 475                 480

Lys Cys Gly Arg Asn Val Thr Cys Pro Glu Leu Val Gly Arg Cys Ser
                485                 490                 495

Ile Val Arg Glu Leu His Val Tyr Gly Thr Ala Val Pro Val His Gly
                500                 505                 510

Arg Asp Ala Asp Lys Leu Gln His Gln Gly Tyr Gly Thr Leu Leu Met
                515                 520                 525

Glu Glu Ala Glu Arg Ile Ala Arg Lys Glu His Arg Ser Lys Lys Ile
530                 535                 540

Ala Val Ile Ser Gly Val Gly Thr Arg His Tyr Tyr Arg Lys Leu Gly
545                 550                 555                 560

Tyr Glu Leu Glu Gly Pro Tyr Met Val Lys Cys Leu Val
                565                 570
```

<210> SEQ ID NO 36
<211> LENGTH: 565
<212> TYPE: PRT
<213> ORGANISM: Eucalyptis grandis

<400> SEQUENCE: 36

```
Met Ala Ala Ala Val Ala Val Ala Glu Thr Arg Arg Gln Pro Arg
1               5                   10                  15

Pro Gly Gly Gly Gly Phe Gln Ala His Gly Leu Thr Glu Glu Ala
                20                  25                  30

Arg Val Arg Ala Ile Gly Glu Ile Val Ser Ala Met Val Asp Leu Ser
                35                  40                  45

Arg Lys Gly Glu Thr Val Asp Leu Asn Ala Leu Lys Ser Ala Ala Cys
50                  55                  60

Arg Lys Tyr Gly Leu Ala Arg Ala Pro Lys Leu Val Glu Met Ile Ala
65                  70                  75                  80

Ala Leu Pro Glu Ser Asp Arg Asp Ala Leu Leu Pro Lys Leu Lys Ala
                85                  90                  95

Lys Pro Val Arg Thr Ala Ser Gly Ile Ala Val Val Ala Val Met Ser
                100                 105                 110

Lys Pro His Arg Cys Pro His Ile Ala Thr Thr Gly Asn Ile Cys Val
                115                 120                 125

Tyr Cys Pro Gly Gly Pro Asp Ser Asp Phe Glu Tyr Ser Thr Gln Ser
130                 135                 140

Tyr Thr Gly Tyr Glu Pro Thr Ser Met Arg Ala Ile Arg Ala Arg Tyr
145                 150                 155                 160

Asn Pro Tyr Val Gln Ala Arg Gly Arg Ile Asp Gln Leu Lys Arg Leu
                165                 170                 175

Gly His Ser Val Asp Lys Val Glu Phe Ile Leu Met Gly Gly Thr Phe
                180                 185                 190

Met Ser Leu Pro Ala Asp Tyr Arg Asp Tyr Phe Ile Arg Asn Leu His
                195                 200                 205

Asp Ala Leu Ser Gly His Thr Ser Ala Asn Val Glu Glu Ala Val Ala
                210                 215                 220

Tyr Ser Glu His Ser Ala Val Lys Cys Ile Gly Met Thr Ile Glu Thr
225                 230                 235                 240

Arg Pro Asp Tyr Cys Leu Gly Pro His Leu Arg Gln Met Leu Ser Tyr
```

```
              245                 250                 255
Gly Cys Thr Arg Leu Glu Ile Gly Val Gln Ser Thr Tyr Glu Asp Val
            260                 265                 270
Ala Arg Asp Thr Asn Arg Gly His Thr Val Ala Ala Val Ala Asp Cys
            275                 280                 285
Phe Cys Leu Ala Lys Asp Ala Gly Phe Lys Val Val Ala His Met Met
            290                 295                 300
Pro Asp Leu Pro Asn Val Gly Val Glu Arg Asp Leu Glu Ser Phe Arg
305                 310                 315                 320
Glu Phe Phe Glu Ser Pro Leu Phe Arg Ala Asp Gly Leu Lys Ile Tyr
                325                 330                 335
Pro Thr Leu Val Ile Arg Gly Thr Gly Leu Tyr Glu Leu Trp Lys Thr
                340                 345                 350
Gly Arg Tyr Arg Asn Tyr Pro Pro Glu Gln Leu Val Asp Ile Val Ala
                355                 360                 365
Arg Ile Leu Ala Met Val Pro Pro Trp Thr Arg Val Tyr Arg Val Gln
            370                 375                 380
Arg Asp Ile Pro Met Pro Leu Val Thr Ser Gly Val Glu Lys Gly Asn
385                 390                 395                 400
Leu Arg Glu Leu Ala Leu Ala Arg Met Asp Asp Leu Gly Leu Lys Cys
                405                 410                 415
Arg Asp Val Arg Thr Arg Glu Ala Gly Ile Gln Asp Ile His His Asn
            420                 425                 430
Ile Arg Pro Glu Glu Val Glu Leu Val Arg Arg Asp Tyr Ser Ala Asn
        435                 440                 445
Glu Gly Trp Glu Thr Phe Leu Ser Tyr Glu Asp Thr His Gln Asp Ile
    450                 455                 460
Leu Val Gly Leu Leu Arg Leu Arg Lys Cys Gly Arg Asn Thr Thr Cys
465                 470                 475                 480
Pro Glu Leu Ile Gly Lys Cys Ser Ile Val Arg Glu Leu His Val Tyr
                485                 490                 495
Gly Thr Ala Val Pro Val His Gly Arg Asp Ala Glu Lys Leu Gln His
            500                 505                 510
Gln Gly Tyr Gly Thr Leu Leu Met Glu Glu Ala Glu Arg Ile Ala Arg
        515                 520                 525
Arg Glu His Arg Ser Thr Lys Ile Ala Val Ile Ser Gly Val Gly Thr
    530                 535                 540
Arg His Tyr Tyr Arg Lys Leu Gly Tyr Glu Leu Glu Gly Pro Tyr Met
545                 550                 555                 560
Val Lys Tyr Leu Glu
                565

<210> SEQ ID NO 37
<211> LENGTH: 355
<212> TYPE: PRT
<213> ORGANISM: Arabidopsis thaliana

<400> SEQUENCE: 37

Met Ala Ala Pro Asn Val Arg Ser Ser Ser Ser Phe Ser Arg Asn Ile
1               5                   10                  15
Ser Val Val Ser Ser Pro Gln Ile Pro Gly Leu Lys Ser Gly Pro Asn
                20                  25                  30
Gly Thr Ala Phe Ile Ser Ser Gly Ile Arg Asp Leu Asp Arg Ile Leu
            35                  40                  45
```

Gly Gly Gly Tyr Pro Leu Gly Ser Leu Val Met Val Met Glu Asp Pro
50                  55                  60

Glu Ala Pro His His Met Asp Leu Leu Arg Thr Tyr Met Ser Gln Gly
65                  70                  75                  80

Leu Val Asn Asn Gln Pro Leu Leu Tyr Ala Ser Pro Ser Lys Asp Pro
                85                  90                  95

Lys Gly Phe Leu Gly Thr Leu Pro His Pro Ala Ser Ser Lys Glu Asp
                100                 105                 110

Lys Pro Thr Ala Pro Asp Pro Asp Gln Gly Glu Ser Leu Arg Ile Ala
                115                 120                 125

Trp Gln Tyr Arg Lys Tyr Leu Glu Asn Gln Lys Asn Ala Ile Asp Asp
130                 135                 140

Tyr Ser Asn Asp Phe Asp Met Arg Lys Pro Leu Glu Arg Gln Phe Leu
145                 150                 155                 160

Ser Gly Arg Pro Ile Asp Cys Val Ser Leu Leu Asp Ser Ser Asp Leu
                165                 170                 175

Ser Ile Ala Gln Asp His Cys Ala Thr Phe Leu Ser Lys Phe Pro Arg
                180                 185                 190

Asn Ser Ser Asn Ile Ala Ser Ile Gly Arg Ile Ala Ile Gln Ser Phe
                195                 200                 205

Cys Ser Pro Leu Cys Glu Tyr Ser Glu Lys Glu Ser Asp Met Leu Ser
210                 215                 220

Phe Ile Arg Leu Leu Lys Ser Met Leu Met Val Ser Asn Ala Val Ala
225                 230                 235                 240

Ile Val Thr Phe Pro Pro Ser Leu Leu Ser Pro Ser Ser Ser Lys Arg
                245                 250                 255

Leu Gln His Met Ala Asp Thr Leu Leu Ser Ile Lys Ala Ile Pro Asp
                260                 265                 270

Gly Asp Lys Glu Leu Glu Lys Leu Leu Thr Gly Tyr Lys Asp Ile Asn
                275                 280                 285

Gly Phe Leu Asn Ile His Lys Val Ala Arg Ile Asn Thr Gln Val Pro
                290                 295                 300

Val Ile Leu Glu Ala Lys Thr Phe Ser Met Ser Leu Lys Lys Arg Arg
305                 310                 315                 320

Phe Leu Ala Leu Glu Cys Leu Asn Gln Ala Pro Val Asp Gly Ser Ser
                325                 330                 335

Gly Thr Ser Tyr Gly Thr Ser Ser Cys Ser Ser Lys Ser Gly Ala
                340                 345                 350

Leu Asp Phe
        355

<210> SEQ ID NO 38
<211> LENGTH: 375
<212> TYPE: PRT
<213> ORGANISM: Brassica napus

<400> SEQUENCE: 38

Met Ala Ala Pro Asn Val Arg Thr Ser Ser Phe Ser Arg Asn Ile Ser
1               5                   10                  15

Val Val Ser Ser Ser Pro Gln Ile Pro Gly Leu Lys Cys Gly Pro Asn
                20                  25                  30

Gly Thr Thr Phe Ile Ser Thr Gly Ile Arg Asp Leu Asp Arg Ile Leu
                35                  40                  45

Gly Gly Gly Tyr Pro Leu Gly Ser Leu Val Met Val Met Glu Asp Pro
50                  55                  60

Glu Ala Pro His His Met Asp Leu Leu Arg Thr Phe Met Ser Gln Gly
65                  70                  75                  80

Leu Val Asn Asn Gln Pro Leu Leu Tyr Ala Ser Pro Ser Lys Asp Pro
            85                  90                  95

Arg Gly Phe Leu Gly Thr Leu Pro Asn Pro Gly Ser Ser Lys Glu Asp
            100                 105                 110

Lys Pro Thr Ala Pro Asp Leu Asp Gln Gly Glu Ser Leu Arg Ile Ala
            115                 120                 125

Trp Gln Tyr Arg Lys Tyr Met Glu Asn Gln Lys Ser Ser Ile Asp Asp
130                 135                 140

Tyr Ser Asn Asp Phe Asp Met Arg Lys Pro Leu Glu Arg Gln Phe Leu
145                 150                 155                 160

Ala Gly Arg Pro Ile Asp Cys Val Ser Leu Leu Asp Ser Ser Asp Leu
            165                 170                 175

Ser Val Ala Glu Asp His Cys Ala Thr Phe Leu Ser Lys Phe Pro Arg
            180                 185                 190

Leu Cys Ile Ile Ser Phe Leu Phe Asp Gly His Leu Leu Phe Lys
            195                 200                 205

Leu Val Asn Ser Ser Asn Ile Ala Ser Ile Gly Arg Ile Ala Ile Gln
210                 215                 220

Ser Phe Cys Ser Pro Leu Cys Glu Tyr Ser Asp Lys Glu Ser Glu Met
225                 230                 235                 240

Leu Ser Phe Ile Arg Leu Leu Lys Ser Met Leu Met Val Ser Asn Ala
            245                 250                 255

Val Ala Ile Val Thr Phe Pro Pro Ser Met Leu Ser Pro Ser Ser Ser
            260                 265                 270

Thr Arg Leu Gln His Met Ala Asp Thr Leu Leu Ser Ile Lys Ala Ile
            275                 280                 285

Pro Asp Gly Asp Lys Glu Leu Glu Lys Leu Leu Thr Gly Tyr Lys Asp
290                 295                 300

Ile Asn Gly Phe Leu Asn Val His Lys Val Ala Arg Ile Asn Thr Gln
305                 310                 315                 320

Val Pro Val Ile Leu Glu Ala Lys Thr Phe Ser Met Ser Leu Lys Lys
            325                 330                 335

Arg Arg Phe Leu Ala Leu Glu Cys Leu Asn Gln Ala Pro Val Asp Gly
            340                 345                 350

Ser Ser Gly Thr Ser Tyr Gly Thr Ser Gly Ser Cys Ser Gly Ser Ser
            355                 360                 365

Lys Ser Gly Ala Leu Asp Phe
            370                 375

<210> SEQ ID NO 39
<211> LENGTH: 361
<212> TYPE: PRT
<213> ORGANISM: Gossypium arboreum

<400> SEQUENCE: 39

Met Ala Ala Ala Lys Thr Arg Thr Ser Thr Phe Ser Arg Asn Leu Ser
1               5                   10                  15

Thr Ala Ala Pro Ser His Gly Pro Gly Leu Lys Cys Gly Pro Asn Gly
            20                  25                  30

Thr Val Phe Leu Ser Ser Gly Ile Pro Asp Leu Asp Lys Ile Leu Gly
            35                  40                  45

Gly Gly Phe Pro Leu Gly Ser Leu Val Met Val Met Glu Asp Ala Glu

```
            50                  55                  60
Ala Pro His His Met Leu Leu Arg Asn Phe Met Ala Gln Gly Leu
 65                  70                  75                  80

Val Leu Gly Gln Pro Leu Leu Tyr Ser Ser Pro Ala Arg Asp Pro Arg
                 85                  90                  95

Gly Phe Leu Gly Thr Leu Pro Ser Pro Ala Ala Ser Lys Asp Asp Lys
                100                 105                 110

Ser Gln Glu Arg Asp Pro Asp Gln Glu Lys Gly Leu Arg Ile Ala Trp
                115                 120                 125

Gln Tyr Lys Lys Tyr Phe Gly Glu Ser Gln Leu Asp Gly Gln Arg Asp
            130                 135                 140

Ser Lys His Glu Tyr Ser Asn Glu Phe Asp Leu Arg Lys Pro Leu Glu
145                 150                 155                 160

Arg His Phe Ile Asn Gly Pro Arg Ile Asp Cys Val Ser Ile Gln Asp
                165                 170                 175

Cys Pro Asp Leu Ser Thr Leu Arg Asp Arg Cys Ala Thr Phe Leu Ser
                180                 185                 190

Gln Phe Pro Arg Asn Asp Gly Ser Ile Ser Cys Ala Gly Arg Ile Ala
                195                 200                 205

Ile Gln Ser Phe Cys Ala Pro Gln Cys Ala Tyr Ser Asn Met Glu Trp
    210                 215                 220

Asp Met Leu Ser Phe Ile Arg Tyr Leu Lys Ser Met Val Arg Ser Ser
225                 230                 235                 240

Asn Ser Val Ala Ile Ile Thr Phe Pro Pro Ser Leu Leu Ser Pro Ser
                245                 250                 255

Phe Cys Lys Arg Trp Gln His Met Ala Asp Thr Leu Leu Ser Val Lys
                260                 265                 270

Ala Ile Gln Asp Glu Asp Lys Glu Leu Ala Gln Leu Leu Thr Gly Tyr
                275                 280                 285

Gln Asp Met Val Gly Phe Leu Asn Val His Lys Val Ala Arg Ile Asn
            290                 295                 300

Thr Gln Val Pro Val Ile Leu Glu Ala Thr Thr Phe Ser Ile Lys Leu
305                 310                 315                 320

Gln Lys Arg Arg Tyr Leu Val Leu Glu Cys Leu Asn Gln Ala Pro Val
                325                 330                 335

Asp Gly Ser Ser Gly Thr Ser Tyr Gly Thr Ser Gly Trp Ser Ser
                340                 345                 350

Ser Ser Lys Thr Gly Asn Leu Asp Phe
            355                 360

<210> SEQ ID NO 40
<211> LENGTH: 361
<212> TYPE: PRT
<213> ORGANISM: Glycine max

<400> SEQUENCE: 40

Met Ala Ala Thr Arg Ala Arg Val Ser Ser Phe Ser Arg Asn Val Ser
 1               5                  10                  15

Thr Val Thr Ser Gln Asn His Gly Leu Lys His Gly Pro Asn Gly Thr
                20                  25                  30

Met Phe Ile Ser Ser Gly Ile Pro Asp Leu Asp Lys Ile Leu Gly Gly
            35                  40                  45

Gly Phe Ser Leu Gly Ser Leu Val Met Val Met Glu Asp Pro Glu Ala
 50                  55                  60
```

```
Pro His His Met Leu Leu Arg Asn Phe Met Ser Gln Gly Leu Val
 65                  70                  75                  80

Gln Lys Gln Pro Leu Leu Tyr Ala Ser Ala Ser Arg Asp Pro Lys Ser
                 85                  90                  95

Phe Leu Gly Thr Leu Pro Ser Pro Ala Ser Pro Lys Gly Asp Asn Lys
                100                 105                 110

Ser Ser Asp Leu Ser His Glu Lys Asp Leu Arg Ile Ala Trp Gln Tyr
                115                 120                 125

Lys Lys Tyr Phe Gly Glu Pro Gln Leu Asn Leu Thr Asn Asn Gly
130                 135                 140

Gly Gln His Asp Tyr Cys Asn Asp Phe Asp Leu Arg Lys Pro Leu Asp
145                 150                 155                 160

Arg His Phe Phe Ser Gly Asn Asn Val Asp Cys Val Ser Ile Lys Asp
                165                 170                 175

Ser Pro Asn Leu Thr Ala Leu Gln Asp Cys Cys Ala Gly Phe Leu Ala
                180                 185                 190

Lys Phe Ser Arg Asn Glu Gly Ser Ile Ser Ser Ala Gly Arg Ile Ala
                195                 200                 205

Ile Gln Ser Phe Cys Ser Pro Gln Cys Lys Tyr Ser Asn Glu Glu Trp
210                 215                 220

His Met Leu Ser Phe Ile Arg Ser Leu Lys Gly Met Ala Arg Ser Ser
225                 230                 235                 240

Asn Ala Val Ile Val Val Thr Phe Pro Pro Ser Leu Leu Pro Pro Ser
                245                 250                 255

Cys Ser Lys Arg Leu Gln His Met Ala Asp Thr Leu Leu Ser Val Lys
                260                 265                 270

Ala Ile Pro Asp Glu Asp Lys Glu Leu Ala Lys Leu Leu Thr Gly Tyr
                275                 280                 285

Gln Asp Met Ile Gly Leu Leu Asn Val His Lys Val Ala Arg Leu Asn
290                 295                 300

Thr Gln Val Pro Val Ile Leu Glu Ala Thr Thr Phe Ser Ile Lys Leu
305                 310                 315                 320

Gln Lys Arg Arg Phe Leu Val Leu Glu Cys Leu Asn Gln Ala Pro Val
                325                 330                 335

Asp Gly Ser Ser Gly Ser Ser Tyr Gly Thr Ser Gly Gly Cys Ser Gly
                340                 345                 350

Ser Thr Lys Ala Gly Pro Leu Asp Phe
                355                 360

<210> SEQ ID NO 41
<211> LENGTH: 449
<212> TYPE: PRT
<213> ORGANISM: Citrus sinensis

<400> SEQUENCE: 41

Met Lys Ala Ala Gln Thr Pro His Lys Lys Glu Val Pro Cys Val Phe
  1               5                  10                  15

Gly Arg Pro Pro Gln Leu Pro Ile Thr Lys Ile Ile Arg Leu Ser Ala
                 20                  25                  30

Ala Leu Leu Ala Arg His Arg Arg Cys Ser Thr Pro Thr Ala Ala Leu
                 35                  40                  45

Ser Leu Pro Pro Arg Val Cys Ser Leu Arg Pro Glu Ser Leu Ser Cys
 50                  55                  60

Arg Leu Ser Thr Ile Tyr Ser Trp His Phe Thr Gly Lys Thr Lys Leu
 65                  70                  75                  80
```

```
Cys Ser Val Asp Ala Ala Met Ala Thr Thr Lys Pro Arg Leu Ser Ser
                 85                  90                  95

Phe Ser Arg Asn Leu Ser Ala Val Ser Ser Gln Thr Pro Gly Val
            100                 105                 110

Lys Cys Gly Pro Asn Gly Thr Met Phe Val Ser Ser Gly Ile Ala Asp
            115                 120                 125

Leu Asp Lys Ile Leu Gly Gly Gly Phe Pro Leu Gly Ser Leu Val Met
130                 135                 140

Val Met Glu Asp Ala Glu Ala Pro His His Met Leu Leu Leu Arg Asn
145                 150                 155                 160

Phe Met Ser Gln Gly Leu Val His Gly Gln Pro Leu Leu Tyr Ala Ser
                165                 170                 175

Pro Ser Lys Asp Pro Arg Gly Phe Leu Gly Thr Leu Pro Ser Pro Ala
            180                 185                 190

Ser Leu Lys His Asp Lys Ser Arg Asp Arg Glu Ser Glu Gln Glu Lys
            195                 200                 205

Gly Leu Arg Ile Ala Trp Gln Tyr Lys Lys Tyr Met Gly Glu Asn Gln
210                 215                 220

Pro Asn Phe Asp Ser His Arg Asp Asn Lys Gln Asp Tyr Cys Asn Glu
225                 230                 235                 240

Phe Asp Phe Arg Lys Pro Leu Glu Arg His Tyr Phe Thr Arg Gln Arg
                245                 250                 255

Val Asn Cys Val Gly Ile Gln His Ser Lys Asn Leu Ala Ala Leu Gln
            260                 265                 270

Glu His Cys Ala Ser Phe Leu Ala Gln His Gln Arg Asn Asp Gly Ser
            275                 280                 285

Ser Ala Leu Ala Gly Arg Ile Ala Ile Gln Ser Leu Cys Ala Pro Gln
290                 295                 300

Cys Glu His Ser Asn Met Asp Trp Glu Met Leu Ser Phe Ile Lys Ser
305                 310                 315                 320

Leu Lys Gly Met Val Arg Ser Ser Asn Ala Val Val Ile Thr Phe
                325                 330                 335

Pro Pro Ser Leu Leu Ser Leu Ser Ser Thr Lys Arg Trp Gln His Met
            340                 345                 350

Ala Asp Thr Leu Leu Ser Val Ala Ala Ile Pro Asp Glu Asp Lys Glu
            355                 360                 365

Leu Ala Lys Leu Leu Ser Gly Tyr Gln Asp Met Val Gly Leu Leu Asn
370                 375                 380

Val His Lys Val Ala Arg Leu Asn Thr Gln Val Pro Leu Ile Leu Glu
385                 390                 395                 400

Ala Thr Thr Phe Ser Ile Lys Leu Gln Lys Arg Arg Phe Leu Val Leu
                405                 410                 415

Glu Cys Leu Asn Gln Ala Pro Val Asp Gly Ser Ser Gly Ser Ser Tyr
            420                 425                 430

Gly Thr Ser Gly Ser Cys Ser Gly Ser Ser Lys Ala Gly Thr Leu Asp
            435                 440                 445

Phe

<210> SEQ ID NO 42
<211> LENGTH: 360
<212> TYPE: PRT
<213> ORGANISM: Solanum lycopersicum

<400> SEQUENCE: 42
```

Met Ala Ser Ser Arg Pro Arg Gly Gly Ser Phe Ser Arg Asn Ile Ser
1               5                   10                  15

Ser Ala Ala Thr Ala Gln Ile Pro Gly Val Lys Leu Gly Pro Asn Gly
            20                  25                  30

Thr Ser Phe Leu Ser Ser Gly Ile Pro Asp Leu Asp Gln Ile Leu Gly
        35                  40                  45

Gly Gly Phe Thr Leu Gly Ser Leu Val Met Val Met Glu Asp Pro Glu
50                  55                  60

Ala Pro His His Met Leu Leu Arg Asn Phe Met Ser Gln Gly Leu
65              70                  75                  80

Ile His Lys Gln Pro Leu Leu Tyr Ala Ser Pro Glu Arg Asp Pro Arg
                85                  90                  95

Gly Phe Leu Gly Thr Leu Pro Ser Pro Met Ala Ser Lys Glu Glu Lys
                100                 105                 110

Ser Asn Glu Arg Pro Ser Glu Gln Asp Ala Asn Leu Arg Ile Ala Trp
            115                 120                 125

Gln Tyr Lys Lys Tyr Phe Gly Glu Gln Thr Glu Val Gln Arg Gly Gly
130                 135                 140

Lys Ala Glu Tyr Cys Asn Asp Phe Asp Leu Arg Lys Pro Leu Glu Arg
145                 150                 155                 160

His Phe Tyr Ser Gly Gln Arg Val Asp Cys Ile Ser Leu Arg Asp Ser
                165                 170                 175

Pro Asn Leu Val Pro Leu Leu Glu Arg Cys Ser Thr Phe Ser Ala Gln
            180                 185                 190

Ile Ser Lys Ser Asp Gly Asn Ile Thr Cys Ala Gly Arg Ile Ala Ile
            195                 200                 205

Gln Ser Leu Cys Ser Pro Gln Cys Asp Phe Ser Asp Lys Asp Trp Glu
210                 215                 220

Met Leu Ser Phe Ile Arg Ser Leu Lys Gly Met Val Arg Ser Ser Gly
225                 230                 235                 240

Ala Val Ala Val Ile Ser Phe Pro Pro Ser Leu Val Ser Pro Ala Phe
                245                 250                 255

Leu Lys Arg Trp Gln His Leu Ala Asp Thr Leu Ile Ser Val Lys Ala
            260                 265                 270

Ile Pro Asp Glu Asp Lys Glu Leu Ala Lys Leu Leu Thr Gly Tyr Gln
            275                 280                 285

Asp Met Leu Gly Leu Leu Ser Val His Lys Val Ala Arg Ile Asn Thr
290                 295                 300

Gln Val Pro Ala Ile Leu Glu Ala Thr Thr Phe Ser Met Lys Leu Arg
305                 310                 315                 320

Lys Arg Arg Ala Leu Val Leu Glu Cys Leu Asn Gln Ala Pro Val Asp
                325                 330                 335

Gly Ser Ser Gly Ser Ser Tyr Gly Thr Ser Gly Ala Cys Ser Gly Ser
            340                 345                 350

Ser Lys Thr Gly Asn Leu Asp Phe
            355                 360

<210> SEQ ID NO 43
<211> LENGTH: 349
<212> TYPE: PRT
<213> ORGANISM: Medicago truncatula

<400> SEQUENCE: 43

Met Ala Ala Thr Arg Thr Arg Val Ser Ser Phe Ser Arg Asn Val Ser

```
            1               5                  10                 15
        Thr Val Thr Ser Gln Asn Ser Gly Leu Lys His Gly Pro Asn Gly Thr
                        20                 25                 30

Thr Phe Leu Ser Ser Gly Ile Pro Asp Leu Asp Lys Ile Leu Gly Gly
                        35                 40                 45

Gly Phe Ser Leu Gly Ser Leu Val Met Ile Met Glu Asp Ala Glu Ala
                        50                 55                 60

Pro His His Met Leu Leu Leu Arg Asn Leu Met Ser Gln Gly Leu Val
         65                 70                 75                 80

His Lys Gln Pro Leu Leu Tyr Ala Ser Ala Arg Asp Pro Lys Gly
                        85                 90                 95

Phe Leu Gly Thr Leu Pro Ala Pro Ala Pro Ala Lys Glu Asp Lys Ser
                        100                105                110

Gln Asp Leu Thr Asn Glu Lys Asp Leu Arg Ile Ala Trp Gln Tyr Lys
                        115                120                125

Lys Tyr Phe Gly Ala Gln His Asp Tyr Cys Asn Glu Phe Asp Leu Arg
                        130                135                140

Lys Pro Leu Asp Arg His Phe Tyr Ser Gly Met Asn Val Asp Cys Val
        145                150                155                160

Ser Ile Gln Asp Ser Pro Asn Leu Ala Ser Leu Gln Asp Gln Cys Ala
                        165                170                175

Lys Phe Leu Ser Gln Phe Ser Arg Ser Glu Ala Asn Ile Ser Ser Ala
                        180                185                190

Gly Arg Ile Ala Ile Gln Ser Phe Cys Ser Pro Gln Cys Lys Tyr Ala
                        195                200                205

Asn Met Glu Trp His Met Leu Ser Phe Ile Arg Ser Leu Lys Gly Met
        210                215                220

Ala Arg Ser Ser Asn Ala Val Val Val Thr Phe Pro Pro Ser Leu
        225                230                235                240

Val Ser Pro Ser Cys Ser Lys Arg Leu Gln His Met Ala Asp Thr Leu
                        245                250                255

Leu Ser Val Arg Ala Ile Pro Asp Glu Asp Lys Glu Met Ala Lys Leu
                        260                265                270

Leu Thr Gly Tyr Gln Asp Met Val Gly Leu Leu Asn Ile His Lys Val
                        275                280                285

Ala Arg Leu Asn Thr Gln Val Pro Val Ile Leu Glu Ala Thr Thr Phe
                        290                295                300

Ser Ile Lys Leu Gln Lys Arg Arg Tyr Leu Val Leu Glu Cys Leu Asn
        305                310                315                320

Gln Ala Pro Val Asp Gly Ser Ser Gly Ser Ser Tyr Asn Thr Ser Gly
                        325                330                335

Ser Cys Ser Gly Ser Thr Lys Ala Gly Ser Leu Asp Phe
                        340                345
```

<210> SEQ ID NO 44
<211> LENGTH: 362
<212> TYPE: PRT
<213> ORGANISM: Fragaria vesca

<400> SEQUENCE: 44

```
        Met Ala Ala Thr Lys Thr Arg Thr Ser Ser Phe Ser Arg Asn Phe Ser
        1               5                  10                 15

Gly Ala Ser Ser Pro Gln Ile Pro Gly Leu Lys His Gly Pro Asn Gly
                        20                 25                 30
```

```
Thr Met Phe Val Ser Ser Gly Ile Pro Asp Leu Asp Lys Ile Leu Gly
         35                  40                  45

Gly Gly Phe Ala Leu Gly Ser Leu Val Met Val Met Glu Asp Ala Glu
 50                  55                  60

Ala Pro His His Met Leu Leu Arg Asn Phe Met Ser Gln Gly Leu
 65                  70                  75                  80

Val His Asn Gln His Leu Leu Tyr Ala Ser Pro Ala Lys Asp Pro Arg
                 85                  90                  95

Gln Phe Leu Gly Thr Leu Pro Ser Pro Ala Val Pro Lys Asp Glu Lys
                100                 105                 110

Ser Ser His Arg Asp Pro Asp Gln Glu Lys Gly Leu Arg Ile Ala Trp
        115                 120                 125

Gln Tyr Lys Lys Tyr Phe Gly Glu Asn Gln Gln Gly Phe Asp Ser Gln
    130                 135                 140

Asn Gly Lys His Glu Phe Cys Asn Asn Phe Asp Leu Arg Lys Pro Leu
145                 150                 155                 160

Glu Arg Gln Phe Leu Thr Gly Lys Leu Ile Glu Cys Ala Ser Ile Leu
                165                 170                 175

Asp Ser Pro Asn Leu Val Thr Phe His Asp Arg Cys Ala Thr Phe Leu
            180                 185                 190

Ser Gln Phe Pro Arg Asn Asp Ser Asn Ile Ser Cys Val Gly Arg Ile
        195                 200                 205

Ala Ile Gln Ser Phe Cys Ala Pro Gln Cys Gly Tyr Ser Asn Leu Glu
    210                 215                 220

Trp Asp Met Leu Ser Leu Leu Arg Ser Leu Lys Ser Met Leu Arg Ser
225                 230                 235                 240

Ser Asn Ala Val Ala Val Val Thr Phe Leu Pro Ser Leu Leu Ser Ser
                245                 250                 255

Ser Ser Ser Thr Arg Trp Gln His Ile Ala Asp Thr Leu Leu Ser Val
            260                 265                 270

Lys Ala Leu Pro Asp Glu Asp Lys Glu Leu Ala Thr Leu Leu Thr Gly
        275                 280                 285

Tyr Gln Asp Met Val Gly Leu Leu Asn Val Gln Lys Val Ala Gln Ile
    290                 295                 300

Asn Thr Gln Val Pro Val Ile Leu Asp Ala Thr Thr Phe Ser Ile Lys
305                 310                 315                 320

Leu Gln Lys Arg Arg Phe Leu Val Leu Glu Cys Leu Asn Gln Ala Pro
                325                 330                 335

Val Asp Gly Ser Ser Gly Ser Ser Tyr Gly Thr Ser Gly Ser Cys Ser
            340                 345                 350

Gly Ser Ser Lys Thr Gly Ser Leu Asp Phe
        355                 360

<210> SEQ ID NO 45
<211> LENGTH: 362
<212> TYPE: PRT
<213> ORGANISM: Cucumis melo

<400> SEQUENCE: 45

Met Ala Ala Thr Lys Pro Arg Thr Gly Ser Phe Ser Arg Asn Phe Ser
 1               5                  10                  15

Ser Ala His Ser Ser Lys Thr Pro Gly Tyr Lys His Gly Pro Asn Gly
                 20                  25                  30

Thr Thr Phe Ile Ser Ser Gly Ile Pro Asp Leu Asp Lys Ile Leu Cys
         35                  40                  45
```

Gly Gly Phe Pro Leu Gly Ser Leu Val Leu Val Met Glu Asp Ala Glu
            50                  55                  60

Ala Pro His His Met Leu Leu Arg Asn Phe Met Ser Gln Gly Leu
65                  70                  75                  80

Val His Asn Gln Pro Leu Leu Tyr Ala Ser Pro Ser Arg Asp Pro Arg
                    85                  90                  95

Gly Phe Leu Gly Thr Leu Pro Ser Pro Gly Ala Ser Lys Asp Lys
                100                 105                 110

Ser Arg Asp Asn Ser Ser Glu Gln Glu Lys Gly Leu Arg Ile Ala Trp
            115                 120                 125

Gln Tyr Lys Lys Tyr Phe Gly Asp Asp Gln Glu Ser Thr Asn Ala Ile
    130                 135                 140

Asp Ser Lys Tyr Glu Phe Cys Asn Asp Phe Asp Leu Arg Arg Pro Phe
145                 150                 155                 160

Asp Arg His Phe Phe Ser Gly Lys His Val Glu Cys Val Ser Ile Leu
                    165                 170                 175

Asp Ser Ser Ser Leu Ser Asn Phe Arg Asp Arg Cys Ala Thr Phe Leu
                180                 185                 190

Ser Gln Val Pro Arg Asn Asp Gly Asn Ile Ser Ser Ala Gly Arg Ile
            195                 200                 205

Ala Ile Gln Ser Leu Cys Ala Pro Gln Cys Asp His Ser Asn Met Glu
    210                 215                 220

Trp Glu Met Leu Ser Phe Leu Arg Tyr Leu Lys Ser Met Val Arg Ser
225                 230                 235                 240

Ser Asn Ala Val Ala Val Val Thr Phe Pro Pro Ser Leu Leu Ser Pro
                    245                 250                 255

Ser Phe Ser Lys Arg Trp Gln His Met Ala Asp Thr Leu Leu Ser Val
                260                 265                 270

Arg Ala Ile Pro Asp Glu Asp Lys Glu Leu Ala Lys Leu Leu Thr Gly
            275                 280                 285

Tyr Gln Asp Met Val Gly Leu Leu Asn Val His Lys Val Ala Gln Ile
    290                 295                 300

Asn Thr Gln Val Pro Lys Ile Leu Glu Ala Thr Thr Phe Ser Ile Lys
305                 310                 315                 320

Leu Gln Lys Arg Arg Tyr Leu Val Leu Glu Cys Leu Asn Gln Ala Pro
                    325                 330                 335

Ile Asp Val Ser Ser Gly Ser Ser Tyr Gly Ser Thr Gly Ser Cys Ser
                340                 345                 350

Gly Ser Ser Lys Thr Ala Ser Leu Glu Phe
            355                 360

<210> SEQ ID NO 46
<211> LENGTH: 375
<212> TYPE: PRT
<213> ORGANISM: Zea mays

<400> SEQUENCE: 46

Met Ala Ala Ala Gly Gly Arg Thr Leu Gly Arg Ser Ser Phe Ser Arg
1               5                   10                  15

Ala Thr Ser Asn Leu Val Ala Ser Ser Ser Gly Ala Ser Gly Val Lys
                20                  25                  30

Ile Gly Pro Asn Gly Ala Ser Phe Val Ser Ser Gly Ile Pro Asp Leu
            35                  40                  45

Asp Arg Ile Leu Gly Gly Gly Phe Leu Leu Gly Ser Val Val Met Ile

```
            50                  55                  60
Met Glu Asp Thr Asp Ala Pro His His Leu Leu Leu Arg Cys Phe
 65                  70                  75                  80

Met Ser Gln Gly Val Val His Lys Gln Pro Leu Leu Phe Ser Gly Ala
                 85                  90                  95

Met Lys Glu Pro Val Leu Phe Leu Gly Thr Leu Pro Ala Pro Val Ser
                100                 105                 110

Ser Ser Lys Glu Asp Gly Arg His Arg Ala Met Gly Pro Ala Ala Ser
                115                 120                 125

Ser Asp Gly Arg Ala Asn Asp Glu Gly Leu Arg Ile Ala Trp Gln Tyr
                130                 135                 140

Lys Lys Tyr Phe Gly Asp Asp Lys Thr Ser Arg Ala Glu His Lys Asp
145                 150                 155                 160

Asn Lys Gln Glu Phe Ser Asn Asp Phe Asp Leu Arg Lys Pro Leu Glu
                165                 170                 175

Arg His Leu Leu Asn Gly Gln Asn Ile Glu Cys Val Ser Thr Gln Asp
                180                 185                 190

Ala Asp Thr Leu Ser Ser Leu Gln Asp Cys Cys Ser Ala Phe Val Ser
                195                 200                 205

Lys Leu Pro Arg Lys Asp Gly Gly Ser Ser Thr Ala Gly Arg Ile Ala
210                 215                 220

Ile Gln Ser Leu Cys Ala Pro Gln Cys Arg Tyr Phe Glu Lys Asp Trp
225                 230                 235                 240

Asp Met Val Ser Phe Ile Arg Ser Leu Lys Ala Met Val Arg Ser Ser
                245                 250                 255

Asn Ser Val Ala Val Val Thr Phe Pro Ser Thr Val Leu Ser Asn Ser
                260                 265                 270

Phe Cys Lys Arg Trp Gln His Leu Ala Asp Thr Leu Leu Ser Ile Lys
                275                 280                 285

Ala Ile Pro Asp Glu Asp Lys Asp Leu Ala Lys Leu Leu Thr Gly Tyr
                290                 295                 300

Gln Asp Met Val Gly Phe Leu His Val His Lys Val Ala Gln Pro Asn
305                 310                 315                 320

Ser Gln Val Pro Val Ile Leu Glu Ala Ser Thr Leu Ser Leu Lys Leu
                325                 330                 335

Arg Lys Arg Arg Ser Leu Val Leu Glu Arg Leu Asn Gly Ala Pro Val
                340                 345                 350

Asp Gly Ser Ser Gly Pro Ser Ser Ala Ala Ser Ser Ser Cys Ser Ser
                355                 360                 365

Gln Gly Ser Gln Leu Asp Phe
                370                 375

<210> SEQ ID NO 47
<211> LENGTH: 377
<212> TYPE: PRT
<213> ORGANISM: Oryza sativa

<400> SEQUENCE: 47

Met Ala Ala Ala Gly Gly Gln Thr Val Gly Arg Ser Ser Phe Ser
  1               5                  10                  15

Arg Ala Ala Ala Pro His Val Ala Ser Ser Thr Ala Ala Gly Val
                 20                  25                  30

Lys Leu Gly Pro Asn Gly Ala Ala Phe Val Ser Gly Ile Pro Asp
                 35                  40                  45
```

Leu Asp Arg Ile Leu Gly Gly Gly Phe Leu Ile Gly Ser Val Val Met
 50                  55                  60

Ile Met Glu Asp Ser Asp Ala Pro His His Leu Leu Leu Arg Ser
 65                  70                  75                  80

Phe Met Ala Gln Gly Val Val His Lys Gln Pro Leu Leu Phe Ala Gly
                     85                  90                  95

Pro Met Lys Glu Pro Arg Leu Phe Leu Gly Thr Leu Pro Ala Val Ala
                 100                 105                 110

Ser Ser Lys Glu Asp Gly Arg Gln Arg Gly Met Gly Ala Gly Thr Ser
                 115                 120                 125

Ser Asp Gly Arg Thr Ser Asp Glu Ala Leu Arg Ile Ala Trp Gln Tyr
 130                 135                 140

Lys Lys Tyr Phe Gly Glu Glu Lys Thr Ser His Ala Glu His Arg Asp
145                  150                 155                 160

Asn Lys Gln Glu Phe Ser Asn Asp Phe Asp Leu Arg Lys Pro Leu Glu
                 165                 170                 175

Arg His Leu Leu Asn Ala Gln Asn Ile Glu Cys Ala Ser Thr Gln Glu
                 180                 185                 190

Gly Asp Thr Leu Gly Val Leu Gln Asp Arg Cys Ser Thr Phe Leu Ser
                 195                 200                 205

Lys Leu Pro Arg Lys Asp Gly Asn Ala His Ala Gly Arg Ile Ala
210                  215                 220

Ile Gln Ser Leu Cys Ala Pro Gln Cys Gly Tyr Phe Glu Lys Asp Trp
225                  230                 235                 240

Asp Met Val Ser Phe Ile Arg Ser Leu Lys Ala Met Val Arg Ala Ser
                 245                 250                 255

Asn Ala Val Ala Val Ile Thr Phe Pro Asn Thr Val Leu Ser Ser Ser
                 260                 265                 270

Phe Cys Lys Arg Trp Gln His Leu Ala Asp Thr Leu Leu Ser Ile Lys
                 275                 280                 285

Ala Ile Pro Asp Glu Asp Lys Glu Leu Ala Lys Leu Leu Thr Gly Tyr
                 290                 295                 300

Gln Asp Met Val Gly Phe Leu His Val His Lys Val Ala Gln Thr Asn
305                  310                 315                 320

Ser Gln Val Pro Val Ile Leu Glu Ala Ser Thr Phe Ser Leu Lys Leu
                 325                 330                 335

Arg Lys Arg Arg Ser Leu Val Leu Glu Arg Leu Asn Gln Ala Pro Val
                 340                 345                 350

Asp Gly Ser Gly Gly Pro Ser Leu Asp Ala Ser Gly Ser Cys Ser Ser
                 355                 360                 365

Ser Ser Gln Gly Ser Gln Leu Asp Phe
    370                 375

<210> SEQ ID NO 48
<211> LENGTH: 363
<212> TYPE: PRT
<213> ORGANISM: Eucalyptis grandis

<400> SEQUENCE: 48

Met Ala Thr Pro Lys Thr Arg Ala Ser Ser Phe Ser Arg Asn Val Pro
 1               5                  10                  15

Ser Thr Ala Ala Pro Gln Val Pro Gly Val Lys Ser Gly Pro Asn Gly
                 20                  25                  30

Thr Leu Phe Leu Ser Ser Gly Ile Ser Asp Leu Asp Lys Ile Leu Gly
                 35                  40                  45

-continued

```
Gly Gly Phe Pro Leu Gly Ser Leu Val Val Met Glu Asp Pro Glu
     50              55              60

Ala Pro His His Met Leu Leu Arg Asn Phe Met Ser Gln Gly Leu
65              70              75              80

Val Leu Asn Gln Pro Leu Leu Tyr Ala Ser Pro Ala Lys Asp Pro Arg
            85              90              95

Gly Phe Leu Gly Thr Leu Pro Ser Pro Val Ser Ser Lys Asp Asp Lys
            100             105             110

Pro Leu Asn Arg Asp Ser Glu Gln Glu Lys Gly Leu Arg Ile Ala Trp
            115             120             125

Gln Tyr Lys Lys Tyr Phe Gly Glu Asn Gln Gln Asn Ser Asn Ser Gln
            130             135             140

Arg Asp Asn Lys Phe Glu Phe Cys Asn Glu Phe Asp Leu Arg Lys Pro
145             150             155             160

Leu Gln Arg Gln Phe Leu Ser Gly Gln Arg Val Glu Cys Met Ser Thr
                165             170             175

Gln Asp Ser Pro Asp Leu Ala Ala Leu His Asp Arg Cys Ala Thr Phe
            180             185             190

Leu Lys Gln Phe Phe Arg Thr Asp Gly Asn Ile Ser Gly Ala Gly Arg
            195             200             205

Ile Ala Ile Gln Ser Phe Cys Ala Pro Gln Cys Thr Tyr Phe Asp Lys
210             215             220

Glu Trp His Val Leu Ser Phe Ile Arg Ser Leu Arg Ser Met Ile Arg
225             230             235             240

Ser Ser Asn Ala Val Val Ile Leu Ser Phe Pro Pro Ser Leu Leu Ser
            245             250             255

Pro Ser Phe Ser Lys Arg Leu Gln His Met Ala Asp Thr Leu Leu Ser
            260             265             270

Val Arg Ala Ile Pro Asp Glu Asp Lys Asp Leu Ala Lys Leu Leu Thr
            275             280             285

Gly Tyr Gln Asp Met Ile Gly Leu Leu Ser Val His Lys Val Ala Arg
            290             295             300

Ile Asn Thr Gln Val Pro Ile Ile Leu Glu Ala Ala Thr Phe Ser Ile
305             310             315             320

Lys Leu Gln Lys Arg Lys Phe Leu Val Leu Glu Cys Leu Asn Gln Ala
            325             330             335

Pro Val Asp Gly Ser Ser Gly Thr Ser Tyr Ala Thr Ser Gly Ser Cys
            340             345             350

Ser Val Ser Ser Lys Gly Gly Ser Leu Asp Phe
            355             360
```